US009788906B2

(12) United States Patent
Piron et al.

(10) Patent No.: US 9,788,906 B2
(45) Date of Patent: Oct. 17, 2017

(54) CONTEXT AWARE SURGICAL SYSTEMS FOR INTRAOPERATIVELY CONFIGURING IMAGING DEVICES

(71) Applicants: Cameron Piron, Toronto (CA); Michael Wood, Toronto (CA); Gal Sela, Toronto (CA); Joshua Richmond, Toronto (CA); Murugathas Yuwaraj, Markham (CA); Stephen McFadyen, Toronto (CA); Alex Panther, Toronto (CA); Nishanthan Shanmugaratnam, Scarborough (CA); William Lau, Toronto (CA); Monroe M. Thomas, Toronto (CA); Wes Hodges, London (CA); Simon Alexander, Toronto (CA); David Gallop, Toronto (CA)

(72) Inventors: Cameron Piron, Toronto (CA); Michael Wood, Toronto (CA); Gal Sela, Toronto (CA); Joshua Richmond, Toronto (CA); Murugathas Yuwaraj, Markham (CA); Stephen McFadyen, Toronto (CA); Alex Panther, Toronto (CA); Nishanthan Shanmugaratnam, Scarborough (CA); William Lau, Toronto (CA); Monroe M. Thomas, Toronto (CA); Wes Hodges, London (CA); Simon Alexander, Toronto (CA); David Gallop, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 42 days.

(21) Appl. No.: 14/771,643

(22) PCT Filed: Mar. 14, 2014

(86) PCT No.: PCT/CA2014/050265
§ 371 (c)(1),
(2) Date: Aug. 31, 2015

(87) PCT Pub. No.: WO2014/139018
PCT Pub. Date: Sep. 18, 2014

(65) Prior Publication Data
US 2016/0015471 A1    Jan. 21, 2016

Related U.S. Application Data

(60) Provisional application No. 61/801,530, filed on Mar. 15, 2013, provisional application No. 61/800,695, (Continued)

(51) Int. Cl.
*A61B 19/00* (2006.01)
*G06T 11/00* (2006.01)
(Continued)

(52) U.S. Cl.
CPC ...... *A61B 19/5244* (2013.01); *A61B 1/00059* (2013.01); *A61B 1/045* (2013.01);
(Continued)

(58) Field of Classification Search
CPC ......... A61B 34/20; A61B 90/90–90/98; A61B 2034/2055–2034/2057
See application file for complete search history.

(56) References Cited

U.S. PATENT DOCUMENTS 5,315,342 A    5/1994  Cocca
5,452,723 A    9/1995  Wu et al.
(Continued)

FOREIGN PATENT DOCUMENTS

CN    202568266 U    12/2012
DE    102011016138 A1    10/2012
(Continued)

OTHER PUBLICATIONS

International Search Report (PCT/CA2014/050265) dated Jul. 18, 2014.
(Continued)

*Primary Examiner* — Serkan Akar
(74) *Attorney, Agent, or Firm* — Hill & Schumacher

(57) ABSTRACT

Systems and methods are provided in which devices that are employed during a medical procedure are adaptively con-
(Continued)

figured during the medical procedure, based on input or feedback that is associated with the current state, phase or context of the medical procedure. In some example embodiments, the input is obtained via the identification of one or more medical instruments present within a region of interest, and this input may be employed to determine configuration parameters for configuring the device. In other example embodiments, the input may be based on the image-based detection of a measure associated with the phase or context of the medical procedure, and this input may be employed to adaptively control the device based on the inferred context or phase of the medical procedure. In other embodiments, images from one imaging modality may be employed to adaptively switch to another imaging modality.

13 Claims, 38 Drawing Sheets

Related U.S. Application Data filed on Mar. 15, 2013, provisional application No. 61/800,787, filed on Mar. 15, 2013, provisional application No. 61/800,911, filed on Mar. 15, 2013, provisional application No. 61/801,746, filed on Mar. 15, 2013, provisional application No. 61/801,143, filed on Mar. 15, 2103, provisional application No. 61/801,282, filed on Mar. 15, 2013, provisional application No. 61/800,155, filed on Mar. 15, 2013, provisional application No. 61/818,255, filed on May 1, 2013, provisional application No. 61/818,325, filed on May 1, 2013, provisional application No. 61/818,280, filed on May 1, 2013, provisional application No. 61/818,223, filed on May 1, 2013, provisional application No. 61/924,993, filed on Jan. 8, 2014.

(51) Int. Cl.

| | | |
|---|---|---|
| *G06T 7/00* | (2017.01) | |
| *A61B 1/00* | (2006.01) | |
| *A61B 1/045* | (2006.01) | |
| *A61B 6/00* | (2006.01) | |
| *A61B 90/96* | (2016.01) | |
| *A61B 90/30* | (2016.01) | |
| *A61B 90/90* | (2016.01) | |
| *A61B 90/94* | (2016.01) | |
| *A61B 90/98* | (2016.01) | |
| *G06T 7/70* | (2017.01) | |
| *A61B 6/03* | (2006.01) | |
| *A61B 8/13* | (2006.01) | |
| *A61B 18/14* | (2006.01) | |
| *A61B 8/08* | (2006.01) | |
| *A61B 90/00* | (2016.01) | |
| *A61B 34/20* | (2016.01) | |
| *A61B 34/00* | (2016.01) | |
| *A61B 90/50* | (2016.01) | |
| *A61B 34/30* | (2016.01) | |

(52) U.S. Cl.
CPC ............ *A61B 6/5247* (2013.01); *A61B 34/20* (2016.02); *A61B 90/30* (2016.02); *A61B 90/90* (2016.02); *A61B 90/94* (2016.02); *A61B 90/96* (2016.02); *A61B 90/98* (2016.02); *G06T 7/0012* (2013.01); *G06T 7/70* (2017.01); *G06T 11/003* (2013.01); *A61B 6/03* (2013.01); *A61B 8/0808* (2013.01); *A61B 8/0841* (2013.01); *A61B 8/13* (2013.01); *A61B 18/14* (2013.01); *A61B 34/30* (2016.02); *A61B 90/50* (2016.02); *A61B 2034/2055* (2016.02); *A61B 2034/2065* (2016.02); *A61B 2034/252* (2016.02); *A61B 2034/256* (2016.02); *A61B 2090/306* (2016.02); *A61B 2090/3618* (2016.02); *A61B 2090/373* (2016.02); *A61B 2090/374* (2016.02); *A61B 2090/378* (2016.02); *A61B 2090/3735* (2016.02); *A61B 2090/3762* (2016.02); *A61B 2090/3983* (2016.02); *G06T 2207/10081* (2013.01); *G06T 2207/10088* (2013.01); *G06T 2207/10104* (2013.01); *G06T 2207/10132* (2013.01); *G06T 2207/30016* (2013.01)

(56) References Cited

U.S. PATENT DOCUMENTS

| | | |
|---|---|---|
| 6,092,722 A | 7/2000 | Heinrichs |
| 6,357,877 B2 | 3/2002 | Takada |
| 6,821,245 B2 | 11/2004 | Cline |
| 6,899,675 B2 | 5/2005 | Cline |
| 7,399,300 B2 | 7/2008 | Bertolero |
| 7,607,440 B2 | 10/2009 | Coste-Maniere et al. |
| 7,871,164 B2 | 1/2011 | Luther |
| 7,892,165 B2 | 2/2011 | Nakamura |
| 8,019,405 B2 | 9/2011 | Weber |
| 8,070,682 B2 | 12/2011 | Zhu |
| 8,144,410 B2 | 3/2012 | Yazdanfar |
| 8,231,526 B2 | 7/2012 | Yabe et al. |
| 8,294,081 B2 | 10/2012 | Rosenheimer |
| 8,335,557 B2 | 12/2012 | Maschke |
| 8,406,859 B2 | 3/2013 | Zuzak |
| 8,439,830 B2 | 5/2013 | McKinley |
| 8,520,919 B2 | 8/2013 | Stepp et al. |
| 8,548,822 B2 | 10/2013 | Moctezuma de la Barrera |
| 8,945,149 B2 | 2/2015 | Kim et al. |
| 2003/0109780 A1* | 6/2003 | Coste-Maniere .. A61B 19/2203 600/407 |
| 2004/0024311 A1* | 2/2004 | Quaid, III ............. A61B 34/20 600/428 |
| 2006/0058616 A1* | 3/2006 | Marquart ............... A61B 34/20 600/407 |
| 2006/0142657 A1* | 6/2006 | Quaid .................... A61N 1/372 600/424 |
| 2007/0083098 A1* | 4/2007 | Stern ................. A61B 1/00188 600/407 |
| 2008/0019127 A1 | 1/2008 | Dick et al. |
| 2008/0020714 A1 | 1/2008 | Mezhinsky |
| 2008/0200926 A1 | 8/2008 | Verard |
| 2009/0105579 A1* | 4/2009 | Garibaldi ........... A61B 1/00158 600/409 |
| 2009/0306581 A1 | 12/2009 | Claus |
| 2010/0141744 A1 | 6/2010 | Amling |
| 2010/0167334 A1 | 7/2010 | Williamson, IV |
| 2011/0211056 A1 | 9/2011 | Publicover |
| 2011/0280810 A1 | 11/2011 | Hauger et al. |
| 2011/0282192 A1 | 11/2011 | Axelrod |
| 2012/0002012 A1 | 1/2012 | O'Grady |
| 2012/0179189 A1 | 7/2012 | Zingaretti |
| 2012/0206050 A1 | 8/2012 | Spero |
| 2012/0265023 A1 | 10/2012 | Berci |
| 2013/0016200 A1 | 1/2013 | Ovod |
| 2013/0053648 A1 | 2/2013 | Abovitz |
| 2013/0204287 A1 | 8/2013 | Mark et al. |
| 2013/0231681 A1 | 9/2013 | Robinson et al. |
| 2014/0006049 A1 | 1/2014 | Moctezuma de la Barrera |
| 2014/0088990 A1 | 3/2014 | Nawana et al. |
| 2014/0171873 A1 | 6/2014 | Mark |

FOREIGN PATENT DOCUMENTS

| | | |
|---|---|---|
| DE | 102011087357 A1 | 5/2013 |
| EP | 2020202 B9 | 9/2011 |
| EP | 2514357 A1 | 10/2012 |
| EP | 2547093 A1 | 1/2013 |
| GB | 2376144 B | 3/2005 |

(56) References Cited

FOREIGN PATENT DOCUMENTS

| GB | 2500304 A | 9/2013 |
|---|---|---|
| JP | 4846928 B2 | 12/2011 |
| WO | 2009137421 | 11/2009 |
| WO | 2011017550 | 2/2011 |
| WO | 2012138943 | 10/2012 |
| WO | 201325320 A1 | 2/2013 |
| WO | 2013018934 | 2/2013 |

OTHER PUBLICATIONS

Written Opinion (PCT/CA2014/050265) dated Jul. 18, 2014.
IPRP chapter II (PCT/CA2014/050265)—corrected version—dated Jul. 23, 2015.

* cited by examiner

| Identified Medical Instrument | Camera Configuration Parameters |
|---|---|
| Suction Device | Reduce shutter speed, reduce gain, and reduce sensitivity; rationale: significant fluid is likely in the surgical field producing surface glare that will saturate the camera |
| Resection Device | Increase gain and sensitivity; rationale: as resection is being performed the optical system will be at a high zoom factor reducing the light reaching the camera, and increase in camera gain and sensitivity will improve image contrast |
| Electrocautery Device | Color saturation to emphasize red wavelengths; rationale: instrument likely being used for cauterization of bleeding vessels, thus significant blood is likely in the surgical field, emphasizing red wavelengths will improve image contrast |
| Suction and Resection Devices | Maintain shutter speed, gain, and sensitivity; rationale: while significant fluid is likely in the surgical field producing surface glare, the system will likely be at high zoom and require the additional image gain and sensitivity |
| Suction and Electrocautery Devices | Color saturation to emphasize red wavelengths; rationale: tools likely being used for cauterization of bleeding vessels, thus significant blood is likely in the surgical field, emphasizing red wavelengths will improve image contrast |
| Resection and Electrocautery Devices | Color saturation to emphasize red wavelengths; rationale: tools likely being used for cauterization of bleeding micro-vessels, thus significant blood is likely in the surgical field, emphasizing red wavelengths will improve image contrast |

FIG. 5C

| Identified Medical Instrument | Imaging Optics Assembly Configuration Parameters |
|---|---|
| Suction Device | Cross imaging optics polarization with illumination optics polarization; rationale: significant fluid is likely in the surgical field producing surface glare that will obscure surgical field, crossed polarizers will eliminate this glare |
| Resection Device | Increase zoom; rationale: as microresection is being performed the optical system should be at a higher zoom to better visualize the resection |
| Electrocautery Device | Cross imaging optics polarization with illumination optics polarization; rationale: significant fluid (blood) is likely in the surgical field producing surface glare that will obscure surgical field including the bleeding vessels, crossed polarizers will eliminate this glare |
| Suction and Resection Devices | Cross imaging optics polarization with illumination optics polarization and increase zoom; rationale: significant fluid is likely in the surgical field producing surface glare that will obscure surgical field, crossed polarizers will eliminate this glare, and an increase in zoom will aid in visualization of microresection |
| Suction and Electrocautery Devices | Cross imaging optics polarization with illumination optics polarization; rationale: significant fluid (blood) is likely in the surgical field producing surface glare that will obscure surgical field including the bleeding vessels, crossed polarizers will eliminate this glare |
| Resection and Electrocautery Devices | Cross imaging optics polarization with illumination optics polarization and increase zoom; rationale: significant fluid is likely in the surgical field producing surface glare that will obscure surgical field, crossed polarizers will eliminate this glare, and an increase in zoom will aid in visualization of microresection |

FIG. 5D

| Identified Medical Instrument | Illuminator Configuration Parameters |
|---|---|
| Suction Device | Set illumination angle to be non-perpendicular with imaging plane; rationale: significant fluid is likely in the surgical field producing surface glare that will obscure surgical field, the illumination being non-perpendicular with imaging plane will eliminate the majority of this glare |
| Resection Device | Increase intensity; rationale: as microresection is being performed the optical system should be at a higher zoom to better visualize the resection, increasing the intensity accordingly increase the light reaching the camera and improve contrast and resolution |
| Electrocautery Device | Set illumination angle to be non-perpendicular with imaging plane and increase intensity of red wavelengths; rationale: significant fluid is likely in the surgical field producing surface glare that will obscure surgical field, the illumination being non-perpendicular with imaging plane will eliminate the majority of this glare, increasing the red wavelengths will increase overall light levels as these wavelengths are not absorbed by blood |
| Suction and Resection Devices | Set illumination angle to be non-perpendicular with imaging plane and increase light intensity; rationale: significant fluid is likely in the surgical field producing surface glare that will obscure surgical field, the illumination being non-perpendicular with imaging plane will eliminate the majority of this glare, as microresection is being performed the optical system should be at a higher zoom to better visualize the resection, increasing the intensity will increase the light reaching the camera and improve contrast and resolution |
| Suction and Electrocautery Devices | Set illumination angle to be non-perpendicular with imaging plane and increase intensity of red wavelengths; rationale: significant fluid is likely in the surgical field producing surface glare that will obscure surgical field, the illumination being non-perpendicular with imaging plane will eliminate the majority of this glare, increasing the red wavelengths will increase overall light levels as these wavelengths are not absorbed by blood |
| Resection and Electrocautery Devices | Set illumination angle to be non-perpendicular with imaging plane, increase light intensity, and increase intensity of red wavelengths; rationale: significant fluid is likely in the surgical field producing surface glare that will obscure surgical field, the illumination being non-perpendicular with imaging plane will eliminate the majority of this glare, as microresection is being performed the optical system should be at a higher zoom to better visualize the resection, increasing the intensity will increase the light reaching the camera and improve contrast and resolution, increasing the red wavelengths will increase overall light levels as these wavelengths are not absorbed by blood |

FIG. 5E

| Identified Medical Instrument | Illuminator Focusing Optics Configuration Parameters |
|---|---|
| Suction Device | Cross illumination polarization with imaging optics polarizer; rationale: significant fluid is likely in the surgical field producing surface glare that will obscure surgical field, crossed polarizers will eliminate this glare |
| Resection Device | Decrease spot illumination spot size; rationale: as resection is being performed the optical system will be at a high zoom factor reducing the light reaching the camera, reducing the spot size will increase the light reaching the camera |
| Electrocautery Device | Cross illumination polarization with imaging optics polarizer; rationale: significant fluid (blood) is likely in the surgical field producing surface glare that will obscure surgical field, crossed polarizers will eliminate this glare |
| Suction and Resection Devices | Cross illumination polarization with imaging optics polarizer and decrease illumination spot size; rationale: significant fluid (blood) is likely in the surgical field producing surface glare that will obscure surgical field, crossed polarizers will eliminate this glare, as microresection is being performed the optical system will be at a high zoom factor reducing the light reaching the camera, reducing the spot size will increase the light reaching the camera |
| Suction and Electrocautery Devices | Cross illumination polarization with imaging optics polarizer; rationale: significant fluid (blood) is likely in the surgical field producing surface glare that will obscure surgical field, crossed polarizers will eliminate this glare |
| Resection and Electrocautery Devices | Cross illumination polarization with imaging optics polarizer and decrease illumination spot size; rationale: significant fluid (blood) is likely in the surgical field producing surface glare that will obscure surgical field, crossed polarizers will eliminate this glare, as microresection is being performed the optical system will be at a high zoom factor reducing the light reaching the camera, reducing the spot size will increase the light reaching the camera |

FIG. 5F

| Identified Medical Instrument | Camera Configuration Parameters |
|---|---|
| Instrument 1 | Configuration parameter set 1 |
| Instrument 2 | Configuration parameter set 2 |
| Instrument 3 | Configuration parameter set 3 |
| Instrument 4 | Configuration parameter set 4 |
| Instrument 5 | Configuration parameter set 5 |
| Instrument 6 | Configuration parameter set 6 |

FIG. 5G

| Identified Medical Instrument | Camera Configuration Parameters |
|---|---|
| Suction Device | Reduce shutter speed, reduce gain, and reduce sensitivity; rationale: significant fluid is likely in the surgical field producing surface glare that will saturate the camera |
| Resection Device | Increase gain and sensitivity; rationale: as microresection is being performed the optical system will be at a high zoom factor reducing the light reaching the camera, and increase in camera gain and sensitivity will improve image contrast |
| Electrocautory Device | Color saturation to emphasize red wavelengths; rationale: instrument likely being used for cauterization of bleeding vessels, thus significant blood is likely in the surgical field, emphasizing red wavelengths will improve image contrast |
| Suction and Resection Devices | Maintain shutter speed, gain, and sensitivity; rationale: while significant fluid is likely in the surgical field producing surface glare, the system will likely be at high zoom and require the additional image gain and sensitivity |
| Suction and Electrocautory Devices | Color saturation to emphasize red wavelengths; rationale: tools likely being used for cauterization of bleeding vessels, thus significant blood is likely in the surgical field, emphasizing red wavelengths will improve image contrast |
| Resection and Electrocautory Devices | Color saturation to emphasize red wavelengths; rationale: tools likely being used for cauterization of bleeding micro-vessels, thus significant blood is likely in the surgical field, emphasizing red wavelengths will improve image contrast |
| No instrument identified | Increase gain and sensitivity; rationale: the most likely procedure being performed and the one where the camera configuration is most important is when the surgeon is performing resection and needs ideal tissue contrast for differentiation. Therefore as resection is being performed the optical system will be at a high zoom factor reducing the light reaching the camera, and increase in camera gain and sensitivity will improve image contrast |

FIG. 5H

| Procedure Name | Identified Medical Instrument | Camera Configuration Parameters |
|---|---|---|
| Port Based Tumor Resection | Suction Device | Reduce shutter speed, reduce gain, and reduce sensitivity; rationale: significant fluid is likely in the surgical field producing surface glare that will saturate the camera |
| Port Based Tumor Resection | Resection Device | Increase gain and sensitivity; rationale: as resection is being performed the optical system will be at a high zoom factor reducing the light reaching the camera, and increase in camera gain and sensitivity will improve image contrast |
| Port Based Tumor Resection | Electrocautory Device | Color saturation to emphasize red wavelengths; rationale: instrument likely being used for cauterization of bleeding vessels, thus significant blood is likely in the surgical field, emphasizing red wavelengths will improve image contrast |
| Port Based Tumor Resection | Suction and Resection Devices | Maintain shutter speed, gain, and sensitivity; rationale: while significant fluid is likely in the surgical field producing surface glare, the system will likely be at high zoom and require the additional image gain and sensitivity |
| Port Based Tumor Resection | Suction and Electrocautory Devices | Color saturation to emphasize red wavelengths; rationale: tools likely being used for cauterization of bleeding vessels, thus significant blood is likely in the surgical field, emphasizing red wavelengths will improve image contrast |
| Port Based Tumor Resection | Resection and Electrocautory Devices | Color saturation to emphasize red wavelengths; rationale: tools likely being used for cauterization of bleeding micro-vessels, thus significant blood is likely in the surgical field, emphasizing red wavelengths will improve image contrast |
| Port Based Clot Removal | Port | Camera will zoom to maximize view of distal end of the port Rationale: to assist the surgeon in locating the clot once in the surgical area of interest within the brain |
| Port Based Clot Removal | Suction device | Color saturation to emphasize red wavelengths: rationale: For clot removal surgery (caused by a Intracranial hemorrhage) the suction device is used to remove excess blood from the surgical site of interest. Therefore when the suction device is used in port based clot removal surgery the system knows the site will be occluded by a lot of blood. To improve visibility the colour saturation configuration of the camera is adjusted to emphasize red wavelengths |
| Lumbar Microscopic Discectomy and Decompression | Retractor | Increase gain and sensitivity; rationale: as the nerve is being retracted the optical system will be at a high zoom factor reducing the light reaching the camera, and increase in camera gain and sensitivity will improve image contrast allowing the surgeon to more easily differentiate the nerve tissue from other tissue within the surgical area of interest at the distal end of the port |
| Lumbar Microscopic Discectomy and Decompression | Pituitary Forceps and Retractor | Color saturation to emphasize spinal bone; rationale: in this stage of the surgery the fragmented bone is being removed from the surgical site of interest, with optimal contrast for viewing bone the surgeon will be able to more effectively remove all of the fragmented bone without leaving smaller less visible pieces behind. |
| Lumbar Microscopic Discectomy and Decompression | Irrigation Cannula | Reduce shutter speed, reduce gain, and reduce sensitivity; rationale: During this step in the procedure pressurized liquid is used to dislodge any remaining herniated disc fragments from the area. As such significant fluid is likely in the surgical field producing surface glare that will saturate the camera |

FIG. 5I

| Identified Medical Instrument | Procedure Phase | System Configuration Parameters |
|---|---|---|
| Pointer Tool | Craniotomy (2100) | Follow pointer tool for confirmation of drilling boundaries |
| Scalpel | Craniotomy (2100) | UI overlays cuts to be made on skull of patient based on registration of 3D rendered MRI scan of patients brain and patients brain |
| Neurosurgical Drill | Craniotomy (2100) | UI reconfigures and provides information on how deep the drill is into the skull |
| Ultrasound Imaging device | Cannulation (2110) | UI reconfigures to show Ultrasound view |
| Introducer and Port | Cannulation (2110) | Robotic arm is reconfigured to move imaging device approximately orthogonal to cannulation location to show graduation marks on introducer as its inserted into the brain |
| Resection Tool | Gross Resection (2120) | The system configures the imaging device to simultaneously capture visible light and scans for fluorescence imaging as well as glare |
| Resection Tool and Surgical Forceps | Gross Resection (2120) | The system configures the imaging device to simultaneously capture visible light and scans for fluorescence imaging as well as glare |
| Electrocautery Device | Bleeding Management (2130) | The system configures the imaging device to begin NIR imaging to provide more light penetration through the blood and consequently more ability to see through to the occluded surgical area of interest |
| Resection Tool and Pointer Tool Mounted with Raman Probe | Fine Resection (2140) | The system configures the imaging device to begin Polarization Sensitive Imaging to provide better information of structural surfaces at the surgical site of interest. To prevent the surgeon from accidentally damaging vital neural tracts |

FIG. 5J

| Identified Medical Instrument | Robotic Arm Configuration Parameters |
|---|---|
| Neurosurgical Drill | The robotic arm will align the camera to view the drilling area, at the maximum distance it can safely reach from the drilling area. (in a typical surgery this may be 40-60cm)<br>rationale: during the craniotomy when the drilling of the skull is performed the surgeon normally does not utilize the scope for viewing while the drilling is being done, and hence removal of the scope from around the surgical space will result in less occlusion of the surgeons view. |
| Introducer (Obturator) | The robotic arm will align the external scope to provide a orthogonal view as the introducer is cannulated<br>rationale: this orthogonal view provides the external scope the ability to view the graduation marks on the side of the introducer as it is cannulated into the brain, providing the depth that the introducer is inserted before |
| Port | The robotic arm will align the external scope to provide a coaxial view of the surgical area of interest at the distal end of the port<br>rationale: so that the surgeon has an enhanced view of the surgical area of interest where the surgery is being performed |
| Introducer (Obturator) and Port | The robotic arm will align the external scope to provide a orthogonal view as the introducer is cannulated<br>rationale: this orthogonal view provides the external scope the ability to view the graduation marks on the side of the introducer as it is cannulated into the brain, providing the depth that the introducer is inserted before<br>note: when the port and introducer are both recognized the presence of the introducer implies the cannulation process is occurring. |
| Neurosurgical Drill | The robotic arm will align the camera to view the drilling area, at the maximum distance it can safely reach from the drilling area. (in a typical surgery this may be 40-60cm)<br>rationale: during the craniotomy when the drilling of the skull is performed the surgeon normally does not utilize the scope for viewing while the drilling is being done, and hence removal of the scope from around the surgical space will result in less occlusion of the surgeons view. |
| Introducer (Obturator) | The robotic arm will align the external scope to provide a orthogonal view as the introducer is cannulated<br>rationale: this orthogonal view provides the external scope the ability to view the graduation marks on the side of the introducer as it is cannulated into the brain, providing the depth that the introducer is inserted before |

FIG. 5K

| Identified Medical Instrument | User Interface Configuration Parameters |
|---|---|
| Suction Device | UI configures to display a control section which changes the suction force of the suction device |
| Port and Resection Device | UI configures to provide an option to turn on various imaging modes for tumor differentiation: these would be represented as buttons some examples being Raman probe, Hyperspectral imaging, Polarization Sensitive imaging, NIR imaging, OCT imaging, PSOCT imaging.<br>rationale: when resecting a tumor it is important to avoid resecting healthy brain tissue as this can cause unnecessary loss of function for the patient |
| Introducer (obtruator) | UI configures to display any potential tracts the introducer may come into contact with during insertion into the brain, it would also provide a display of force felt by the distal tip and sides of the port as well as sound an alarm if this force exceeded a threshold.<br>rationale: Determining the amount of force felt by the introducer during the penetration of the brain and its tissue, can be an important factor. This force sensor can help determine the density of the tumor when it is approached which can assist the surgeon by helping to adjust their trajectory in the case of a tumor role. In addition the force sensor can also help a surgeon to determine if too much damage would be caused if they were to penetrate at a particular point. |
| Port and Therapeutic device | UI configures to display information about the tumor that has been resected during that surgery, and also displays information on previously resected tumors of similar makeup and the effects of various solutions on them. The UI also configures to display and provide an option to choose any potential therapeutic solutions which could be potentially delivered by the therapeutic device to the remaining tumor tissue or any mixture of therapeutic solutions.<br>rationale: Unique tumors may require unique solutions, therefore having information on tumors and their reaction to various types of therapeutic solutions and mixtures of those solutions can assist the surgeon in being more effective in providing therapy to the patient. |
| Pointer Device | UI configures to display a wide-field camera view of the surgical area of interest and the registered preoperative image of the patients anatomy of interest.<br>rationale: before beginning surgery it is important to confirm correct registration of the preoperative images to assure the correct trajectory is taken to access the tumor. This is done by touching points on the patient and making sure they're correctly located on the preoperative image data.<br>note: since there is no port detected it can be assumed that we are in a pre-surgical state and the reason is |
| Pointer device and port | UI configures to provide a view of the distal end of the port as acquired by the external scope and a cursor which follows the tip of the pointer tool when it occludes the view of the distal end of the port. The cursor is used when prompted by the surgeon to outline an area that needs to be zoomed up on or stored by the system.<br>rationale: The pointer device when used in combination with the port can be used to identify surgical areas of interest to the system by the user. These areas of interest may require a greater zoom or a different type of imaging modality to satisfactorily complete the surgery. |

FIG. 5L

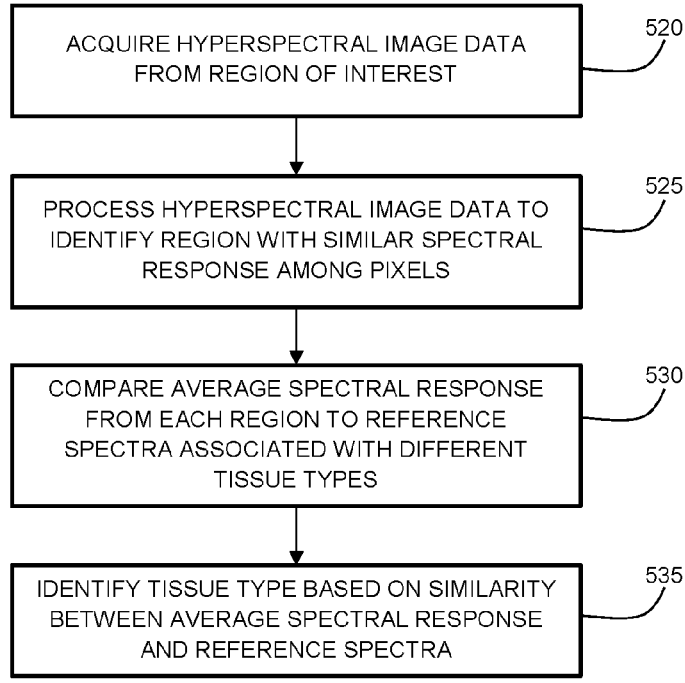

FIG. 10A

| Tissue Type | Illuminator Configuration Parameters |
|---|---|
| Brain White Matter | To enhance light penetration: increase illumination power at visible wavelengths above 500 nm, to enhance surface contrast: decrease illumination power at visible wavelengths bellow 500 nm |
| Brain Grey Matter | To enhance light penetration: increase illumination power at visible wavelengths above 550 nm, to enhance surface contrast: decrease illumination power at visible wavelengths bellow 550 nm |
| Muscle | To enhance light penetration: increase illumination power at visible wavelengths above 600 nm, to enhance surface contrast: decrease illumination power at visible wavelengths bellow 600 nm |

FIG. 10B

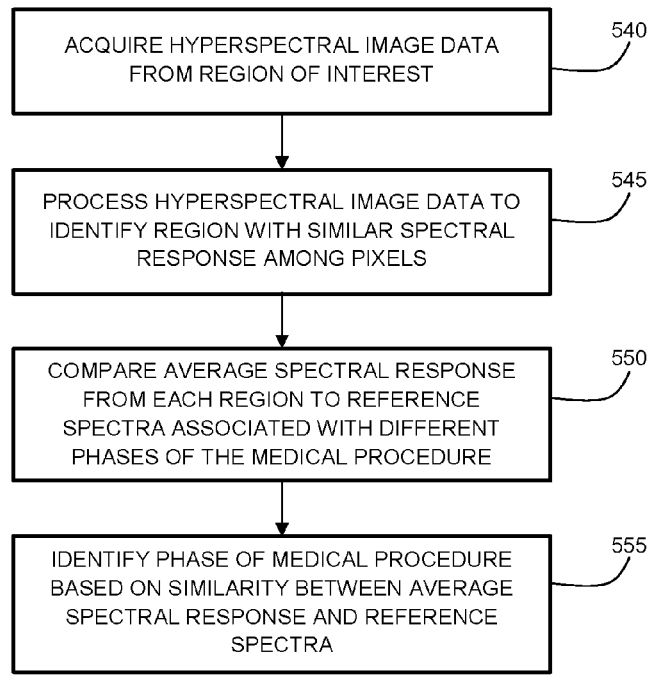

FIG. 11A

| Phase of Medical Procedure | Camera Configuration Parameters |
|---|---|
| Craniotomy | Zoomed Out |
| Cannulation | Oriented almost orthogonal to port with introducer, and zoomed in on the graduation marks as the port with introducer is inserted into brain through dura. |
| Gross Resection | Zoomed in on circumference of port opening. With the focus optimized for all of the tissue at the distal end of the port |
| Fine Resection | Zoomed in on tip of tool, down the port, on tissue being resected. In addition the focus of the camera will be on the tissue being resected and not the entire image. |

FIG. 11B

CONTEXT AWARE SURGICAL SYSTEMS FOR INTRAOPERATIVELY CONFIGURING IMAGING DEVICES

CROSS-REFERENCE TO RELATED APPLICATIONS

This application is a National Phase application claiming the benefit of the international PCT Patent Application No. PCT/CA2014/050265, filed on Mar. 14, 2014, in English, which claims priority to U.S. Provisional Application No. 61/801,530, titled "SYSTEMS, DEVICES AND METHODS FOR PLANNING, IMAGING, AND GUIDANCE OF MINIMALLY INVASIVE SURGICAL PROCEDURES" and filed on Mar. 15, 2013, the entire contents of which is incorporated herein by reference, and to U.S. Provisional Application No. 61/800,695, titled "EXTERNAL VIDEO SCOPE FOR PORT-BASED SURGICAL PROCEDURES" and filed on Mar. 15, 2013, the entire contents of which is incorporated herein by reference and to U.S. Provisional Application No. 61/800,787, titled "POLARIZED LIGHT IMAGING DEVICE" and filed on Mar. 15, 2013, the entire contents of which is incorporated herein by reference, and to U.S. Provisional Application No. 61/800,911, titled "HYPERSPECTRAL IMAGING DEVICE" and filed on Mar. 15, 2013, the entire contents of which is incorporated herein by reference and to U.S. Provisional Application No. 61/801,746, titled "INSERT IMAGING DEVICE" and filed on Mar. 15, 2013, the entire contents of which is incorporated herein by reference and to U.S. Provisional Application No. 61/801,143, titled "INSERTABLE MAGNETIC RESONANCE IMAGING COIL PROBE FOR MINIMALLY INVASIVE CORRIDOR-BASED PROCEDURES" and filed on Mar. 15, 2013, the entire contents of which is incorporated herein by reference and to U.S. Provisional Application No. 61/801,282, titled "SYSTEMS AND METHODS FOR PATHOLOGY TRACKING" and filed on Mar. 15, 2013, the entire contents of which is incorporated herein by reference and to U.S. Provisional Application No. 61/800,155, titled "PLANNING, NAVIGATION AND SIMULATION SYSTEMS AND METHODS FOR MINIMALLY INVASIVE THERAPY" and filed on Mar. 15, 2013, the entire contents of which is incorporated herein by reference to U.S. Provisional Application No. 61/818,255, titled "INSERT IMAGING DEVICE" and filed on May 1, 2013, the entire contents of which is incorporated herein by reference and to U.S. Provisional Application No. 61/818,325, titled "INSERTABLE MAGNETIC RESONANCE IMAGING COIL PROBE FOR MINIMALLY INVASIVE CORRIDOR-BASED PROCEDURES" and filed on May 1, 2013, the entire contents of which is incorporated herein by reference, and to U.S. Provisional Application No. 61/818,280, titled "SYSTEMS, DEVICES AND METHODS FOR PLANNING, IMAGING, AND GUIDANCE OF MINIMALLY INVASIVE SURGICAL PROCEDURES" and filed on May 1, 2013, the entire contents of which is incorporated herein by reference, and to U.S. Provisional Application No. 61/818,223, titled "IMAGING ASSEMBLY FOR ACCESS PORT-BASED MEDICAL PROCEDURES" and filed on May 1, 2013, the entire contents of which is incorporated herein by reference, and to U.S. Provisional Application No. 61/924,993, titled "PLANNING, NAVIGATION AND SIMULATION SYSTEMS AND METHODS FOR MINIMALLY INVASIVE THERAPY" and filed on Jan. 8, 2014, the entire contents of which is incorporated herein by reference

BACKGROUND

The present disclosure is generally related to image guided medical procedures.

In the field of surgery, imaging and imaging guidance is becoming a more significant component of clinical care, from diagnosis of disease, monitoring of the disease, planning of the surgical approach, guidance during the procedure and follow-up after the procedure is complete, or as part of a multi-faceted treatment approach.

Integration of imaging data in the surgical suite has become common-place for neurosurgery, where typically brain tumors are excised through an open craniotomy approach guided by imaging. The data that is used typically consists of CT scans with associated contrast (iodinated contrast), and MRI scans with associated contrast (gadolinium contrast). Systems provide a means to register the imaging data sets together, and registration methods to translate the three dimensional imaging space to the three dimensional space of the patient and tracking of instruments relative to the patient and the associate imaging data by way of an external hardware system such as a mechanical arm, or a radio-frequency or optical tracking device.

SUMMARY

Systems and methods are provided in which devices that are employed during a medical procedure are adaptively configured during the medical procedure, based on input or feedback that is associated with the current state, phase or context of the medical procedure. In some example embodiments, the input is obtained via the identification of one or more medical instruments present within a region of interest, and this input may be employed to determine configuration parameters for configuring the device. In other example embodiments, the input may be based on the image-based detection of a measure associated with the phase or context of the medical procedure, and this input may be employed to adaptively control the device based on the inferred context or phase of the medical procedure. In other embodiments, images from one imaging modality may be employed to adaptively switch to another imaging modality.

Accordingly, in one aspect, there is provided a computer implemented method of adaptively and intraoperatively configuring a device used during a medical procedure, the method comprising:
identifying a medical instrument during the medical procedure;
obtaining one or more customized configuration parameters for adaptively configuring the device during the medical procedure, where the customized configuration parameters are selected based on the identity of the medical instrument; and
configuring the device according to the customized configuration parameters.

In another aspect, there is provided a system for adaptively and intraoperatively configuring a device used during a medical procedure, comprising:
a data storage device comprising customized configuration parameters for adaptively configuring one or more devices during the medical procedure;
a control and processing system interfaced with the device and the data storage device, said control and processing system comprising one or more processors and memory coupled to said one or more processors, said memory storing instructions, which, when executed by said one or more processors, causes said one or more processors to perform operations comprising:

identifying a medical instrument during the medical procedure;

obtaining, from the data storage device, one or more customized configuration parameters for adaptively configuring the device during the medical procedure, where the customized configuration parameters are customized based on the identity of the medical instrument; and configuring the device according to the customized configuration parameters.

In another aspect, there is provided a computer implemented method of adaptively configuring a device used during a medical procedure, the method comprising:

obtaining one or more images of a region of interest associated with the medical procedure;

processing the one or more images to identify a context measure associated with the current state of the medical procedure;

obtaining one or more customized configuration parameters for adaptively configuring the device during the medical procedure, where the customized configuration parameters are customized based on the context measure; and configuring the device according to the customized configuration parameters.

In another aspect, there is provided a system for adaptively and intraoperatively configuring a device used during a medical procedure, comprising:

a data storage device comprising customized configuration parameters for adaptively configuring one or more devices during the medical procedure;

a control and processing system interfaced with the device and the data storage device, said control and processing system comprising one or more processors and memory coupled to said one or more processors, said memory storing instructions, which, when executed by said one or more processors, causes said one or more processors to perform operations comprising:

obtaining one or more images of a region of interest associated with the medical procedure;

processing the one or more images to identify a context measure associated with the current state of the medical procedure;

obtaining one or more customized configuration parameters for adaptively configuring the device during the medical procedure, where the customized configuration parameters are customized based on the context measure; and configuring the device according to the customized configuration parameters.

In another aspect, there is provided a computer implemented method of adaptively controlling a first imaging modality and a second imaging modality during a medical procedure, the method comprising:

while obtaining first images with the first imaging modality, intermittently obtaining one or more second images with the second imaging modality;

processing the second images to calculate, for a plurality of regions within the second images, an image measure associated with the second imaging modality; and in the event that the image measure for one or more regions is within a pre-selected range, increasing the rate of acquisition of the second images.

In another aspect, there is provided a system for adaptively controlling one or more imaging devices during a medical procedure, comprising:

a control and processing system interfaced with the one or more imaging devices, said control and processing system comprising one or more processors and memory coupled to said one or more processors, said memory storing instructions, which, when executed by said one or more processors, causes said one or more processors to perform operations comprising:

obtaining first images with a first imaging modality and intermittently obtaining one or more second images with a second imaging modality;

processing the second images to calculate, for a plurality of regions within the second images, an image measure associated with the second imaging modality; and in the event that the image measure for one or more regions is within a pre-selected range, increasing the rate of acquisition of the second images.

In another aspect, there is provided a computer implemented method of adaptively controlling one or more imaging devices during a medical procedure, the method comprising:

a) obtaining one or more first images with a first imaging modality;

b) processing the first images to calculate, for a plurality of regions within the first images, an image measure associated with the suitability of a second imaging modality;

c) in the event that the image measure for one or more regions lies within a pre-selected range, acquiring one or more second images with the second imaging modality.

In another aspect, there is provided a system for adaptively controlling a one or more imaging devices during a medical procedure, comprising:

a control and processing system interfaced with the one or more imaging devices, said control and processing system comprising one or more processors and memory coupled to said one or more processors, said memory storing instructions, which, when executed by said one or more processors, causes said one or more processors to perform operations comprising:

obtaining one or more first images with a first imaging modality;

processing the first images to calculate, for a plurality of regions within the first images, an image measure associated with the suitability of a second imaging modality;

in the event that the image measure for one or more regions lies within a pre-selected range, acquiring one or more second images with the second imaging modality.

In another aspect, there is provided a method of performing adaptive illumination while performing optical imaging during a medical procedure, the method comprising:

determining the field of view of an optical imaging device employed during the medical procedure;

determining configuration parameters of an illumination source for improving the homogeneity of illumination within the field of view;

configuring the illumination source according to the configuration parameters.

In another aspect, there is provided a system for performing adaptive illumination while performing optical imaging during a medical procedure, comprising:

a control and processing system interfaced with the optical imaging device and the illumination source, said control and processing system comprising one or more processors and memory coupled to said one or more processors, said memory storing instructions, which, when executed by said one or more processors, causes said one or more processors to perform operations comprising:

determining the field of view of an optical imaging device employed during the medical procedure;

determining configuration parameters of an illumination source for improving the homogeneity of illumination within the field of view;

configuring the illumination source according to the configuration parameters.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 5C shows a table providing example configuration data associating configuration parameters for a camera with the identity of various medical instruments.

FIG. 5D shows a table providing example configuration data associating configuration parameters for an imaging optics assembly with the identity of various medical instruments.

FIG. 5E shows a table providing example configuration data associating configuration parameters for an illuminator with the identity of various medical instruments.

FIG. 5F shows a table providing example configuration data associating configuration parameters for illuminator focusing optics with the identity of various medical instruments.

FIG. 5G shows a table providing example configuration data associating configuration parameters for a camera with a ranked list of medical instruments.

FIG. 5H shows a table providing example configuration data associating configuration parameters for a camera with the identity of various medical instruments, including configuration parameters associated with the absence of a detected medical instrument.

FIG. 5I shows a table providing example configuration data associating configuration parameters for a camera with the identity of various medical instruments, where the configuration parameters are further associated with the type of medical procedure being performed.

FIG. 5J shows a table providing example configuration data associating configuration parameters for a camera with the identity of various medical instruments, where the configuration parameters are further associated with the phase of the medical procedure.

FIG. 5K shows a table providing example configuration data associating configuration parameters for a robotic arm with the identity of various medical instruments.

FIG. 5L shows a table providing example configuration data associating configuration parameters for a user interface with the identity of various medical instruments.

FIG. 7A shows the configuration of the system prior to the identification of the access port, and FIG. 7B shows the configuration of the system after the identification of the access port.

FIG. 10A is a flow chart illustrating an example method of performing tissue identification via hyperspectral imaging.

FIG. 10B shows a table providing an example of configuration data that associates configuration parameters for illuminators with one or more tissue types.

FIG. 11A is a flow chart illustrating an example method of identifying the phase of a medical procedure based on hyperspectral imaging.

FIG. 11B shows a table providing an example of configuration data that associates configuration parameters for a camera with the phase of a medical procedure.

DETAILED DESCRIPTION

Figure 1:
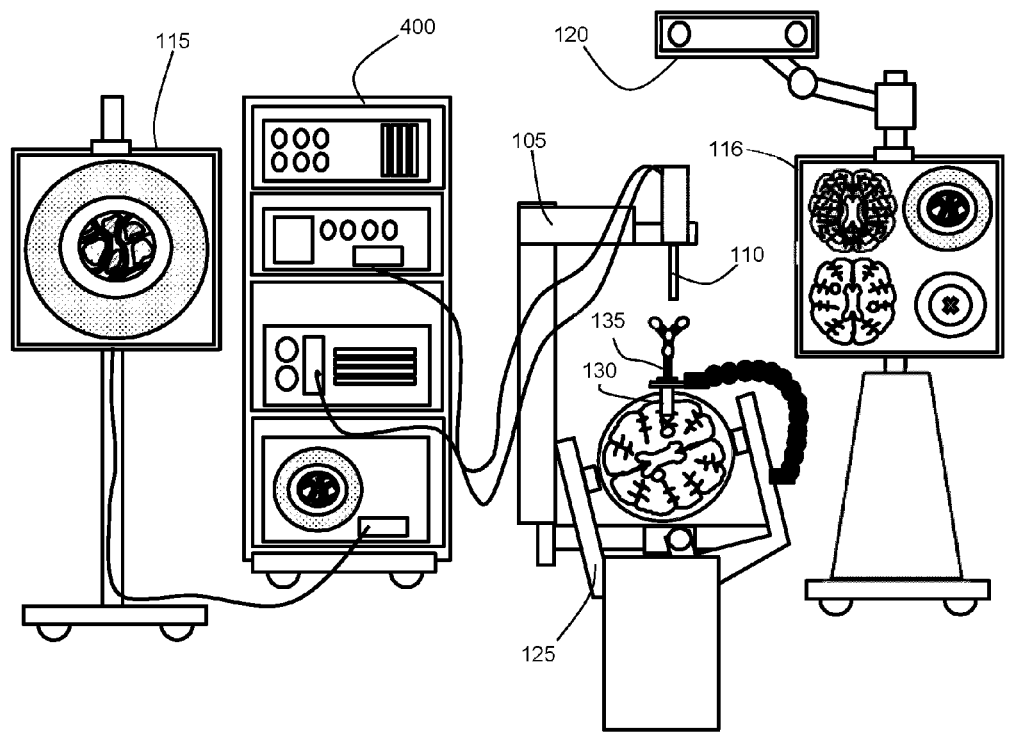
FIG. 1 illustrates an example automated system for a minimally-invasive neurological surgical procedure employing an access port.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "medical instrument" refers to a tool, instrument, or other implement employed during a medical procedure. A medical instrument may be provided in various forms, such as, but not limited to, a handheld or robotically positioned tool, or a component that is attached to, or inserted into, a patient during a surgical or medical procedure. Non-limiting examples of medical instruments include, but are not limited to, scalpels, bi-polar devices, suction devices, cutting devices, clamping devices, access ports, Imaging devices, spectroscopy devices, and suturing tools.

As used herein, the phrase "operator" refers to a user, medical practitioner, surgeon, imaging technician, or other individual or group of individuals involved in operating medical instruments, devices and equipment during a medical procedure.

As used herein, the phrase "tracking system" refers to a system configured to track the position and/or orientation of one or more objects, such as locations on a patient and/or surgical instruments. In some embodiments, the tracking system may be configured to track the position and/or orientation of an imaging device (such as an optical camera). A tracking system may also be employed to track the position and/or orientation of an access port or other component that is attached to, or inserted into, a patient or subject. In one example, a tracking system may employ a pair of infrared cameras to track the position and orientation of active or passive infrared spheres (fiducials) attached to one or more objects, such as the Polaris® system from NDI.

As used herein, the phrase "navigation system" refers to a system that processes and spatially registers pre-operative image data to an interoperative reference frame, and displays the position and orientation of one or more tracked items relative to the pre-operative image data. A navigation system may interface with, or include, a tracking system, in order to track the items. In some example implementations, hardware associated with the navigation system may include a computer system, a display, and a tracking system.

As used herein, the phrase "phase of the medical procedure" refers to a given step, or set of sequential steps, within a medical procedure. In another example, a phase of a medical procedure need not be a given step or set of sequential steps in a procedure, but may relate to the use of a specific tool or set of tools within a given step of a medical procedure.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

Presently, many devices that are employed during a medical procedure are controlled independently of the actions that are being performed during the procedure. For example, lighting systems typically operate in an independent manner without receiving any controlling input that is associated with the current phase or context of a medical procedure. In another example, external imaging devices, such as an endoscopes, are usually independently activated and controlled by an operator while a medical procedure is being performed.

Several embodiments of the present disclosure provide systems and methods in which devices that are employed during a medical procedure are adaptively and dynamically configured and/or controlled during the medical procedure, based on input or feedback that is associated with the current phase or context of the medical procedure. In some example embodiments, the input is obtained via the identification of one or more medical instruments present within a region of interest (such as a surgical field), and this input may be employed to determine configuration parameters for configuring the device. In other example embodiments, the input may be based on the image-based detection of a measure associated with the phase or context of the medical procedure, and this input may be employed to adaptively control the device based on the inferred context or phase of the medical procedure. In still other embodiments, images from one imaging modality may be employed to adaptively switch to another imaging modality. These and other example embodiments are described in detail below.

FIG. 1 illustrates an example automated system for performing various embodiments of the present disclosure, providing a non-limiting example pertaining to a minimally-invasive neurological surgical procedure employing an access port. The example automated system includes an automated robotic arm 105, which supports an optical video scope 110 (and associated illumination), video display 115 for displaying a video image from optical video scope 110, navigation display 116 for providing a navigation user interface, a tracking device 120 for tracking various medical instruments within the surgical field, and a control and processing unit 400 for controlling various devices (such as the robotic arm 105) and providing surgical navigation. A patient's head is held in place by a head holder 125, and inserted into the head is an access port 130 and introducer 135 (having fiducial markers attached thereto). Introducer 135 is shown received within access port 130 in the figure, and is tracked using tracking system 120.

The position of the patient may be initially determined and/or continuously tracked intraoperatively by tracking system 120. A set of preoperative images associated with the anatomy of interest of the patient may be obtained prior to surgery. These images may be intraoperatively registered to the patient, for example, by way of surface matching, sets of known touch points (tip of nose, temple, ears) and/or fiduciary markings that can be identified on the patient and in the associated images. These points or surfaces are registered to the tracking coordinate frame through a defined registration process. Once registered, medical instruments, and the associated patient images can be tracked in real-time, and shown in various manners on a computer monitor.

The example automated system illustrated in FIG. 1 is configured for the application of minimally invasive brain surgery, using an access port to provide a conduit within the head, allowing access to internal brain tissue for surgical, therapeutic, or diagnostic applications. The figure shows an intracranial access port which may be employed in neurological procedures in order to provide access to internal tissue pathologies, such as tumors. One example of an intracranial access port is the BrainPath surgical access port provided by NICO, which may be inserted into the brain via an obturator (introducer) with an atraumatic tip in the brain. Such an access port may be employed during a surgical procedure, by inserting the access port, via the obturator that is received within the access port to access an internal surgical site.

Figure 2:
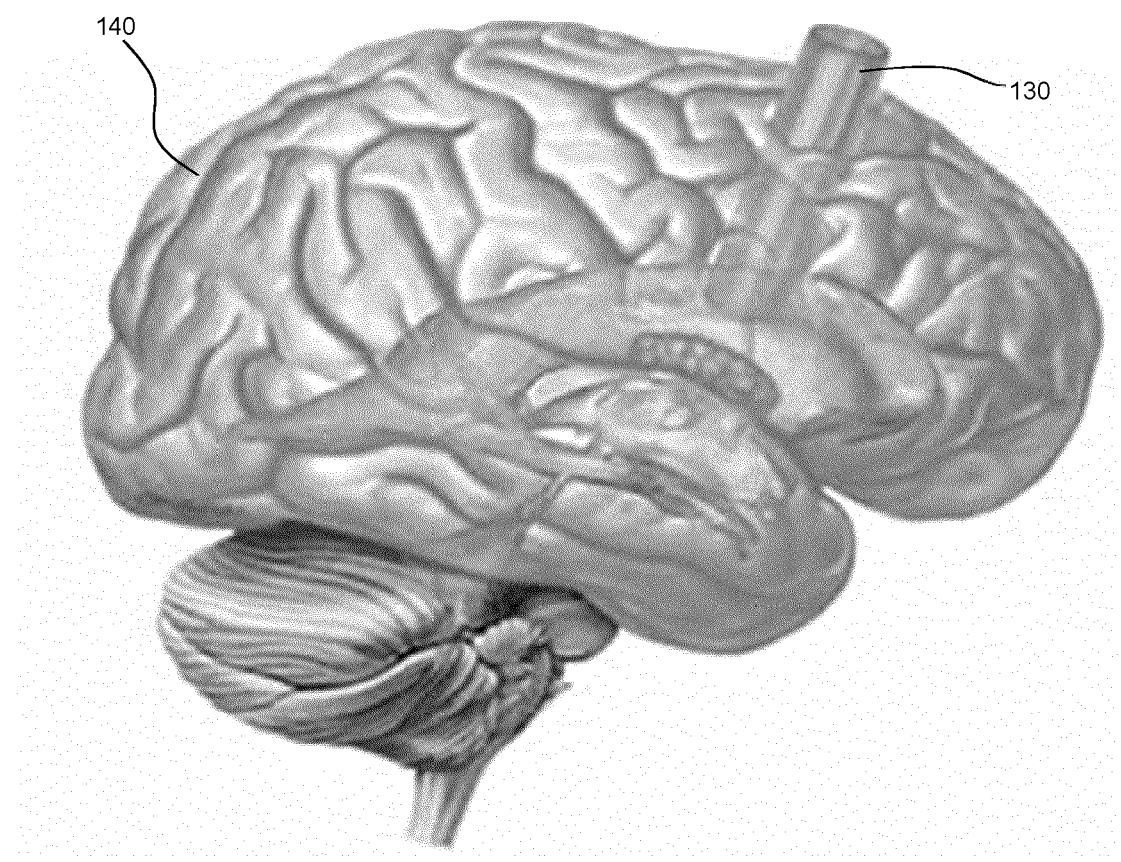
FIG. 2 shows a human brain into which an access port has been inserted, establishing an open conduit for providing access to tissue within the brain.

FIG. 2 illustrates the use of an access port, showing a human brain 140 into which an access port 130 has been inserted, thereby establishing an open conduit providing access to tissue deep within the brain. Surgical instruments may then be inserted within the lumen of the access port in order to perform surgical, diagnostic or therapeutic procedures, such as resecting tumors as necessary. This approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. For example, access port based procedures may be employed for other surgical interventions for other anatomical regions, such as, but not limited to, spine, knee and any other region of the body that will benefit from the use of an access port or small orifice to access the interior of the human body.

Referring again to FIG. 1, in order to introduce the access port 130 into the brain, introducer 135 with an atraumatic tip may be positioned within the access port and employed to position the access portion within the head. As noted above, introducer 135 (or access port 130) may include fiducials for tracking. These fiducials may be passive or active fiducials, such as reflective spheres for passive infrared detection via an optical camera, or, for example, pick-up coils in the case of an electromagnetic tracking system. The fiducials are detected by tracking system 120 and their respective positions are inferred by tracking software (which may reside within tracking system 120, or may reside, for example, within control and processing unit 400).

Once access port 130 is inserted into the brain, introducer 135 may be removed to allow for access to the tissue through the central opening of access port 130. However, once introducer 135 is removed, access port 130 can no longer be directly tracked in real time (according to the example embodiment shown in FIG. 1 in which no fiducials are attached to access port 130). In order to track the position and orientation of access port 130, it may be indirectly and intermittently tracked by a pointer tool having fiducials that are detectable by tracking system 120.

Although the example system described in FIG. 1 relates to a neurosurgical procedure, it will be understood that the systems and methods described herein are not intended to be limited to neurosurgical procedures or port-based procedures, and may be employed for a wide range of medical procedures. Examples of other types of medical procedures including orthopedic, trauma, gastrological, cardiac, gynecological, abdominal, ENT, oral and maxillofacial, urological, dental, and other surgical, diagnostic or therapeutic medical procedures. It is further noted that while many of the example embodiments described herein employ external imaging, such as imaging with an external video scope, it will be understood that various internal imaging devices, such as endoscopic or catheter imaging devices, may additionally or alternatively be employed. It is further noted that embodiments of the present disclosure may be employed within or adapted to procedures employing telesurgical or shared-control systems.

In many of the example embodiments described below, each medical instrument that is to be tracked may have a fiducial attached thereto (e.g. passive or active fiducial markers, such as reflective spheres or active LED lighting emitted from at least 3 points on a device) so that the position and orientation of the instrument can be determined. In one example implementation, the fiducial markers may be employed to determine a reference position on medical instrument (such as a central point), and an axis of the medical instrument (such as a longitudinal axis of a tool).

In some embodiments, the identification of one or more medical instruments, as described above, may be employed to adaptively or dynamically provide configuration parameters for controlling one or more devices that are employed within a medical procedure. A "configuration parameter", as used herein, refers to a parameter for adjusting the configuration of a device, as opposed to an instruction or signal that is employed to activate (turn on) the device.

This method of actively determining configuration parameters for a device is to be contrasted with methods known in the art in which a device is activated, or powered on, based on the identification of a surgical tool. Such an "activating" method is disclosed in US Patent Application Publication No. US2014/0006049 (de la Barrera et al.). One example disclosed in US2014/0006049 involves automatically activating a suction device when the suction device is identified near a surgical incision.

The present inventors have found that it is often insufficient to merely activate a device based on the identification of a tool. Specifically, the inventors have found that many devices that are employed during a medical procedure are not configured merely in a simple binary manner, and have more complex states than simply being either "on" or "off". Many devices that are employed during a medical procedure are operated according to a set of configuration parameters. Accordingly, in some example embodiments of the present disclosure, a device employed during a medical procedure may be dynamically controlled via the selection of configuration parameters that are intraoperatively determined (e.g. customized) based on the identification of a medical instrument. As noted above, in some embodiments, the medical instrument need not be tracked by the tracking system, provided that the medical instrument can be identified.

Figure 3:
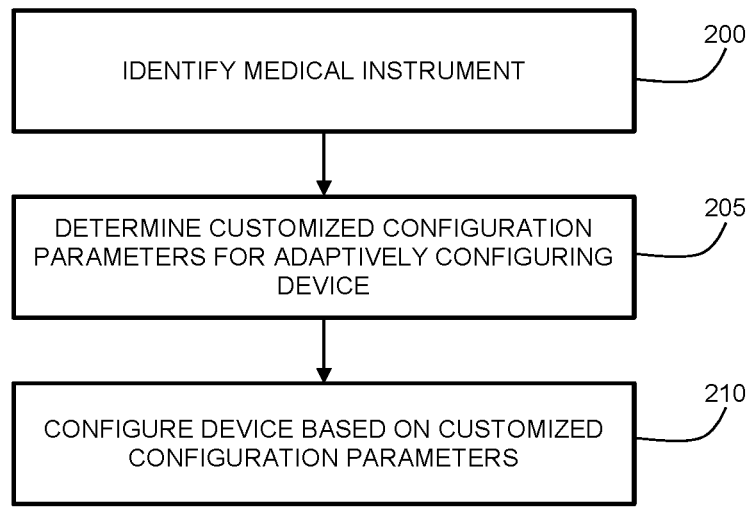
FIG. 3 is flow chart illustrating an example method of intraoperatively determining configuration parameters for a device based on the intraoperative identification of a medical instrument.

Referring now to FIG. 3, a flow chart is provided that illustrates an example method of intraoperatively determining configuration parameters for a device based on the intraoperative identification of a medical instrument. At step 200, a medical instrument is intraoperatively identified, as described below. The identity of the medical instrument is then employed to determine customized configuration parameters for adaptively and intraoperatively configuring at least one device. The configuration parameters may be obtained from pre-selected configuration data associating customized configuration parameters for one or more devices with the identities of different medical instruments. In step 210, the customized configuration parameters are employed to adaptively configure the device during the medical procedure. For example, the configuration parameters can be employed to generate suitable commands that are transmitted from control and processing unit 400 to a device, to be executed by the device firmware for reconfiguring the device.

Figure 4:
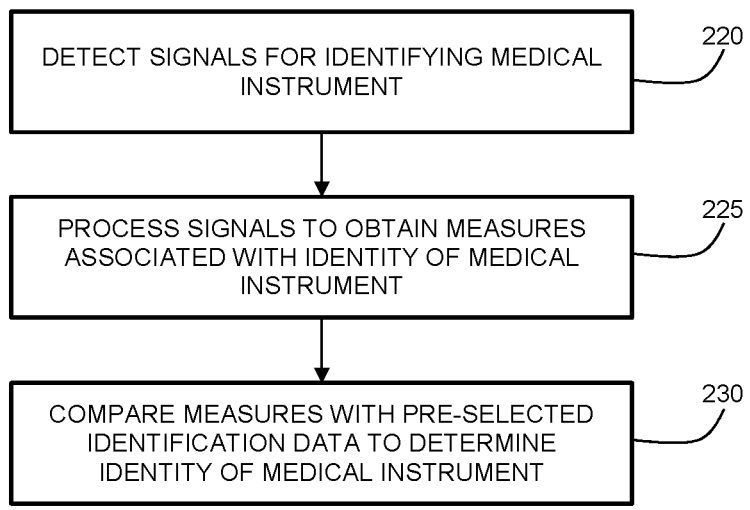
FIG. 4 is a flow chart illustrating an example method of identifying a medical instrument.

As illustrated in FIG. 4, the identification of the medical instrument may be performed, for example, as follows. In step 220, one or more signals associated with the medical instrument are detected. The signals may be, for example, images showing the medical instrument and/or fiducial markers attached to the medical instrument, optical signals emitted from markers attached to the medical instrument (e.g. pulses from an active fiducial marker), and RFID signals emitted from RFID tags attached to the medical instrument. These signals may then be processed to obtain one or more identification measures associated with the identity of the medical instrument, such as an RFID tag value, a code associated with an optical pulse sequence, as shown in step 225.

The identity of the medical instrument is then obtained, as shown in step 230, by comparing the identification measures with pre-selected identification data, where the pre-selected identification data associates the identities of a plurality of medical instruments with various measures. The identification data may be provided in the form of a database, look-up table, or other data structure that may be accessed by control and processing unit 400 to identify the medical instrument.

In one example embodiment, the identity of a medical instrument may be determined based on a unique spatial arrangement of fiducial markers attached to the medical instrument. In such a case, the detected signal may be stereoscopic images obtained by the tracking system, and the stereoscopic images may then be processed determine the positions of passive fiducial markers attached to the medical instrument. The measures associated with the identity of the medical instrument may obtained as the relative distances (and/or angles) between the fiducial markers. These measures may be compared to a look-up table that correlates the identities of different medical instruments with different relative marker distances or angles. The table entry having relative marker distances or angles that matches the calculated measures provides a determination of the identity of the medical instrument.

In another example implementation, a medical instrument may be identified based on marker geometry (e.g. using passive optical systems). For example, a medical instrument may be identified by the size and/or shape of the fiducial markers. In such a case, the identification data may correlate the geometry of the fiducial markers with the identities of various medical instruments.

In other example implementations, a medical instrument may employ active fiducials, and the characteristics of the active fiducials may be employed to identify the medical instrument. For example, active fiducials may be provided in the form of pulsed optical devices, such as light emitting diodes, where the pulsed pattern may be employed to identify a medical instrument. The associated identification data may include information, for a plurality of different medical instruments, correlating the characteristic of the active fiducials (e.g. a pulse sequence) with the identity of each medical instrument.

In another example, glyphs, barcodes, and other symbolic, graphic or textual markers may be employed to identify a medical instrument. For example, one or two-dimensional barcodes may be employed to provide detectable information identifying a medical instrument. In such a case, the identification data may correlate the graphical symbol, or a code or other information extractable from the graphical symbol, with the identities of various medical instruments.

In other example embodiments, electromagnetic and/or radiofrequency (RF) systems may be employed to identify and/or differentiate medical instruments based on an electrical trigger rather than geometry constraints. For example, a medical instrument may be identified based on radio-frequency identification (RFID) signals.

Figure 19:
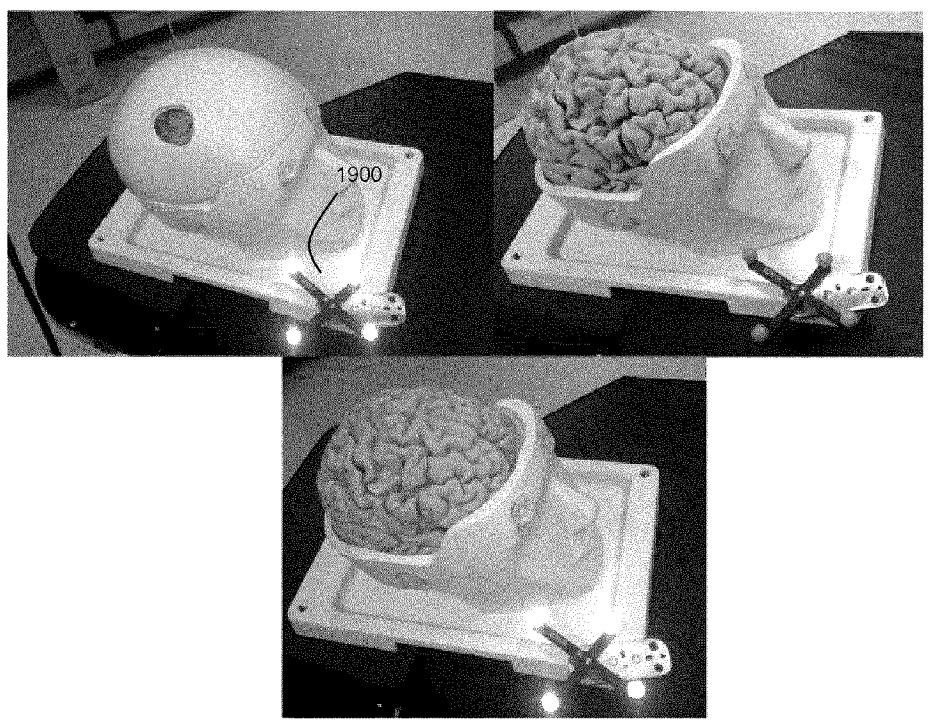
FIG. 19 is a diagram depicting a mock head, mock brain, and mock head holder of a patient with a tracking marker reference.

These tools may be tracked relative to a second set of reflective or active points, or some other known point with respect to the patient's anatomy and the tracking system (such as the tracking detector itself), which define the system reference frame. For example, a rigid piece of stainless steel (patient reference) may be rigidly attached to the Head-holder [125] and have an arrangement of passive reflective fiducial markers as shown as (1900) in FIG. 19. The tracking camera [120] will, once having identified the location of this patient reference, establish a co-ordinate system with the origin based at this patient reference (1900) and then report the position and orientation of other tools with respect to this co-ordinate system.

Although some of the preceding examples pertain to fiducial markers that are capable of performing a dual role of position/alignment sensing and instrument identification, it will be understood that these roles may be decoupled in some embodiments, such that one or more fiducial markers are provided for the tracking of a medical instrument, and one or more additional identifying markers are provided for identifying a medical instrument.

In such embodiments, the system may employ one or more additional cameras in order to image the identifying markers, and the system may include an image processing module to process the images to obtain one or more measures associated with the identity of the medical instrument. In such an embodiment, the additional cameras may be spatially registered to the reference frame of the tracking system, in order to correlate the position of an identified marker within the image with the position of medical device tracked by the tracking system, which may be performed by control and processing unit 400.

For example, in one illustrative implementation, a medical instrument may be provided with a set of passive infrared fiducial markers for tracking, and one or more two-dimensional barcodes for instrument identification. In some embodiments, two or more identifying markers may be positioned at a plurality of locations to avoid shadowing and line-of-sight issues. It will be understood, however, that unlike tracking, which requires continuous detection of fiducial markers, identification of a medical instrument need only be performed once when the medical instrument enters the region of interest or surgical field, because once a medical instrument is identified, its identity can be continuously associated with its tracked location through its unique tracking marker.

Figure 20:
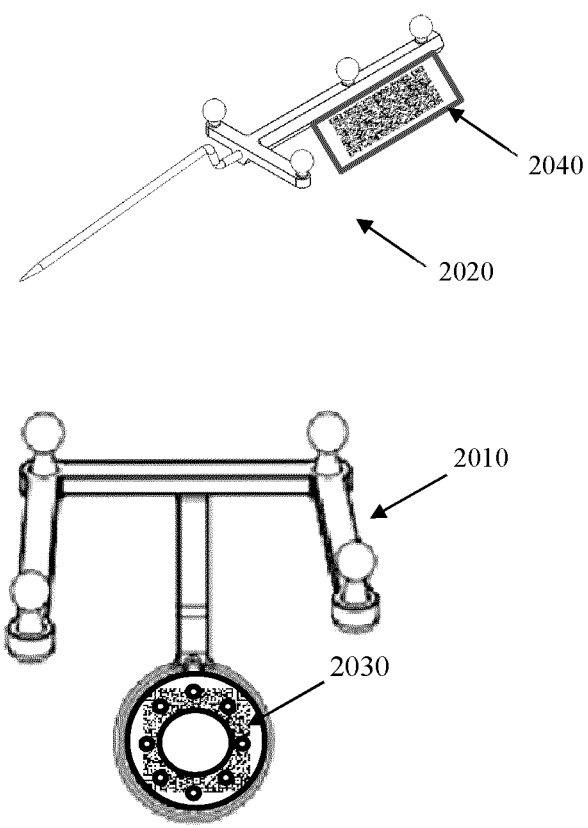
FIG. 20 is a diagram depicting medical instruments with corresponding tracking templates and optical tracking markers.

In another example embodiment, the images obtained by an additional camera may be processed to identify a medical instrument based on a known instrument shape, or based on known markings or features that may be imaged, for example the templates (2040 and 2030) located on medical instruments (2020 and 2040 respectively) as shown in FIG. 20. These templates or instrument shapes may be identified using any of the methods described in the paper [Monocular Model-Based 3D Tracking of Rigid Objects: A Survey, section 4].

Although the preceding examples disclose embodiments in which a medical instrument is both tracked and identified, it will be understood that in some embodiments, identification of a medical instrument may be performed without tracking the medical instrument. For example, some medical instruments may be employed without fiducial markers for tracking. Such non-tracked medical instruments may nonetheless be identified by any of the preceding example methods, or any other suitable identification methods. In another example implementation, a medical instrument may be identified based on input from an operator.

It will be understood that the preceding examples of devices and methods for identifying a medical instrument are provided as a non-limiting set of illustrative embodiments, and that additional or alternative devices or methods may be employed to identify a medical instrument without departing from the scope of the present disclosure.

Referring again to FIG. 3, after having identified a medical instrument in step 200, customized configuration parameters are obtained for adaptively configuring one or more devices that are employed during a medical procedure.

The one or more devices for which configuration parameters are provided may be selected from a wide variety of configurable devices that may be employed during a medical procedure. For example, a device that is adaptively configured according to the present method may be another medical instrument that is not connected or connectable to the identified medical instrument.

In another example implementation, a device for which configuration parameters are provided, based on the identification of the medical instrument, may be an auxiliary device, such as, but not limited to, an illumination device, video and sound recording devices, and imaging devices.

In one example implementation, the devices for which configuration parameters are provided may include an illumination device and/or an optical imaging device. For example, an example surgical system may include the optical imaging system, and associated control system, shown in FIG. 5A. The figure shows a subset of the components of a surgical system, and does not show some components in order to simplify the illustration (for example, a tracking system is not shown). The example system includes an optical system 250 including camera 255, imaging optics assembly 260, illuminators 265, illumination focusing optics 270, and auxiliary imaging modality assembly 275. An image detected by camera 255 is displayable on display 115, as illustrated in FIG. 1. Optical system 250 may be supported by robotic arm 105. Imaging optics assembly 260 is configured to image with a field of view as shown at 280, while illuminators 265 and illuminator focusing optics 270 project illumination beams 285 to form illumination region 290 on tissue surface 295.

With regard to illuminators 265, a wide variety of illuminator types may be employed to provide intraoperative illumination. Examples of different types of illumination include a monochromatic or narrow band light source or laser source, a broadband source (such as a white light source) optionally having a spectrally selective element such as an optical filter, a projector type source (which may optionally be employed for surgical guidance or for projecting customized light patterns onto the surgical field), a polarized light source implemented by polarizing filters, structured light projectors, photo-acoustic excitation lasers, ablation lasers, and therapeutic light sources used for photo-activation of therapeutic solutions. Illumination light can be locally generated as shown in the figure, or optionally externally generated and directed to optical system 250 using an optical conduit such as a fiber optic bundle, a light pipe, or free space delivery. The illumination may be broad to fill the entire surgical field of view (e.g. at the end of an access port), or focused on a particular point. Each of these light delivery devices can be controlled by control and processing unit 400.

Figure 5A:
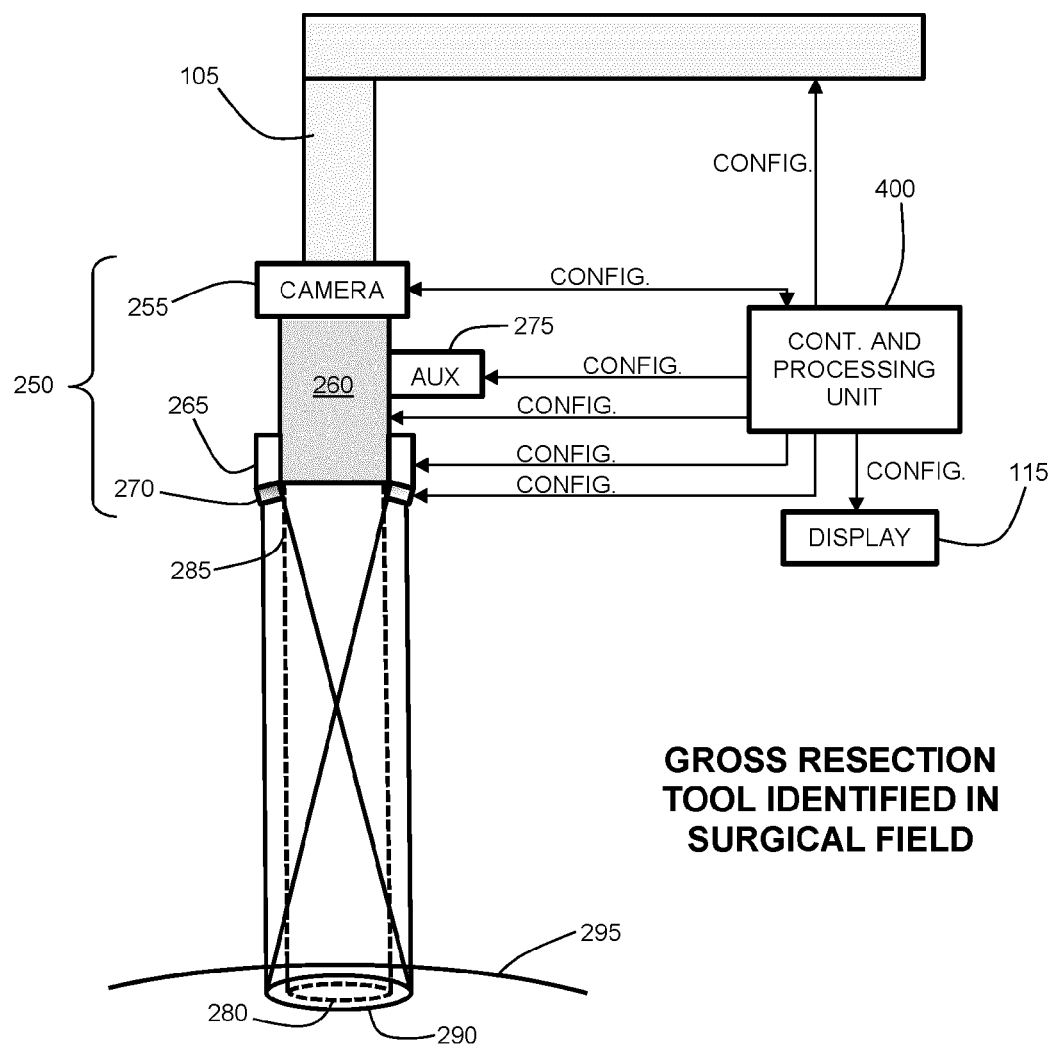
FIG. 5A illustrates an example surgical system including an optical imaging system and associated control system, where one or more components of the optical system are adaptively configured based on the identification of a medical instrument.

As shown in FIG. 5A, control and processing unit 400 may be interfaced with one or more components of optical system 250 in order to dynamically provide configuration parameters based on the intraoperative identification of one or more medical instruments. Control and processing unit 400 is shown interfaced with camera 255, imaging optics assembly 260, illuminators 265, illumination focusing optics 270, and auxiliary imaging modality assembly 275. Upon detection of a medical instrument, the configuration data may be accessed in order to determine customized configuration parameters for one or more components of the optical system, and the customized configuration parameters may be employed to configure or reconfigure the one or more components.

In the example case illustrated in FIG. 5A, a coarse resection tool (not shown in the figure) has been identified. Customized configuration parameters are obtained for customizing one or more of camera 255, imaging optics assembly 260, illuminators 265, illumination focusing optics 270, auxiliary imaging modality assembly 275, robotic arm 105, and a user interface displayed on display 115, based on the identification of the coarse resection tool.

Figure 5B:
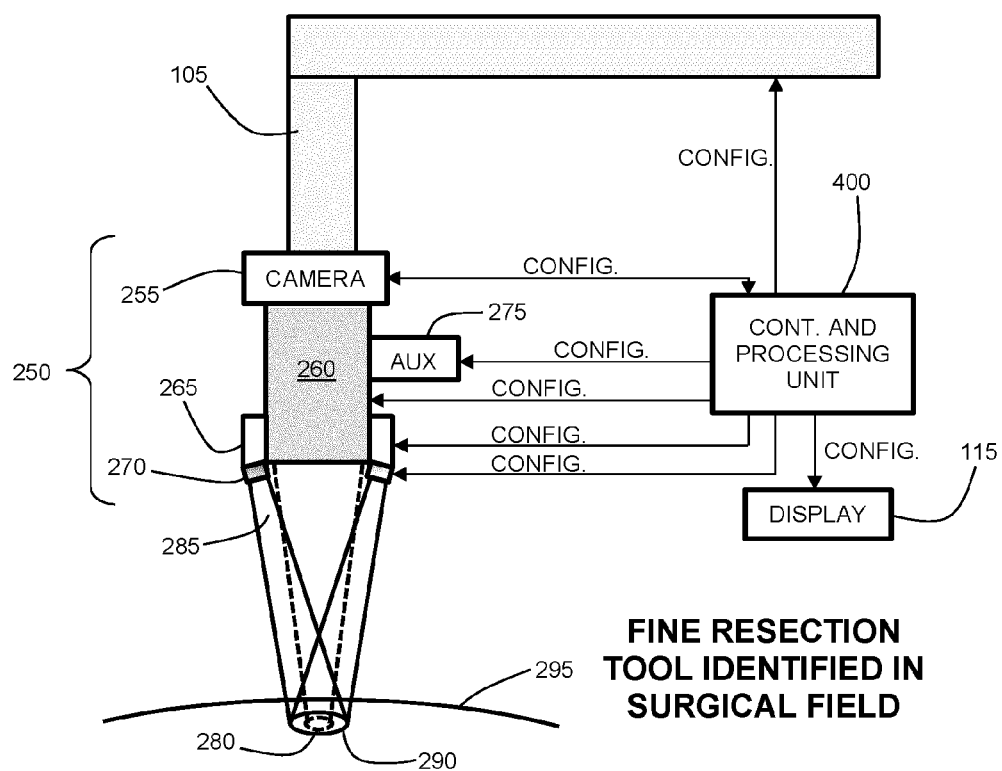
FIG. 5B shows the re-configuration of the system shown in FIG. 5A after the identification of a different medical instrument within the surgical field.

When the coarse resection tool is removed from the surgical field and a fine resection tool is brought within the surgical field, the absence of the gross section tool and the presence of the fine resection tool is detected, with the fine resection tool being identified by the system as described above. New customized configuration parameters are obtained, and the optical system 250 is reconfigured as shown in FIG. 5B. In the example case shown in the figure, configuration parameters for a number of components have been modified due to the identification of the fine resection device. Specifically, robotic arm 105 has been repositioned according to updated configuration parameters to achieve a reduced working distance; imaging optics assembly has been reconfigured to provide a reduced field of view 280 and therefore higher magnification; illumination focusing optics 270 have been reconfigured to produce a reduced illumination region; and illuminators 265 have been reduced in intensity in order to preserve the intensity of illumination within the illumination region 290.

Additionally, for example, the system may be further reconfigured by providing configuration parameters for any one or more of room lights (e.g. dimming or increasing brightness), coarse resection tool reconfiguration, fine resection tool reconfiguration, adjustment of speed and/or power of the fine resection tool, modifying hanging protocols displayed on the navigation screen (e.g. display different sets of images and different views of those images), and adjust the angle or height of the surgical table.

In one embodiment, fine resection tool is tracked by tracking system 120, and the customized configuration parameters configure robotic arm 105 to be actuated such that the field of view 280 of imaging optics assembly 260 is actively translated to overlap with the distal tip of the fine resection device based on closed-loop feedback from tracking system 120.

In one example implementation, control and processing unit 400 may be interfaced with camera 255 in order to adaptively provide configuration parameters associated with one or more of, but not limited to, imaging frame rate, gain, saturation, shutter speed, ISO, aperture size, on-chip binning, image size, digital zoom (ROI), and cooling temperature (e.g. if thermo-electric cooling is available). An example of configuration data that associates configuration parameters for camera 255 with one or more medical instruments is shown in FIG. 5C.

Control and processing unit 400 may additionally or alternatively be interfaced with imaging optics assembly 260 in order to provide configuration parameters associated with one or more of, but not limited to, zoom (magnification), focal length, working distance, numerical aperture, polarization sensitivity, attenuation, filter wavelength, depth of field, image stabilization and field of view. For example, imaging optics assembly 260 may include one or more actuators for varying these settings according to the configuration parameters that are provided. An example of configuration data that associates configuration parameters for imaging optics assembly 260 with one or more medical instruments is shown in FIG. 5D.

Control and processing unit 400 may additionally or alternatively be interfaced with illuminators 265 in order to provide configuration parameters associated with one or more of, but not limited to, illumination intensity, illumination wavelength, illumination angle, pulsed or continuous operation, and number of active illuminators. For example, illuminators 265 may include one or more actuators for varying the incidence angle of the illumination beams according to the configuration parameters that are provided. An example of configuration data that associates configuration parameters for illuminators 265 with one or more medical instruments is shown in FIG. 5E.

Control and processing unit 400 may additionally or alternatively be interfaced with illumination focusing optics 270 in order to provide configuration parameters associated with one or more of, but not limited to, focal length, depth of field, illumination spot size, beam shape, working distance, polarization, filter wavelength, and attenuation. For example illumination focusing optics 270 may include one or more actuators for varying these settings according to the configuration parameters that are provided. An example of configuration data that associates configuration parameters for illumination focusing optics 270 with one or more medical instruments is shown in FIG. 5F.

Control and processing unit 400 may additionally or alternatively be interfaced with auxiliary imaging modality assembly 275. For example, auxiliary imaging modality assembly 275 may include one or more optical ports, and a mechanism, such as an optical deflection device (e.g. a mirror, prism, reflector, filter, pellicle, window, or optical pick-off) that may be selective actuated to deflect the beam path along the port axis, thereby directing the optical beam to imaging and/or source optics associated with another imaging modality. For example, in one example implementation, auxiliary imaging modality assembly 275 may include one or more ports for selectively employing an additional imaging modality including, but not limited to, fluorescence imaging, infrared imaging, ultraviolet imaging, hyperspectral imaging, optical coherence tomography, polarization-sensitive optical coherence tomography, polarization-sensitive imaging, thermal imaging, photo-acoustic imaging, and Raman imaging. Control and processing unit 400 may thus provide one or more configuration parameters for selectively configuring the imaging system to employ one or more additional or alternative imaging modalities. Control and processing unit 400 may also provide one or more configuration parameters for selectively configuring the one or more additional or alternative imaging modalities.

In some embodiments, one or more external imaging devices may be employed for multi-modal imaging. For example, multi-modal imaging may be achieved by way of either direct optical imaging, or using the system to hold additional imaging probes, such as MRI, US, PET or X-ray (either in transmit or receive modes). In some embodiments, the turret of robotic arm 105 can be actuated during the procedure to engage different modalities, as described above, much in the way multiple tools are selected in a CNC machining system. In other embodiments, multiple modalities other than optical, for instance ultrasound, MRI, OCT, PET, CT, can be supported by or otherwise interfaced with the automated arm, optionally in addition to one or more optical imaging/detection modalities.

In the case of photo-acoustic imaging, laser light is used to excite the tissue, while an ultrasound array positioned in the access port is employed to collect the emitted ultrasound signal. In addition, different wavelengths or spectral bands of light may be utilized. For instance, Raman imaging can be used to investigate the chemical composition of tissue at a specific location of interest, i.e. point source imaging. Hyper-spectral imaging can be accomplished by scanning a detector across the region of interest, or collecting a multi-spectral detector images at a selected location. In one example implementation, the hyperspectral image could be overlaid on video images to provide different perspectives of exposed tissue regions. In another example embodiment, laser light delivered by an optical device supported by the automated arm may be employed for the alignment and/or excitation of photo-reactive therapeutics. Any or all of the optical imaging modes employed by a given system embodiment may be accommodated by a fiber-optic delivery and receiving bundle that is attached to the turret of robotic arm 105. Alternatively, or in addition, various ports or light guides may be used to co-align the light delivery or reception.

In an alternate embodiment, optical system 250 can have different acquisition modes. Some modes are listed as follows but are not limiting to additional modes not listed here. In one mode, images can be acquired by sweeping through the different image acquisition modes to provide multiple serially obtained (e.g. almost simultaneously obtained) images of different types which can be combined into an overlaid representation and displayed to the operator. The multi modal shifting can be achieved, for example, by using a filter wheel on the optical system, allowing the imaging modalities to change as the wheel is turned. It can also be achieved through beam splitting using optical lenses and directing the beams to different imaging devices.

Although several different components are shown interfaced with control and processing unit 400 in the figure, it is to be understood that control and processing unit 400 may be interfaced with any component, or any combination of components, and with other components that are not shown.

In an alternate embodiment, the optical system 250, under control of control and processing system 400, may automatically perform actions such as, but not limited to, auto-focus of the optical view and auto adjustment of the illumination system for optimal viewing illumination, optimal tissue differentiation, and optimal modal detection. Optical system 250 can achieve these automatic functions through analysis of the various images acquired by the system, such as the optical camera image or others by control and processing system 400. The images can be analyzed for metrics such as white balance, contrast, and saturation. The metrics can then be processed based on the type of view required, for example when illuminating for tissue differentiation the imaging processing method should employ the constraints of the system (geometric, intensity range, etc.) to obtain the illumination intensity and wavelengths which would provide a suitable (e.g. maximal) contrast metric. Other image analysis that could be done include image sharpness determination and optimization by analyzing specific focal zones. Alternatively, the optical system 250 could adjust zoom and focus by calculating the working distance between the camera 255 and the surgical area of interest by using position and orientation of the surgical tool and position and orientation of the optical system provided by the navigation system. In the case of port-based surgery, the port could be tracked and the zoom and focus be set based on the working distance between the camera and bottom of the port. In both of these cases, a lookup table could be created that relates working distance to a set of camera parameters: zoom, focus, aperture, and iris. This relationship could be determined empirically or analytically.

The preceding examples illustrate embodiments in which configuration parameters are provided in a number of data structures pertaining to different devices that may be intraoperatively configured based on the identification of one or more medical instruments. It will be understood that the data structures were illustrated separately for heuristic purposes, and that in other implementations, the two or more data structures may be combined. For example, a composite data structure may be formed in which different devices are provided as different columns.

As shown in FIGS. 5C-5F, configuration parameters may be provided for intraoperatively configuring a device based on the identification of a single medical instrument, or based on the identification of multiple medical instruments. The example data structures shown in FIGS. 5C-5F illustrate an example implementation in which configuration parameters are provided for each relevant combination of identified medical devices.

In another example implementations, configuration parameters can be provided for multiple identified medical instruments according to a ranked or prioritized list of medical instruments. For example, FIG. 5G provides an example implementation of a data structure in which configuration parameters are provided for camera 255 on a unique basis for each medical instrument that may be identified. Control and processing unit 400 may be programmed to interpret the data structure in a ranked configuration. If a single medical instrument is identified, in the absence of other medical instruments, then the configuration parameter set associated with the single medical instrument is employed to configure camera 255. For example, if only instrument 4 is identified at any given time during a medical procedure, in the absence of instruments 1-3, 5 and 6, then configuration parameter set 4 is employed to configure camera 255.

However, if two or more medical instruments are intraoperatively identified, then configuration parameters associated with the highest ranked medical instrument are employed. For example, if medical instruments 3 and 5 are identified at a given time during a medical procedure, the configuration parameters used to configure camera 255 would be configuration parameter set 3, since medical instrument 3 outranks medical instrument 5. It will be understood that the specific implementation illustrated in FIG. 5G is merely one example implementation, and that variants of this embodiment may be performed without departing from the scope of the present disclosure. For example, weighting factors or coefficients may be employed to realize a related ranked or prioritized embodiment.

Although the preceding example implementations illustrate cases in which configuration parameters are provided based on the identification of one or more medical instruments, it will be understood that the configuration data may include a default set of configuration parameters that may be employed to configure the device when the identifiable medical instruments are not present, as shown in FIG. 5H. For example, this may be useful for ensuring that a given device reverts to a default configuration when one or more identified medical instruments are removed from the surgical field or region of interest.

The example embodiments shown in FIGS. 5C-5H relate the identification of a medical instrument, by its name or type (e.g. by its clinical, medical, or conventional name), with customized configuration parameters for adaptively and intraoperatively configuring a device (e.g. camera 255). It is to be understood that the identification of an instrument by name or type is but one example implementation of an identification method, and that many other methods may be employed to identify a medical instrument. For example, a medical instrument may be indirectly identified with a textual, numeric, symbolic, or alphanumeric instrument identifier that is associated with its identity. In such an embodiment, configuration data would include data elements associating one or more instrument identifiers with customized configuration parameters, where the instrument identifier initially be obtained from the pre-selected identification data, as described above.

In some embodiments, the medical instrument may be identified beyond its name or type. For example, in one embodiment, the instrument may be uniquely identified. In other words, a resection device would not simply be identified as a generic "resection device", but would be identified with a unique identifier that is only associated with the specific instrument that is used, such as an instrument identifier that includes a serial or inventory number associated with the resection device.

In one example implementation, a medical instrument may be identified as being associated with a specific operator. For example, a medical instrument may be commonly associated with a specific surgeon, and the instrument identifier may include identifying information associating the medical instrument with the specific surgeon. In such an embodiment, the configuration data would correlate the instrument identifier with configuration parameters that are preferred by the specific surgeon, such that when the specific medical instrument is used and identified, control and processing unit 400 provides the preferred configuration parameters to the relevant medical device or devices. In one embodiment, biometric sensors may identify the user of the device. The biometric sensors may be integrated into the surgical tool or acquired via a separate device either attached to the surgeon continuously or separate (e.g. the surgeon activates his/her identity at a computer console). Example biometric identification techniques are: iris scan, fingerprint scan, voice identification, and cardiac patterns.

In one example implementation, the configuration data that is used to associate the identity of one or more medical devices with customized configuration parameters (for the interoperative configuration of one or more devices) may depend on the location of the automated system. For example, a given medical instrument may be used in two different operating rooms, each room having a separate automated system, where the two operating rooms are employed for performing different medical procedures. In such a case, the configuration data employed by one automated system may be different than the configuration data employed by the other automated system, such that the same medical instrument may be employed in either room, but where different configuration parameters are associated with the medical instrument in each room.

In another example implementation, the configuration data that is used to associate the identity of one or more medical devices with customized configuration parameters may be further associated with a medical procedure. Such an embodiment is illustrated in FIG. 5I, where an additional column is shown that further associates the configuration parameters with a given medical procedure. According to this example embodiment, upon identification of a medical instrument, control and processing unit 400, which select the appropriate customized configuration parameters for intraoperatively configuring one or more devices based on both the identity of the medical instrument and the procedure that is begin performed. Control and processing unit 400 would, in this example embodiment, obtain information identifying the procedure being performed based on operator input, automated detection (described in detail below), or based on pre-programmed information.

In another example implementation, the configuration data that is used to associate the identity of one or more medical devices with customized configuration parameters may be further associated with a given step or phase of a medical procedure. Such an embodiment is illustrated in FIG. 5J, where an additional column is shown that further associates the configuration parameters with a given phase of a medical procedure. According to this example embodiment, upon identification of a medical instrument, control and processing unit 400, which select the appropriate customized configuration parameters for intraoperatively configuring one or more devices based on both the identity of the medical instrument and the procedure that is begin performed. Control and processing unit 400 would, in this embodiment, obtain information identifying the phase of the procedure being performed based on operator input, automated detection (described in detail below), or based on pre-programmed information.

The preceding example embodiments pertaining to the configuration of devices based on the identification of one or more medical instruments were illustrated within the context of device components associated with an optical system. In one another example implementation, the device for which configuration parameters are provided may be a robotic arm that is employed to position one or more tools or devices, as illustrated in FIG. 5K. Examples of configuration parameters for configuring a robotic arm include, but not limited to, positions and orientations of the arm, motor speeds, safety regions for collision avoidance, stiffness, and home positions, tip speeds, acceleration profiles, working distance offset, position of the arm with respect to the surgeon, updated voice command library if the robot is controlled via voice commands, updated mapping of robot control pedals/buttons, enable/disable of automatic tracking modes, thresholds used to trigger automatic movement/alignment of the robot, safety delay time, movement patterns, the payload weight will require the arm to compensate accordingly to the new weight, movement for various types of lighting, surgical phase.

In another example implementation, the device for which configuration parameters are provided may be a computer-controlled user interface, as shown in FIG. 5K. For example, as shown in FIG. 5A, display 115 may provide a user interface, such as a user interface associated with the output from optical system 250, and/or navigation. One or more input devices may be employed to allow an operator to interact with the user interface, and examples are provided below. The configuration parameters that are associated with the one or more medical instruments may enable the automated re-configuration of the user interface based on the identification of one or more medical instruments. Examples of configuration parameters for configuring a user interface include, but not limited to, displayed windows, displayed icons, colors, one or more displayed or displayable menu items, intensity of one or more displayed items, relative size of displayed windows, relative positioning of one or more windows, display of images from one or more imaging modalities, selection of imaging modalities for overlay of images from two or more imaging modalities, and messages or warnings for the operator, selection of which tracked tool is used to control the view of imaging data, background music selection, default display options (e.g. are augmented graphics displayed), user interface skin/theme, mapping of control buttons, various data display or analysis options related to particular imaging modalities, and alerts corresponding to identification of particular spectral information related to identification of potential unhealthy tissues.

Figure 6A:
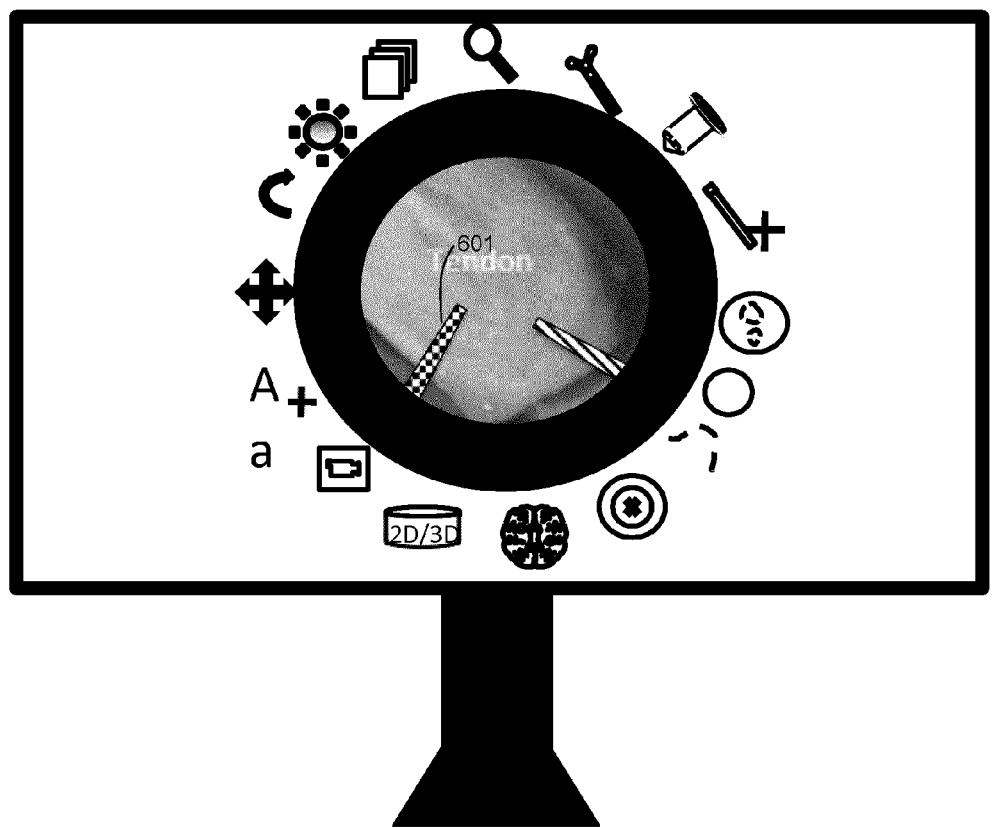
FIG. 6A shows an example user interface prior to the identification of a medical instrument.
Figure 6B:
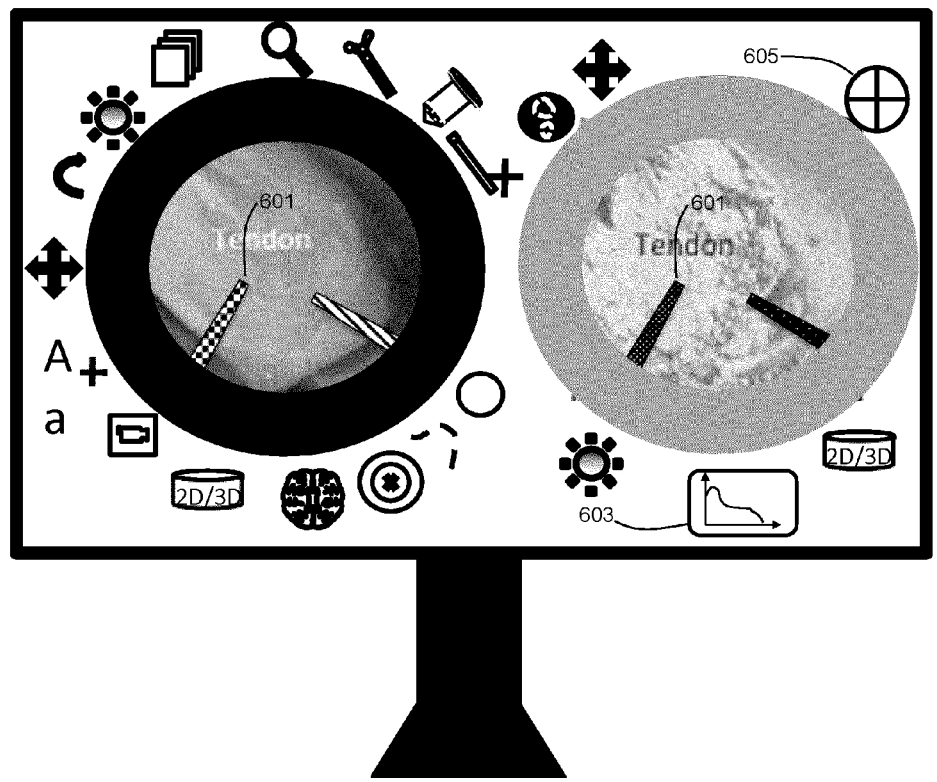
FIG. 6B shows the reconfiguration of the example user interface from FIG. 6A, after the identification of a medical instrument.

FIGS. 6A and 6B illustrate an example implementation of a user interface that is automatically configurable based on the identification of one or more medical instruments. FIG. 6A shows the user interface prior to the detection of the medical instrument (fine resection tool) 601, while FIG. 6B shows the user interface after the detection of the medical instrument 601. In the latter case, control and processing unit 400, having identified the medical instrument, has determined, based on the configuration data, configuration parameters for reconfiguring the user interface. After the identification of the fine resection tool the system has switched to hyperspectral mode providing images for better tissue differentiation. Accordingly the GUI has adapted to this multimodal imaging by displaying both the visible and hyperspectral imaging simultaneously side by side as opposed to just the single view depicted in FIG. 6A. The adapted GUI also provides additional control buttons specific to this multimodal display with hyperspectral imaging. For example button 603 which would allow the user to view a hyperspectral spectrum at a specific point on the display of the hyperspectral image if the user chose to do so. Another example is alert 605 which changes colour if a particular spectral fingerprint is identified in the hyperspectral image which is related to an unhealthy tissue type for example a tumor tissue spectral fingerprint.

It is further noted that customized configuration parameters may be pre-selected prior to the commencement of the medical procedure, or may alternatively be provided, or modified, during the medical procedure. For example, a user interface may be provided to facilitate input or modification of configuration data and/or identification data via a suitable input device. Examples of input devices are provided below. The user interface may also be provided to optionally override one or more configuration parameters.

Figure 7A:
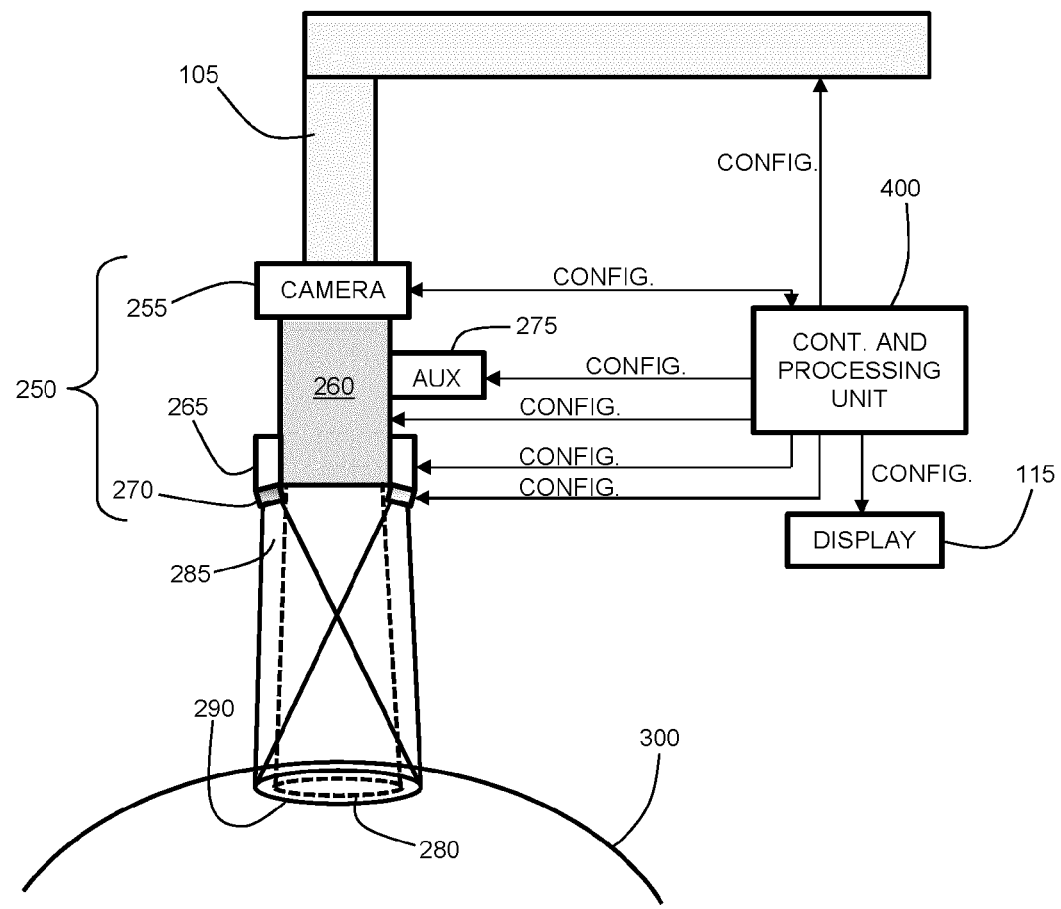
FIGS. 7A and 7B illustrate an example embodiment in which new configuration parameters are provided for intraoperatively changing the configuration of an optical system when an access port is identified, where
Figure 7B:
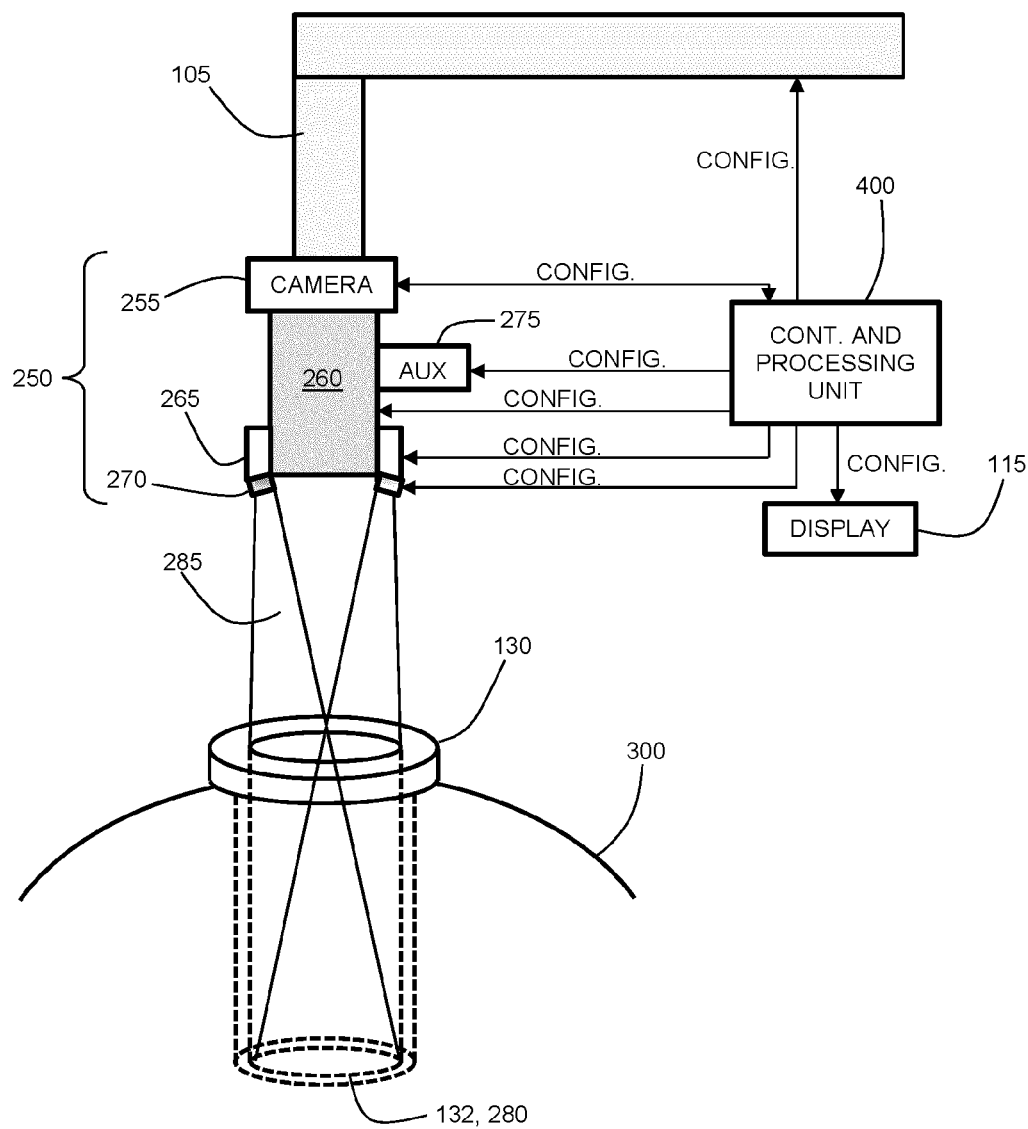

FIGS. 7A and 7B illustrate an example embodiment in which control and processing unit 400 is employed to provide new configuration parameters for intraoperatively changing the configuration of optical system 250 when an access port is identified. In FIG. 7A, optical assembly 250 is shown in a configuration to image the top portion of a patient's skull 300. This initial configuration may be determined based on configuration parameters obtained based on the identification of one or more medical instruments employed for performing a craniotomy (not shown in the figure), such as a craniotomy drill used specifically for removing a section of the skull for surgical access to the brain, or a scalpel used to access the skull through the skin.

For example, configuration parameters may be provided that stipulate the diameter of illumination spot 290, and the field of view 280 provided by imaging optics assembly 260. Additional configuration parameters may be provided to specify a pre-selected working distance between the distal portion of imaging optics assembly 260 and the surface of skull 300, and these additional configuration parameters may be employed to move robotic arm 105 to a suitable position for performing the craniotomy while imaging. In such cases, both optical system 250 and the patient's head 300 may be spatially referenced to enable the relative positioning of optical system 250. Further examples of configuration parameters that may be obtained based on the identification of the medical instruments include configuration parameters that specify a suitable illumination intensity, spectral profile, colour, or wavelength. As noted above, the identification of the medical instruments for performing the craniotomy may also be employed to reconfigure the user interface displayed on display 115.

In the example neurological procedure presently considered, a surgical access port is inserted into the brain after having performed the craniotomy, as described above. FIG. 7B shows access port 130 inserted into the patient's head, where distal internal surface 132 of access port 130 (or the distal aperture of the access port, depending on the type of access port that is used) is recessed deep within the brain, providing surgical, diagnostic, and/or therapeutic access to brain internal tissue. Control and processing unit 400 identifies access port 130, which may be performed, for example, in an automated fashion based on fiducial markers or other identifying indicia attached to access port 130, in an automated fashion via image processing of an image of the surgical field, or via input from an operator indicating that access port 130 has been employed.

The configuration data is then processed to obtain configuration parameters that are customized based on the presence of access port 130 within the surgical field, and the customized configuration parameters are employed to reconfigure one or more components of optical system 250. For example, as shown in FIG. 7B, the angle and/or angular width of illumination beams 285 are modified such that the distal inner surface or aperture 132 of access port 130 is illuminated, and the working distance and field of view of imaging optics assembly 260 are modified for imaging of the distal surface or aperture 132 of access port 130. Further examples of configuration parameters that may be obtained based on the identification of the medical instruments include configuration parameters that specify a suitable illumination intensity, spectral profile, colour, or wavelength for performing one or more port-based procedures. The identification of access port 130 may also be employed to reconfigure the user interface displayed on display 115. It is noted that the configuration of the optical system may be further modified by the introduction into the surgical field of one or more medical instruments having customized configuration parameters associated therewith.

In some embodiments, the customized configuration parameters associated with the presence of access port 130 may be employed to provide the delivery of homogenized light through the port to the surgical area of interest, thereby potentially permitting improved tissue differentiation between healthy and unhealthy brain tissue by potentially reducing glare and reducing shadows which fall on the tissue due to ports. For example, configuration parameters may be provided, on a continuous basis while access port 130 is detected within the surgical field, to actively control the position of robotic arm 105 such that coaxial alignment between the axis of imaging optics assembly 260 and access port 130 is maintained. These configuration parameters may be computed dynamically by control and processing unit 400 based on real-time tracking of the orientation of access port 130 via tracking system 120.

In one example embodiment, configuration parameters associated with the orientation of optical system 250 may be computed in order to achieve a desired level of homogeneity of illumination intensity for illumination within access port 130. For example, optical modelling, such as non-sequential ray-tracing, may be employed to calculate, for a given set of optical focusing conditions, a working distance for the illuminators that provides a suitable, or optimal, level of illumination homogeneity. The modelling may include both the angular intensity distribution of the source, and also the optical properties of access port 130, such that reflections from the port walls may be modelled.

Figure 7C:
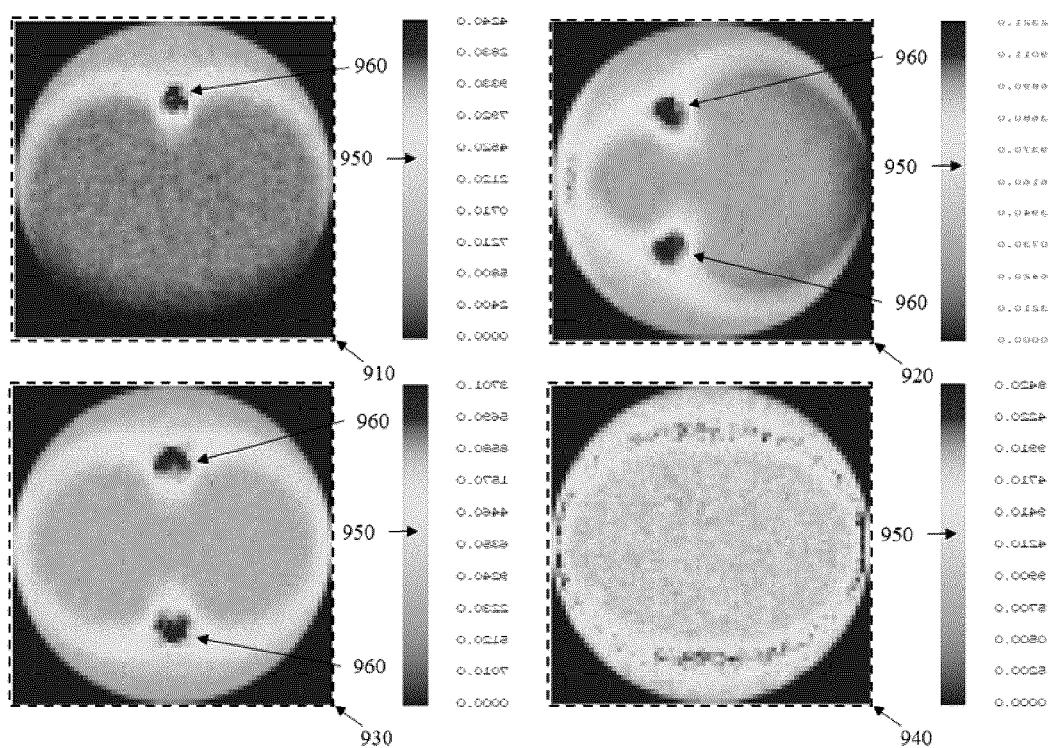
FIG. 7C demonstrates an example implementation of the use of ray tracing to calculate a configuration parameter specifying the working distance of the illuminators in order to achieve a pre-selected level of illumination homogeneity.

FIG. 7C demonstrates an example implementation of the use of ray tracing to calculate a configuration parameter specifying the working distance of the illuminators in order to achieve a pre-selected level of illumination homogeneity. Non-sequential ray tracing software (ZEMAX) was employed to model the illumination intensity distribution at the distal surface 132 within access port 130, based on the optical properties of access port 130 as well as properties of illuminators 265.

Illumination intensity distributions were computed based on four different models, each having a different illuminator configuration. The first model (910) shows the illumination of the region of interest at the distal end of an access port 130 using a single illuminator at a distance of 35 cm from the bottom of the access port 130 and offset 16.5 mm from the central axis of the access port 130.

The second (920) and third (930) models show illumination of the region of interest using illumination from two illuminators each. The pairs of sources in each model are oriented differently with respect to the other model. Both models two and three have the same distance and pose parameters as model one relative to the port, 35 cm distance from the bottom of the port and each illuminator offset 16.5 mm from the central axis of the access port 130.

The final model (940) shows illumination from two sources with the same orientation as the sources in the second model (920) relative to the external imaging sensor, with the same pose but, a working distance of 65 cm. The intensity map on each region of interest (distal end of the port) shown in the figure describes the illumination level, where mid-range (950) represents the ideal illumination level. As can be seen in FIG. 7C, hot spots (960) exist in models one through three (910, 920, 930) which result in heavy glare at those positions and inadequate imaging for the surgeon, while model four (940) provides the optimal lighting condition (homogenized and low glare delivery of illumination). Using model four as the optimal pose alignment, the automated mechanical arm would position the scope to achieve this particular illumination thereby improving the operating view of the surgeon. The software can then determine a suitable spatial position and pose of the illumination source relative to the target (e.g. the access port) given the restrictions of the system to ensure optimal light delivery through the port to the region of interest.

The illumination source may be also optimally positioned after modelling the shadow cast by the surgical tools. In other words, the target region within the field of view may be optimally illuminated while avoiding casting of shadows from the surgical tools. This is possible given the three-dimensional pose of the surgical tools can be estimated using fiducial tracking markers placed on the surgical tools.

Figure 8:
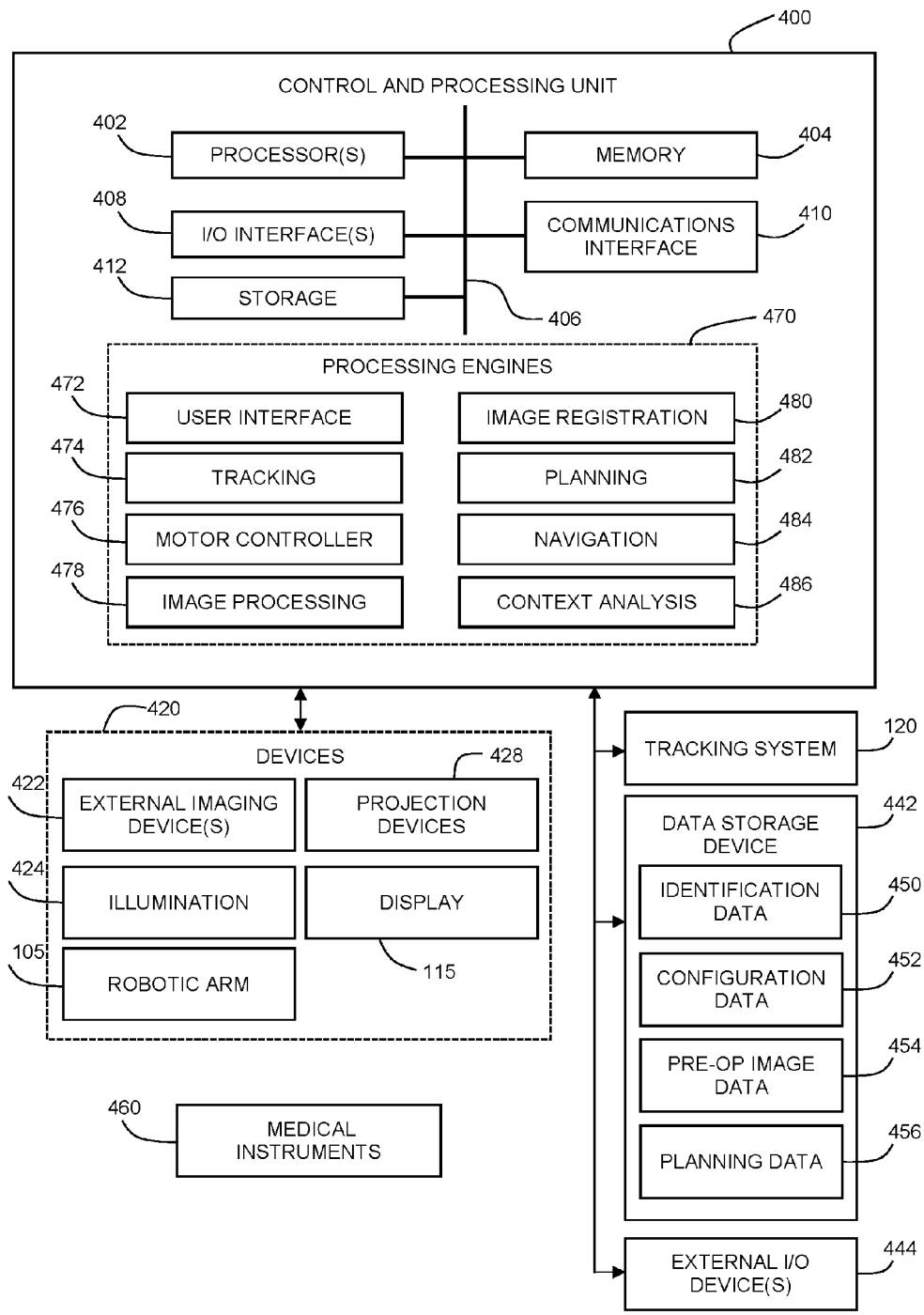
FIG. 8 shows a block diagram of an example system configuration, including the control and processing unit and a number of external components.

Referring now to FIG. 8, a block diagram of an example system configuration is shown. The example system includes control and processing unit 400 and a number of external components, shown below.

As shown in FIG. 8, in one embodiment, control and processing unit 400 may include one or more processors 402, a memory 404, a system bus 406, one or more input/output interfaces 408, and a communications interface 410, and storage device 412.

Control and processing unit 400 is interfaced with other external devices, such as tracking system 120, data storage 442, and external user input and output devices 444, which may include, for example, one or more of a display, keyboard, mouse, foot pedal, microphone and speaker. Data storage 442 may be any suitable data storage device, such as a local or remote computing device (e.g. a computer, hard drive, digital media device, or server) having a database stored thereon. In the example shown in FIG. 8, data storage device 442 includes identification data 450 for identifying one or more medical instruments 460 and configuration data 452 that associates customized configuration parameters with one or more medical instruments 460. Data storage device 442 may also include preoperative image data 454 and/or medical procedure planning data 456. Although data storage device 442 is shown as a single device in FIG. 8, it will be understood that in other embodiments, data storage device 442 may be provided as multiple storage devices.

Medical instruments 460 are identifiable by control and processing unit 400. Medical instruments 460 may be connected to, and controlled by, control and processing unit 400, or may be operated or otherwise employed independent of control and processing unit 400. Tracking system 120 may be employed to track one or more of medical instruments and spatial register the one or more tracked medical instruments to an intraoperative reference frame.

Control and processing unit 400 is also interfaced with a number of configurable devices, and may intraoperatively reconfigure one or more of such devices based on configuration parameter s obtained from configuration data 452. Examples of devices 420, as shown in the figure, include one or more external imaging device 422, one or more illumination devices 424, robotic arm 105, one or more projection devices 428, and one or more displays 115.

Embodiments of the disclosure can be implemented via processor(s) 402 and/or memory 404. For example, the functionalities described herein can be partially implemented via hardware logic in processor 402 and partially using the instructions stored in memory 404, as one or more processing engines 470. Example processing engines include, but are not limited to, user interface engine 472, tracking engine 474, motor controller 476, image processing engine 478, image registration engine 480, procedure planning engine 482, navigation engine 484, and context analysis module 486.

It is to be understood that the system is not intended to be limited to the components shown in the Figure. One or more components control and processing 400 may be provided as an external component or device. In one alternative embodiment, navigation module 484 may be provided as an external navigation system that is integrated with control and processing unit 400.

Some embodiments may be implemented using processor 402 without additional instructions stored in memory 404. Some embodiments may be implemented using the instructions stored in memory 404 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

The preceding example embodiments have described systems and methods in which a device is intraoperatively configured based on the identification of a medical instrument. In other example embodiments, one or more devices may be automatically controlled and/or configured by determining one or more context measures associated with a medical procedure. A "context measure", as used herein, refers to an identifier, data element, parameter or other form of information that pertains to the current state of a medical procedure. In one example, a context measure may describe, identify, or be associated with, the current phase or step of the medical procedure. In another example, a context measure may identity the medical procedure, or the type of medical procedure, that is being performed. In another example, a context measure may identify the presence of a tissue type during a medical procedure. In another example, a context measure may identify the presence of one or more fluids, such as biological fluids or non-biological fluids (e.g. wash fluids) during the medical procedure, and may further identify the type of fluid. Each of these examples relate to the image-based identification of information pertaining to the context of the medical procedure.

Figure 9:
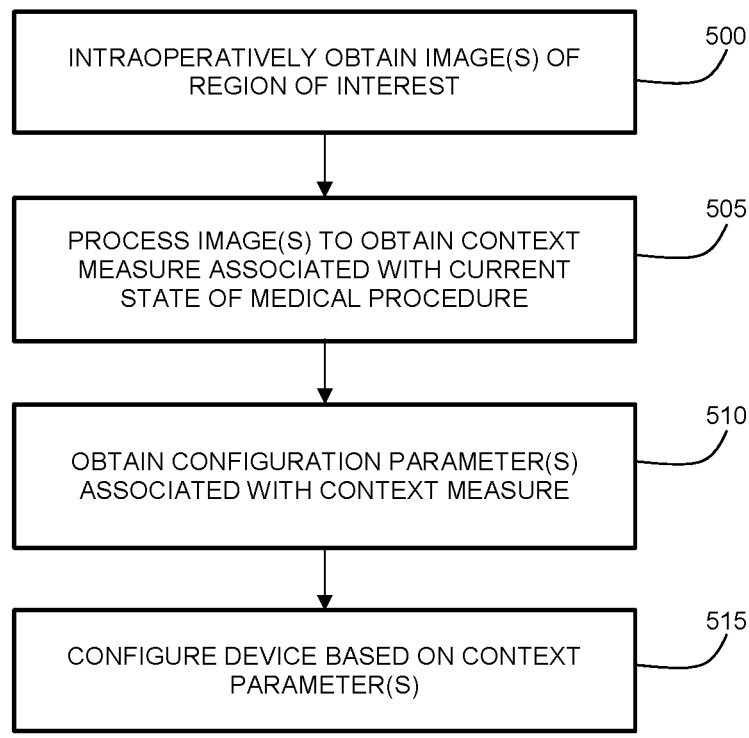
FIG. 9 is a flow chart illustrating an example method of intraoperatively configuring one or more devices based on the image-based detection of a context measure associated with a medical procedure.

An example method of intraoperatively configuring one or more devices based on the image-based detection of a context measure associated with a medical procedure is illustrated in the flow chart shown in FIG. 9. In step 500, one or more images are obtained during the medical procedure. The one or more images are then processed in step 505 to obtain (e.g. calculate) at least one context measure associated with the current state of the medical procedure. Examples of various context measures, and methods of obtaining the context measures, are provided below. The one or more context measures are then employed to obtain one or more configuration parameters for adaptively and intraoperatively configuring at least one device that is employed during the medical procedure.

In one example implementation, optical image analysis is employed to obtain an image measure associated with a tissue type that is exposed or otherwise detectable at the present state of the medical procedure. One or more optical images are intraoperatively obtained and processed to determine the presence of one or more tissue types, and one or more context measures are provided that are associated with the detection of the one or more tissue types. The one or more context measures are then used to determine one or more customized configuration parameters.

Various image processing methods may be employed in order to identify the presence of a tissue type. For example, in one example implementation, tissue identification may be performed via hyperspectral optical imaging. Hyper-spectral imaging can be accomplished by scanning a spectrally-resolved optical detector across the region of interest and collecting signals associated with multiple wavelengths at each scan point, or collecting a multi-spectral detector images. Various types of hyperspectral detectors and configurations are known in the art.

FIG. 10A illustrates an example method of performing tissue identification via hyperspectral imaging. In step 520, hyperspectral image data is obtained by intraoperatively imaging a region of interest. The hyperspectral image data includes per-pixel spectral data. It will be understood that the spectral data may be provided as a set of values at wavelengths spanning a spectral range of interest that defines a digitized spectrum, or may be provided as discrete values a small set of wavelengths or wavelength bands, such as red-green-blue intensity data.

In the example method presently considered, the per-pixel spectral data is processed, in step 525, to identify groups of adjacent pixels having a similar spectral response, thereby spectrally segmenting the image into one or more regions of similar spectral content. Pixels with similar spectral content may be identified based on the calculation of a spectral similarity measure between adjacent pixels.

For example, a spectral similarity measure for two pixels may be calculated by summing, over all wavelengths, the square of the difference between the values of the two intensity spectra (optionally after initially normalizing the two spectra), and dividing the result by the square of the average net intensity (summed over all wavelength values) of the two pixels. In such a case, two pixels may be deemed to have similar spectral responses if their spectral similarity measure is less than a pre-selected threshold value. A suitable threshold value may depend on the degree of spectral similarity that is sought, which may depend on the type of medical procedure that is being performed.

In one example implementation, when at least two adjacent pixels are found to have spectral similarity, the subsequent calculation of the spectral similarity measures for each additional adjacent pixel may be performed by summing, over all wavelength values, the square of the difference between the values of (i) the intensity spectrum of the adjacent pixels and (ii) the average intensity spectrum of all other pixels already having been deemed to be similar, and dividing this result by the square of the average intensity of all other pixels having been deemed to be similar. It will be understood that the above similarity method is merely one example method, and that other methods may be employed to obtain a similarity measure between pixels.

If a region is identified as having spectral similarity (e.g. similarity within the pixels spanning the region), then the average spectral response for the pixels within the region may be employed for tissue identification, as shown at step 530 of FIG. 10. For example, the average spectral response for the region may be compared to one or more reference spectra, where the reference spectra are each associated with a given tissue type; for example, particular spectra may be correlated to tumor tissue or white or grey brain matter. The comparison may be performed using a similarity measure as described above. In some embodiments, the comparison may be performed only for one or more regions having a number of pixels that exceeds a minimum value, such that tissue identification is only performed for regions beyond a threshold size.

The similarity measure between an average spectral response of an identified region and a given reference spectrum may be employed to provide a confidence measure associated with tissue identification, where a higher confidence measure indicates a higher probability that the tissue within the identified region corresponds to the tissue type of the reference spectrum. In one example implementation, a region may be associated with a tissue type if the confidence measure exceeds a preselected value. In cases in which two or more tissue types are identified based on having confidence factors that exceed a threshold, then the tissue may be identified based on the tissue type having the higher confidence measure. The identified tissue type, or an identifier associated with the identified tissue type, provides a context measure associated with the current state of the medical procedure.

The image processing steps described above may be performed by an image processing module 478 of control and image processing module 400, as illustrated in FIG. 8. Furthermore, the spectral similarity analysis described above may be performed by context analysis module 486.

It will be understood that the preceding example method of performing hyperspectral tissue identification is but one method of processing hyperspectral image data in order to identify a tissue type, and that other methods may be employed without departing from the scope of the present disclosure. For example, methods of hyperspectral imaging are disclosed in PCT Patent Application No. PCT/CA2014/050268, titled "SURGICAL IMAGING SYSTEMS", filed on Mar. 14, 2014, which is incorporated herein by reference in its entirety.

Furthermore, it will be understood that tissue identification may be performed according to other methods than hyperspectral imaging. For example, fluorescence spectral image data or Raman spectral image data may be obtained and processed, in a manner as described above, to identify one or more tissue types based on similarity to reference spectra. For example, in the case of Raman imaging, tissue identification may be performed by Raman imaging or by scanning a Raman point probe over multiple locations within a region of interest.

In some embodiments, Raman imaging may be combined with optical imaging in order to identify one or more tissue types.

After obtaining a context measure associated with the current state of the medical procedure (in this case, associated with an identified tissue type), control and processing unit 400 may be employed to obtain configuration parameters for intraoperatively configuring one or more devices based on the context measure. The configuration parameters are obtained from pre-selected configuration data associating customized configuration parameters for one or more devices with different context measures. The customized configuration parameters are employed to adaptively configure the device during the medical procedure.

This is performed in a manner similar to the preceding embodiment in which the configuration parameters are obtained for configuring a device based on the identity of medical instruments.

An example of configuration data that associates configuration parameters for illuminators 265 with one or more tissue types is shown in FIG. 10B. For example, one or more tissue types may be associated with a pathology, such as a tumor. An example of a configuration parameter for the illumination is the optical illumination spectrum. The spectrum can be modified such that the illumination light has either greater depth penetration or enhances surface contrast based on the scattering and absorption properties of the tissue. This increase in either light penetration or surface contrast can enable tissue features not visible under white light to be visible, and as such, enable better tissue identification. Increased light penetration allows for visualization of subsurface structures embedded in the tissue, while enhanced surface contrast allows for visualization of fine surface features. Example illumination spectra parameters are provided in FIG. 10B for brain white matter, brain grey matter, and muscle. These three tissues strongly absorb light below 500 nm, 550 nm, and 650 nm respectively, with lower absorption above these levels.

In another example implementation, optical image analysis, such as the image analysis methods described above, may be employed for identifying the intraoperative presence of one or more types of fluids. For example, the aforementioned example embodiment involving hyperspectral tissue analysis may be adapted to detect the presence of one or more fluids, based on a comparison to reference spectra from known fluids. For example, such a method may be employed to detect the presence of biological fluids such as blood, and non-biological fluids such as a saline fluid.

In one example implementation, the intraoperative identification of the presence of a fluid may be employed to improve imaging performance. A significant issue with current surgical optical systems and devices is glare caused by fluids that reflect illumination within a surgical cavity. The glare can cause imbalance in the dynamic range of an imaging camera, causing the upper range of the camera's dynamic range to become saturated. In addition, glare can cause the illumination intensity across the frequency spectrum of an imager to be unbalanced, depending on the illumination and conditions of the medical procedure. Accordingly, in some embodiments, configuration parameters associated with the intraoperative presence of a given fluid type may be provided for intraoperatively reconfiguring one or more components of an optical imaging system in order to improve imaging conditions. For example, configuration parameters may be provided for modifying and/or improving image quality metrics such as color and white balance.

In another example implementation, optical image analysis may be employed to obtain an image measure that is indirectly associated with the presence of one or more tissue types, fluids, or other material properties. For example, although the preceding example embodiments employed a method in which an average spectral response from an identified region is compared with a set of reference spectra associated with tissue or fluids, in other embodiments, the average spectral response, or another suitable imaging measure, may be compared with reference spectra that are not directly associated with a given tissue or fluid type.

In one example embodiment, the reference spectra may be associated with a phase or step of the medical procedure. FIG. 11A provides an example flow chart illustrating such an embodiment. Steps 540 and 545 may be performed in a manner similar to steps 520 and 525 of the preceding method that was illustrated in FIG. 10A, where image data (such as hyperspectral image data) is intraoperatively acquired and processed to obtain one or more regions with a similar spectral response. In step 550, an average spectral response from an identified region is compared with reference spectra that are associated with different phases of the medical procedure. For example, one or more reference spectra may be provided that are associated with a first phase of a medical procedure, while one or more other reference spectra may be provided that are associated with a second phase of the medical procedure. For example, reference spectra may instead be obtained from previous medical procedures, such that a set of reference spectra are provided where each reference spectra is associated with a given phase of the medical procedure. Finally, in step 555, the phase of the medial procedure is obtained based on the similarity between the average spectral response and the reference spectra (methods of similarity analysis were described in the preceding example pertaining to tissue type analysis).

In such an example embodiment, the context measure that is employed to determine one or more configuration parameters for intraoperative configuring a device is the identified phase of the medical procedure.

The reference spectra associated with different phases of the medical procedure may be produced according to several different methods. In one embodiment, the reference spectra may be obtained from previously performed surgical procedures. For example, spectra obtained at different phases of a number of prior medical procedures may be obtained and employed to provide reference spectra pertaining to the different phases of the medical procedure. In one example method, multiple spectra may be obtained for each phase of the medical procedure and averaged to produce a representative average spectra for each phase of the medical procedure. In another example implementation, reference spectra corresponding to different phases of the medical procedure may be produced based on reference spectra of tissues and/or fluids that are expected to be exposed at different phases of the medical procedure.

An example of configuration data that associates configuration parameters for camera 255 with different phases of the medical procedure is shown in FIG. 11B. During the craniotomy the camera may or may not be utilized by the surgeon given the field of view is normally large enough for the surgeon to accurately perform the step without requiring assistance, hence the camera will remain in an neutral state with no zoom. During cannulation the robotic arm holding the camera will orient it in a position and orientation relative to the port to provide a view of the graduation marks on the introducer. As the introducer with attached port is penetrated into the brain to access the tumor the graduation marks provide an indication of the depth of the instrument. As such during this stage a view requiring at minimum the ability to decipher the graduation marks on the port is required. During gross and fine resection, the camera is vital to the surgeon as it provides a view down the port where the surgeon is performing surgery and the surgeon cannot view well with their own eyes. At these stages the camera will be zoomed to different views such as the entire distal end of the port as well as the particular tissue being resected during fine resection.

Figure 21:
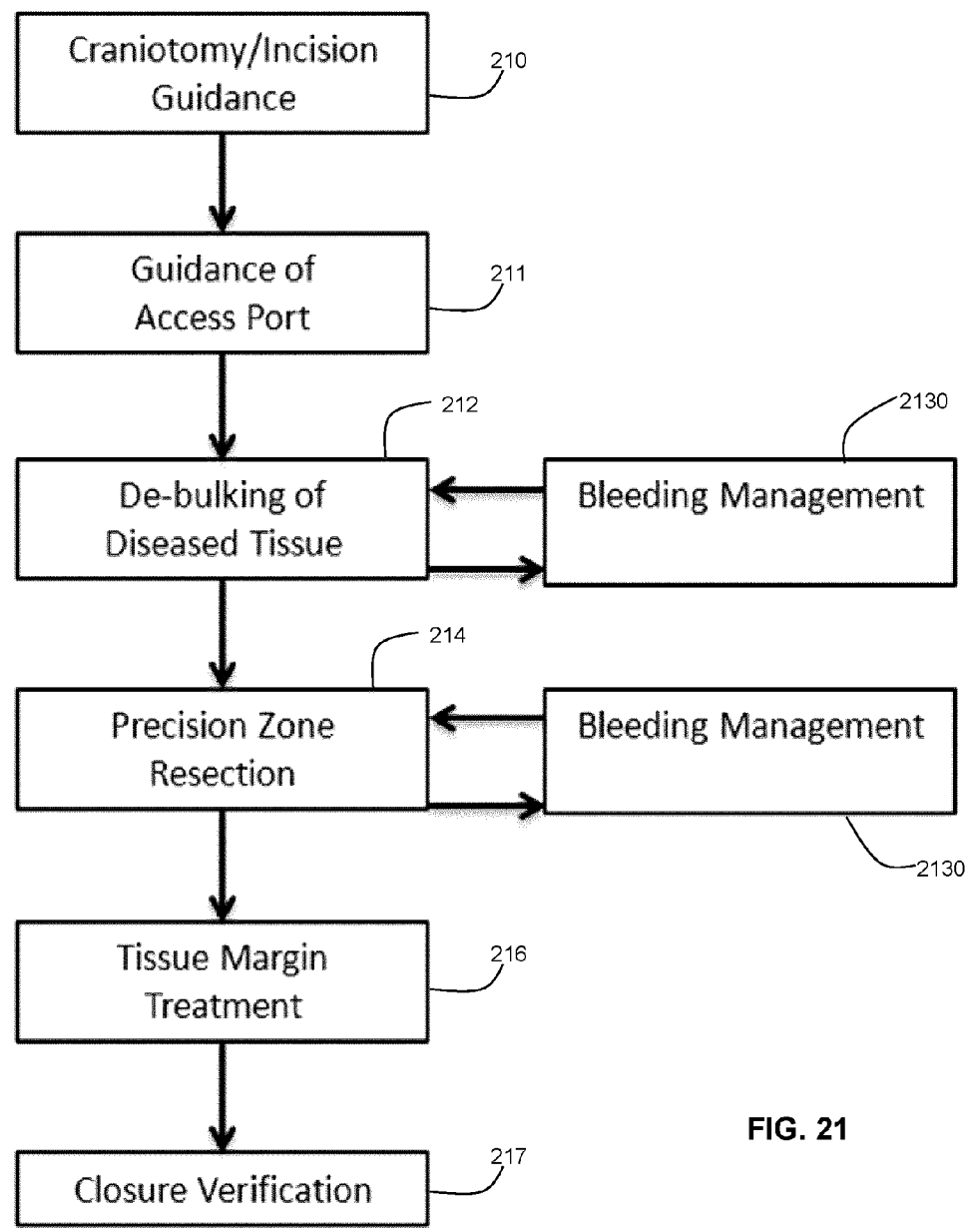
FIG. 21 is a flowchart describing the phases of a port based neurosurgery.

FIG. 21 depicts an exemplary port based surgery flow inclusive of the stages of surgery a surgeon would undertake to complete the procedure. In each stage there are applicable adaptive processes that can run to streamline the procedure to provide more accurate and time efficient surgical procedures. These processes can utilize various context measures ranging from some non-limiting examples being intraoperative imaging, temporal information, spatial positions of objects related to the surgery, medical instruments being used, intraoperative patient vitals (for example, breathing rate, blood pressure, etc.), etc. The following paragraph describes various adaptive processes that would be run with respect to the port-based procedure depicted in FIG. 21. It should be noted that each stage of the surgery may be identified using various context measures and are also provided below as non-limiting examples. It should also be noted that similar examples of configurations based on context measures are listed in FIG. 5J.

In the first stage (2100) of the surgery the Craniotomy / Incision stage can be identified by the navigation system control and processing unit through the identification of either a scalpel or neurosurgical drill being utilized by the surgeon through methods described herein. During this stage an exemplary adaptive process would involve the UI adjusting user interface being reconfigured to provide a digital display of the depth of the drill into the patient's skull as the surgeon is performing the craniotomy. It should be noted that the depth of the drill can be calculated from the navigation system as it knows the spatial position and pose of both the drill and skull. Such examples of navigation system is described in detail in PCT Patent Application No. PCT/CA2014/000247, titled "METHOD, SYSTEM AND APPARATUS FOR CONTROLLING A SURGICAL NAVIGATION SYSTEM", and filed on Mar. 14, 2014, which is incorporated herein by reference in its entirety.

Once the craniotomy has been completed the next stage (2110) of the surgery is cannulation (Guidance of Access Port). This stage can be identified by again recognizing the tools being utilized such as the ultrasound used to scan under the surface of the dura and in addition the introducer which is inserted into the port and used to penetrate the brain to provide access to the tumor in a non-traumatic manner. Both tools can be identified using tracking mechanisms as described herein. Another non-limiting context parameter that may be used to identify the stage of the surgery would be the time at which the surgery is occurring relative to the start of the surgery given this parameter was programmed into the control and processing unit 400. During the craniotomy, the control and processing unit 400 may be used to maneuver a robotic arm mounted with an imaging scope to view the cannulating introducer from an orthogonal angle so the graduation marks located on the introducer may be read, this adaptive process is described above.

Figure 24:
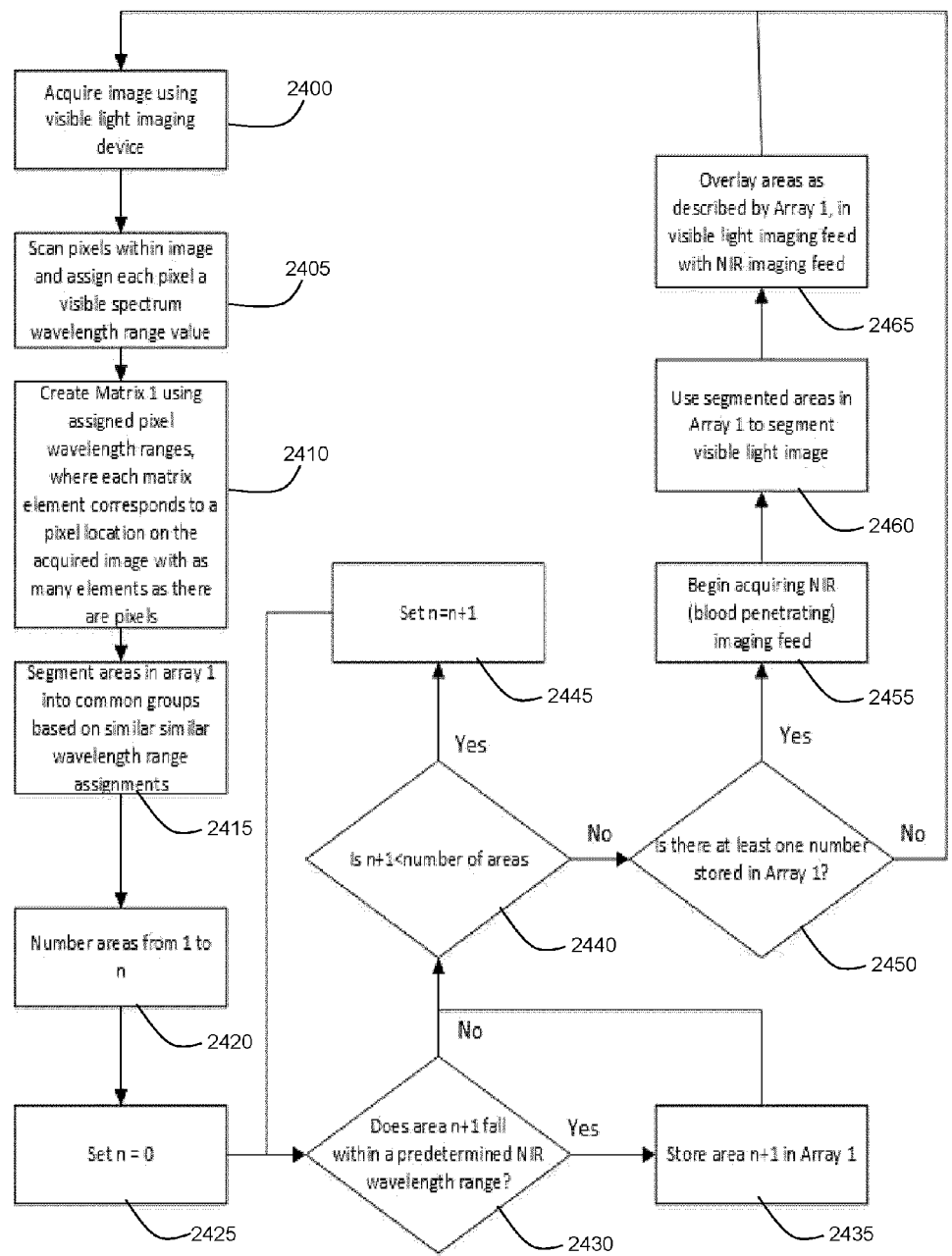
FIG. 24 is a flow chart describing the analysis of images and activation of near infrared imaging.

The next stage (2120) in the procedure is gross resection (also referred to as De-bulking of Diseased Tissue in FIG. 21) of the unhealthy tumor tissue. At this stage the surgeon is resecting the mass bulk of the tumor from the patient through the access port. Again one context parameter used by the navigation system control and processing unit 400 to identify this stage of the surgery would be the removal of the introducer instrument from the surgical field and the introduction of a resection tool. This stage (2120) as well as the next one Precision Zone Resection (2140) or more commonly known as fine resection both function in parallel with the Bleeding Management stages (2130) and (2130). Through a periodic wavelength spectrum analyses of an imaging feed (as depicted by FIG. 24 and described below in detail) acquired using the visible imaging device mounted on the robotic arm (used to provide an enhanced view of the distal end of the port where the surgeon is performing the procedure) a bleed can be identified by the control and processing unit 400.

Figure 23:
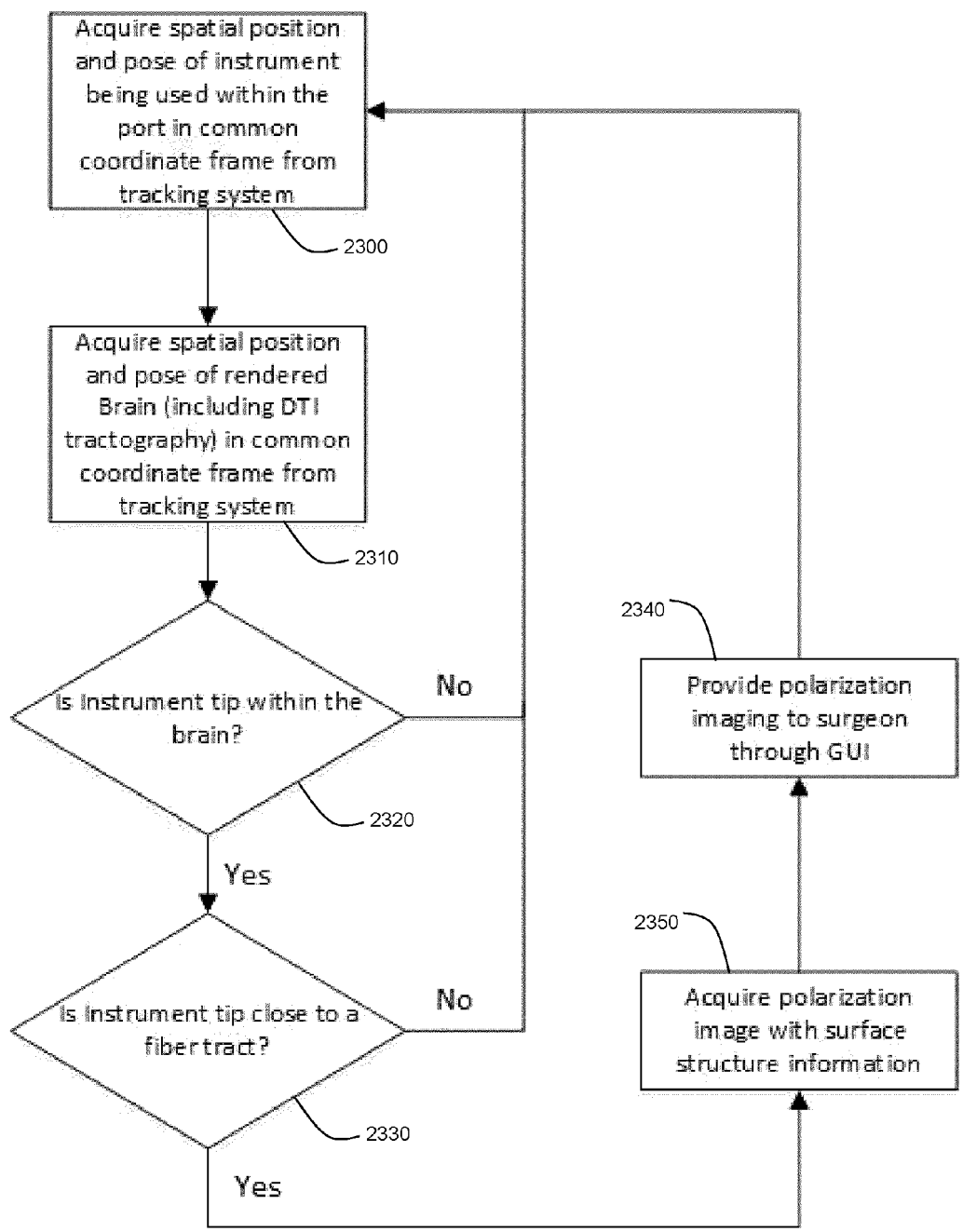
FIG. 23 is a flow chart describing the analysis of spatial data and the activation of polarization imaging.

An adaptive response to the identification of blood occluding the view of the tissue of interest being operated on by the surgeon, would be the overlay of NIR imaging on the occluded areas of the visible imaging as depicted by FIG. 23 and described in detail below. It should be noted that the context parameter used to identify the blood, would be its visible wavelength (color) spectrum. During the gross resection stage (2120)), a periodic fluorescence analysis can be performed to the imaging feed acquired using the visible imaging device mounted on the end of a robotic arm as described above. When a particular fluorescence spectrum that is correlated with tumor tissue is determined by the analysis the system can adaptively configure the imaging device to begin imaging using the fluorescence camera to provide enhanced differentiation between the healthy and unhealthy brain tissue. In addition the UI may simultaneously be configured to provide a view of the fluorescence image beside or overlaid on top of the visible light imaging.

The next stage in the procedure is fine resection (2140). In this stage the surgeon begins resecting tumor at the boundaries of the healthy tissue. A context parameter which could be potentially used to determine this stage of the procedure may be the zoom of the visible imaging device given that the surgeon indicates that they require some zoom above a particular threshold. Another context parameter could be when the location of the tool is close to the edge of the tumor on the rendered MRI scan of the patient. Given that the system knows the location of the tool relative to the patient's brain as a result of the registration of the 3D rendered MRI scan, when the system detects the tool is near a nerve tract, the system can adaptively configure the imaging device to begin acquire polarization sensitive imaging (as depicted in FIG. 23 and described below in detail).

It should be noted that this imaging provides more structural information than simply visible light imaging as structure can be inferred from the polarized light, the method of which is described in [Wood, M. et al., Polarization Birefringence measurements for characterizing the myocardium, including healthy, infarcted, and stem-cell regenerated tissues], J. Biomed. Opt. 15(4), 2010. The context measure in the aforementioned example mentioned would be the location of the tracked instrument (in this case a resection device) with respect to the registered patient brain and rendered MRI scan with DTI data.

During the Therapeutic delivery stage (2160) of the procedure therapeutic drugs are delivered to the region of interest where the tumor is located. A context measure that can be used to determine this stage of the procedure could again be the use of a medical instrument, in particular a device used to deliver a therapeutic, such as a solution, to the site of interest. Given the medical instrument being used to deliver device or potentially an additional instrument also being used at the surgical site of interest is mounted with a point source imaging probe able to provide a spectral analysis of a particular point at which its aimed, the adaptive system can utilize the spectrum acquired for say an array of points to map onto those points (i.e. on the imaging feed) the particular spectrums or an analysis of the particular spectrums assisting the surgeon in identifying where the therapeutic solution needs to be delivered. In addition the system may also be able to identify to the surgeon what particular solution could be utilized to most effectively provide therapy to those points if used in combination with a database system for example the one described in PCT Patent Application No. PCT/CA2014/050269, titled "INTERMODAL SYNCHRONIZATION OF SURGICAL DATA" and filed on Mar. 14, 2014, which is incorporated herein by reference in its entirety. The final stage in the process (2170) as depicted in FIG. 21 is the closure verification of the craniotomy after the invasive portion of the procedure has been completed.

In the preceding example embodiment, the current phase of a medical procedure is identified based on both intraoperative input by the user(s) and or image analysis, and this context measure is employed to determine customized configuration parameters for intraoperatively configuring one or more devices. The example implementation described above employed spectra image analysis of the surgical field (or of a region of interest within the surgical field) to extract a representative average spectral response, which may be compared with reference spectra associated with different phases of the medical procedure. In another example implementation, image analysis may be performed to identify one or more medical instruments that are being employed during a medical procedure, as described in detail above. However, rather than associating the identity of a given medical instrument directly with one or more configuration parameters, the identity of a medical instrument may be associated with a given phase of the medical procedure in which the medical instrument is commonly employed. Accordingly, the intraoperative identification of one or more medical instruments, based on image analysis, may be employed to provide a context measure identifying the current phase of a medical procedure, and configuration data, such as the example data provided in FIG. 11B, may be provided for the determination of one or more configuration parameters associated with the identified phase of the medical procedure.

In some embodiments, as described above, optical imaging may be performed to determine one or more context measures associated with the present state of the medical procedure. For example, optical imaging may be employed using one or more spectral regions including ultraviolet, visible, and infrared. In another example implementation, fluorescence imaging may be employed. Other examples of optical imaging modalities include polarization sensitive imaging, hyperspectral imaging, optical coherence imaging, and polarization-sensitive optical coherence imaging, and Raman imaging.

Although the preceding examples describe methods in which one or more context parameters are obtained based on intraoperative optical imaging, it will be understood that intraoperative imaging may be performed using any imaging modality, including, but not limited to, intraoperative magnetic resonance imaging, intraoperative ultrasound imaging, intraoperative photoacoustic imaging, intraoperative CT, and intraoperative PET.

Figure 12:
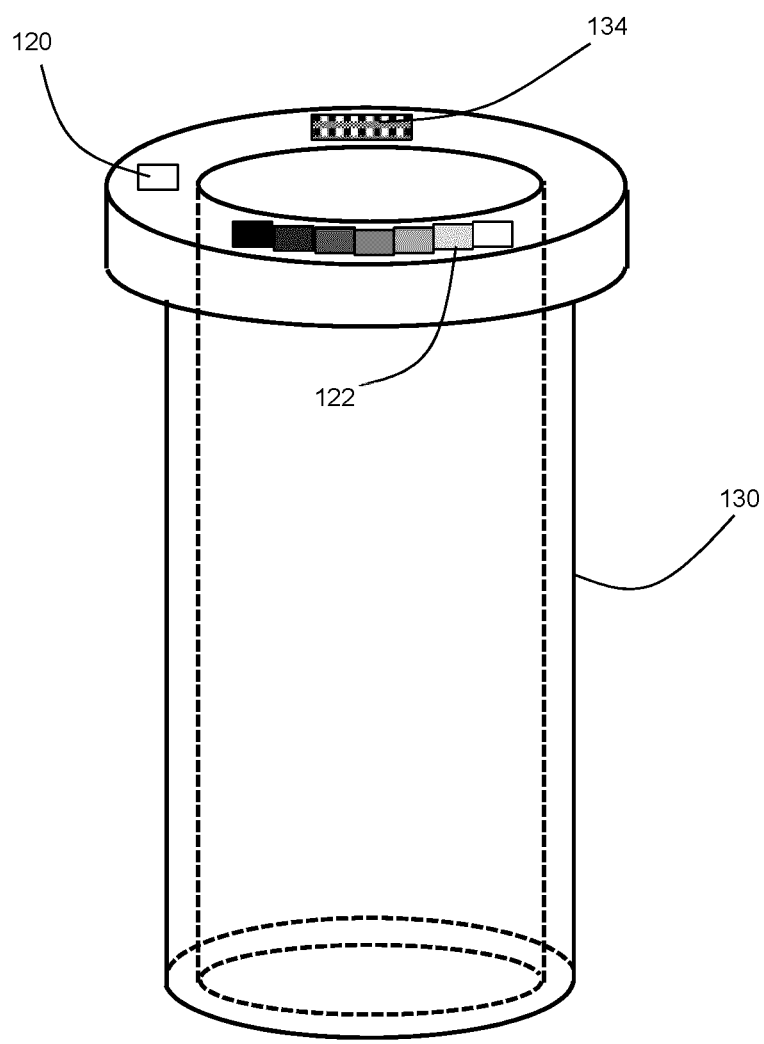
FIG. 12 shows an example access port having calibration features or targets that can be imaged and analyzed to automatically obtain one or more measures associated with color balance, white balance, dynamic range and illumination uniformity.

In one example, by using a calibration features or targets 134 on the access port 130, as shown in FIG. 12, and using known properties of the optical system, intraoperative images containing the calibration features can be analyzed to automatically obtain a measures associated with color balance, white balance, dynamic range and illumination uniformity (spatial uniformity). FIG. 12 depicts several calibration features which can be explained as follows. Item (120) is a white balance feature in which the processing system analyzes the image and uses this feature as the "true" white color, it can then adjust its configuration parameters such as its color mapping to confirm that the white it depicts is the same white as the calibration feature. Item (122) is a grey scale balance calibration feature used in a similar manner to the one described above for adjusting the imaging device configuration to match this grey balance range. Item (134) is an RGB color balance calibration feature. The imaging device when oriented to view down the port to the distal end can use these calibration features in the imaging focus periphery to obtain the optimal image for the surgery. In another embodiment the calibration features may be oriented within the opening of the port on the sidewalls. This embodiment may provide better calibration of the imaging device to match it with the interior of the port. Several published algorithms may be employed to automatically adjust these image characteristics. For example, the algorithm published by Jun-yan Huo et. al. ("Robust automatic white balance algorithm using gray color points in images," IEEE Transactions on Consumer Electronics, Vol. 52, No. 2, May 2006) may be employed to achieve automatic white balance of the captured video data. In other embodiments of the present disclosure, systems and methods are provided for adaptively and intraoperatively controlling multiple imaging modalities. An automated system employed during a medical procedure, such as the system shown in FIG. 5A, may include multiple imaging modalities that may be selectively controlled during a medical procedure.

In the example system shown in FIG. 5A, optical system 250 includes a primary optical imaging modality provided by camera 255, but also includes auxiliary imaging modality assembly 275. As noted above, auxiliary imaging modality assembly 275 may include one or more optical ports, and a mechanism, such as optical deflection device (e.g. a mirror, prism, reflector, filter, pellicle, window, or optical pick-off) that may be selective actuated to deflect the beam path along the port axis, thereby directing the optical beam to imaging and/or source optics associated with another imaging modality.

For example, in one example implementation, auxiliary imaging modality assembly 275 may include one or more ports for selectively employing an additional imaging modality including, but not limited to, fluorescence imaging, hyperspectral imaging, optical coherence tomography, polarization-sensitive optical coherence tomography, polarization-sensitive imaging, and Raman imaging. Control and processing unit 400 may thus provide one or more configuration parameters for selectively configuring the imaging system to employ one or more additional or alternative imaging modalities. Control and processing unit 400 may also provide one or more configuration parameters for selectively configuring the one or more additional or alternative imaging devices that employ other imaging modalities.

Figure 13A:
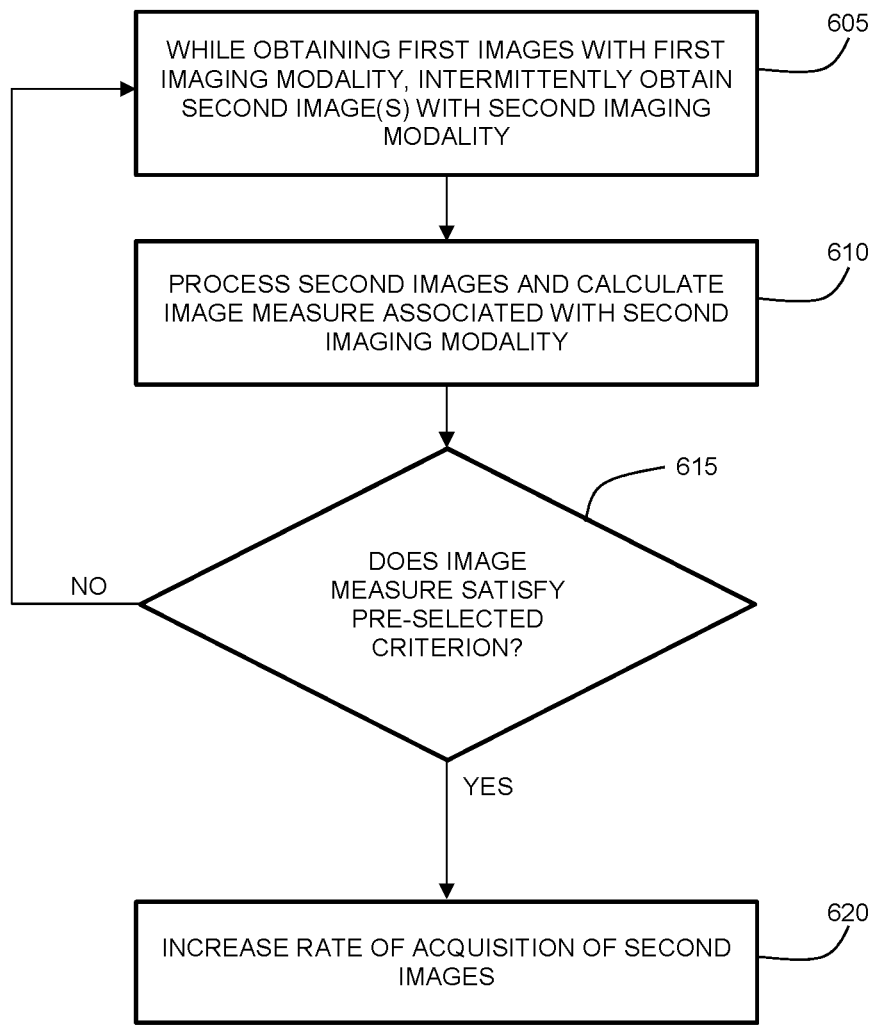
FIG. 13A a flow chart illustrating an example method of controlling a second imaging modality based on intermittent sampling and processing of image data from the second imaging modality while obtaining images using a first imaging modality

According to one example embodiment, at least two imaging modalities are controllable by control and processing unit 400, such that they may be selectively employed during a medical procedure. FIG. 13A provides a flow chart illustrating an example method of controlling a second imaging modality based on intermittent sampling and processing of image data from the second imaging modality while obtaining images using a first imaging modality. Such an embodiment provides intelligent and contextually relevant control of the second imaging modality relative to the first imaging modality.

It will be understood that the first imaging modality and the second imaging modality need not be associated with two separate imaging devices, and that in some example implementations, an imaging device that is initially configured to obtain images using a first imaging modality may be adaptively and dynamically configured to obtain images with a second imaging modality by modifying the imaging device. For example, an optical imaging device may be dynamically switched to fluorescence mode via the introduction of one or more filters into the optical beam path. In another example, an intraoperative magnetic resonance imaging system may be dynamically modified to switch between different modes of operation (e.g. T1 vs. T2 weighted images) via changes to the transmit and receive sequence.

As shown in FIG. 13A, images from a first imaging modality are intraoperatively obtained. For example, the first imaging modality may employ visible imaging using white light illumination. While obtaining the images from the first imaging modality, a second imaging modality is intermittently employed in order to obtain images, as indicated at step 605. For example, the second imaging modality may employ another type of optical imaging, such as fluorescence imaging. During this phase, the acquisition rate of the images from the second imaging modality may be lower than the acquisition rate of the images from the first imaging modality. In some non-limiting example implementations, the initial ratio of the acquisition rate of the first imaging modality to that of the second imaging modality may be greater than or equal to approximately 2, 5, 10, 50, 100, $10^3$, $10^4$, $10^5$ or $10^6$.

The images from the second imaging modality are processed in order to obtain an image measure that is employed to determine whether or not to continue imaging with the second imaging modality. Various examples of image measures, and methods of calculating such image measures, are described in detail below. As shown in step 615, the image measure is compared with a pre-selected criterion (or criteria) in order to determine whether or not to continue imaging with the second imaging modality. In the event that the image measure meets the pre-selected criterion, and it is thus determined that it would be suitable to continue imaging with the second imaging modality, the acquisition rate of images from the second imaging modality is increased, as shown at step 620. On the other hand, if the image measure does not meet the pre-selected criterion in step 615, one or more additional images are obtained using the second imaging modality, and the assessment is repeated until the pre-selected criterion is met.

The image measure that is obtained to determine whether or not to increase the acquisition rate of the second imaging modality can be obtained according to a wide range of methods. In one example embodiment, the image measure may be associated with a performance measure of the second imaging modality. For example, the image measure may involve a determination of a measure of signal-to-noise ratio of imaging with the second imaging modality, such that when the imaging measure associated with the signal-to-noise ratio exceeds the pre-selected criterion in step 615, the acquisition rate of the second imaging modality is increased. Another example of a performance-related image measure is a measure of the intensity of the signal that is obtained with the second imaging modality. Yet another example of a performance-related image measure is the amount of signal within a given frequency range or spectral range. These performance measures may be evaluated on a global basis using one or more statistical measures, or may be evaluated on a local or regional basis. For example, the pre-selected criterion evaluated in step 615 may require that a given performance threshold is satisfied by a pre-selected fraction of the pixels forming the image obtained via the second imaging modality. It is further noted that a plurality of images may be obtained from the second imaging modality, and an image measure may be obtained by processing the plurality of images (for example, via averaging the images).

It will be understood that while the preceding paragraphs describe the use of a single image measure, multiple image measures, and associated criterion, may be processed in order to determine whether or not to increase the acquisition rate of the second imaging modality.

In one example implementation, when the acquisition rate of the second imaging modality is increased in step 620, the acquisition rate of the first imaging modality may be reduced. In another example implementation, when the acquisition rate of the second imaging modality is increased in step 620, the acquisition rate of the first imaging modality may be maintained. In another example implementation, when the acquisition rate of the second imaging modality is increased in step 620, the acquisition of images from the first imaging modality may be terminated or suspended.

In one example embodiment, after having increased the acquisition rate of the second imaging modality based on the determined that an image measure has met pre-selected criterion, steps 610 and 615 may be performed to assess whether or not the image measure associated with the second imaging modality continues to meet the pre-selected criterion. In the event that the image measure fails to meet the pre-selected criterion, the acquisition rate of the second imaging modality may be reduced, and the method may be repeated (starting with step 605).

In one example embodiment, additional actions may be taken after having determined that the image measure associated with the second imaging modality satisfies the pre-selected criterion. For example, in a manner similar to the previously described embodiments, one or more devices that are used during the medical procedure may be reconfigured (e.g. by obtaining new configuration parameters from configuration data associating the configuration of one or more devices with the assessment of the criterion in step 615). In one example implementation, a user interface that displays the images obtained from the first imaging modality may be re-configured to additionally or alternatively display the images from the second imaging modality.

The additional images from the second imaging modality may be displayed according to a wide variety of different configurations, such as displaying the images from the first and second imaging modalities in a side-by-side configuration or in an overlaid configuration (optionally after having registered the images from the first imaging modality with those of the second imaging modality).

Figure 13B:
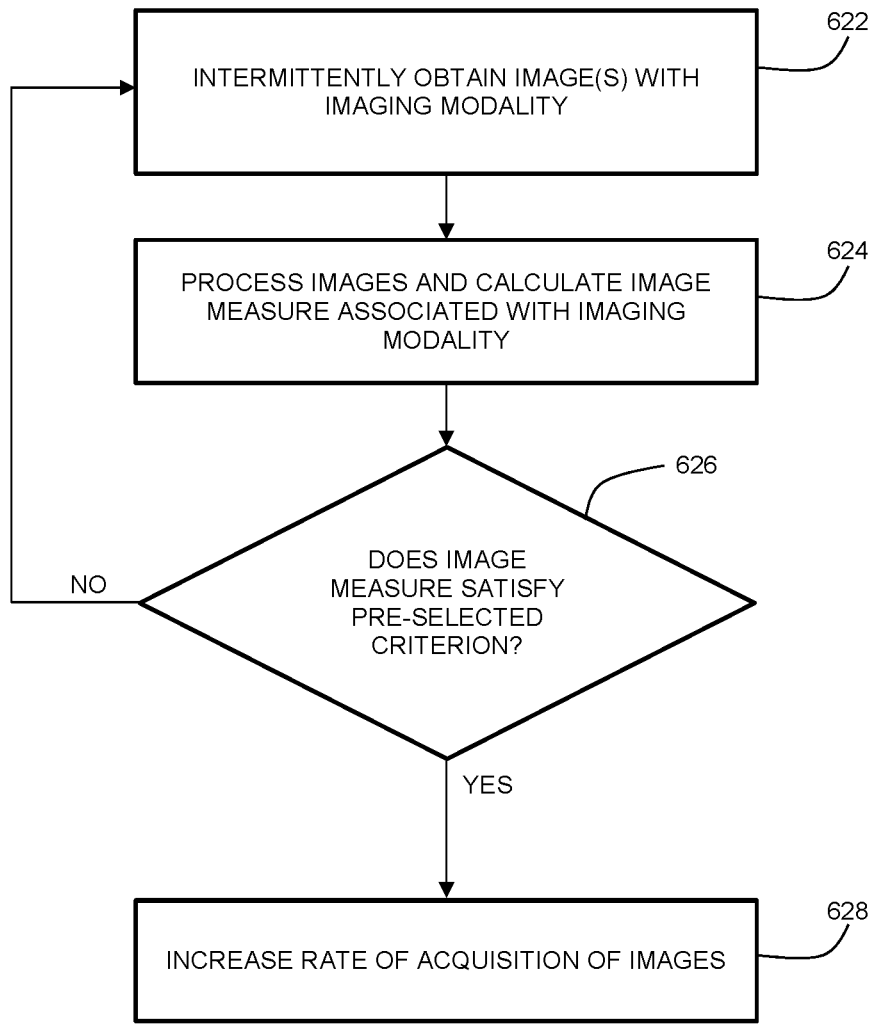
FIG. 13B is a flow chart illustrating an example adaptive and interoperative method of controlling the acquisition rate of images pertaining to an imaging modality.

It is also noted that in some embodiments, a method based on that shown in FIG. 13A may be implemented based solely on the intermittent acquisition of images from one imaging modality. This embodiment is illustrated in FIG. 13B, which provides an adaptive and interoperative method of controlling the acquisition rate of images pertaining to an imaging modality. In step 622, an imaging modality is employed to intraoperatively obtain images. The images are intermittently obtained at an initial pre-selected frame rate. The one or more images are processed to obtain an image measure in step 624. In step 626, the image measure is compared to pre-selected criterion, and if the criterion is met, the acquisition rate of the imaging modality is increased.

Figure 14:
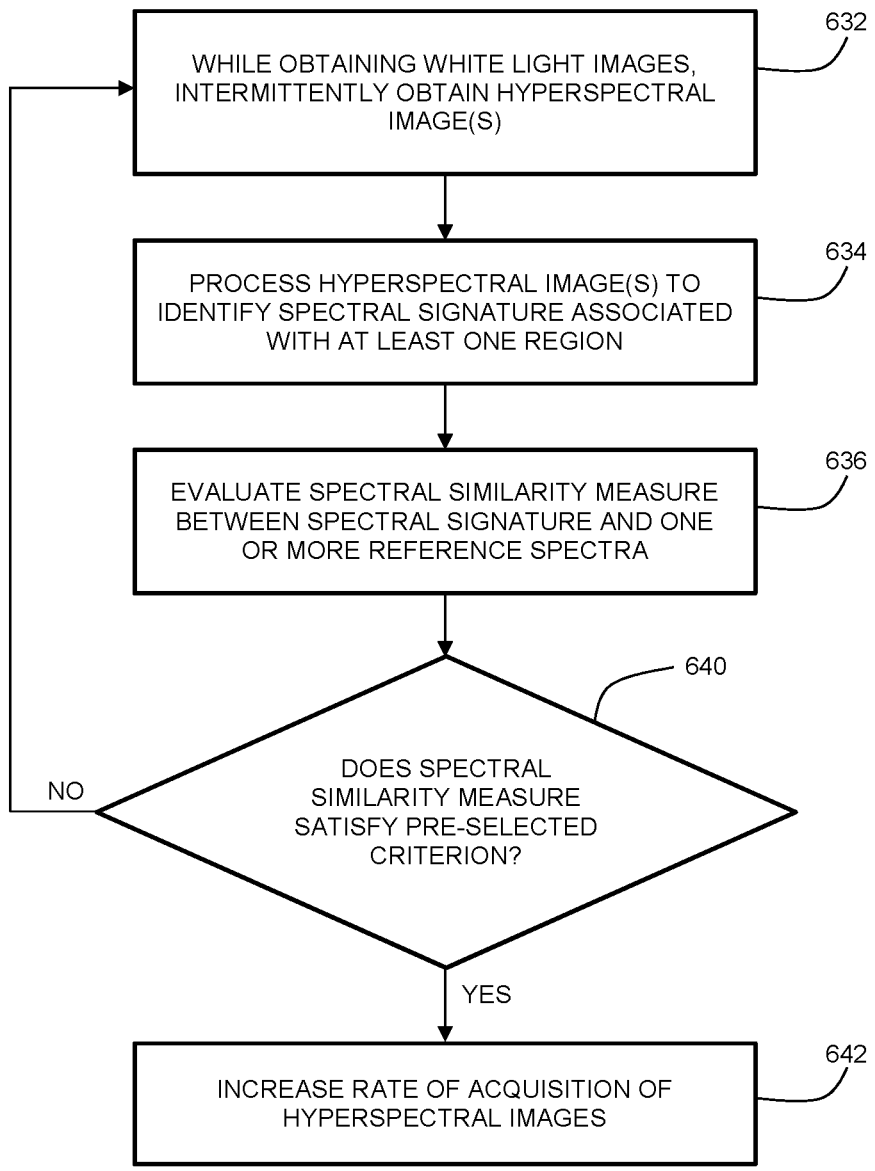
FIG. 14 is a flow chart illustrating an example implementation of a method of intraoperatively and adaptively controlling the acquisition of images from white light and hyperspectral imaging modalities.

Referring now to FIG. 14, a flow chart is shown illustrating an example implementation of a method of intraoperatively and adaptively controlling the acquisition of images from white light and hyperspectral imaging modalities. It will be understood that these imaging modalities are merely provided as examples. White light images are intraoperatively obtained, and in step 632, one or more hyperspectral images are intermittently obtained while obtaining the white light images. For example, one or more hyperspectral images may be obtained at a prescribed initial acquisition rate, such as, for example, a rate between once per minute and once per second.

Hyperspectral images may be obtained via a separate hyperspectral imaging device. In one example implementation, a hyperspectral imaging device may share one or more components with the white light imaging device. For example, as illustrated in FIG. 5A, imaging optics assembly 260 may be shared by both camera 255 (which, in the present example, would be employed for white light imaging), and by a hyperspectral detector that interfaces with optical system 250 through auxiliary imaging modality assembly 275.

The one or more hyperspectral images that are obtained in step 632 in FIG. 14 are then processed to obtain an image measure that may be employed to determine whether or not to increase the acquisition rate of hyperspectral images. The image measure can be associated with a wide range of metrics associated with the suitability or feasibility of performing hyperspectral imaging, including one or more of those described above.

In the present example, the image measure is obtained by processing the hyperspectral image data in order to identify the presence of one or more spectral signatures, as shown in step 634. The processing of the hyperspectral images may be performed as described above in relation to FIG. 11A, in which one or more regions are identified having a spectral similarity among pixels. Briefly, per-pixel spectral data from the hyperspectral images may be processed to identify groups of adjacent pixels having a similar spectral response, thereby spectrally segmenting the image into one or more regions of similar spectral content. Pixels with similar spectral content may be identified based on the calculation of a spectral similarity measure between adjacent pixels. If a region is identified as having spectral similarity within the pixels spanning the region, then the average spectral response for the pixels within the region may be employed as the spectral signature.

A spectral similarity measure is the evaluated between an identified spectral signature and one or more reference spectra, as shown in step 636. For example, the spectral signature may be compared to one or more reference spectra, where the reference spectra are each associated with a given tissue type, fluid type, or a given chemical or biological composition. For example, the spectral signature may be compared with one or more pathological tissue types, such as different types of tumors. The comparison may be performed using a similarity measure as described above. In some embodiments, the comparison may be performed only for one or more regions having a number of pixels that exceeds a minimum value, such that similarity assessment is only performed for regions beyond a threshold size.

If the spectral similarity measure satisfies a pre-selected criterion for one of the reference spectra (e.g. exceeds a pre-selected threshold) in step 640, then the acquisition rate of the second imaging modality is increased as shown at step 642. On the other hand, if the pre-selected criterion is not met, then the process is repeated and additional hyperspectral images are obtained in 632 and subsequently evaluated for spectral similarity with the reference spectra.

In another example implementation, the methods illustrated in FIGS. 13A and 13B may be employed to adaptive control the use of fluorescence imaging. For example, in one example implementation, the method illustrated in FIG. 13A may be performed such that the first imaging modality is white light imaging, and the second imaging modality is fluorescence imaging.

Figure 15:
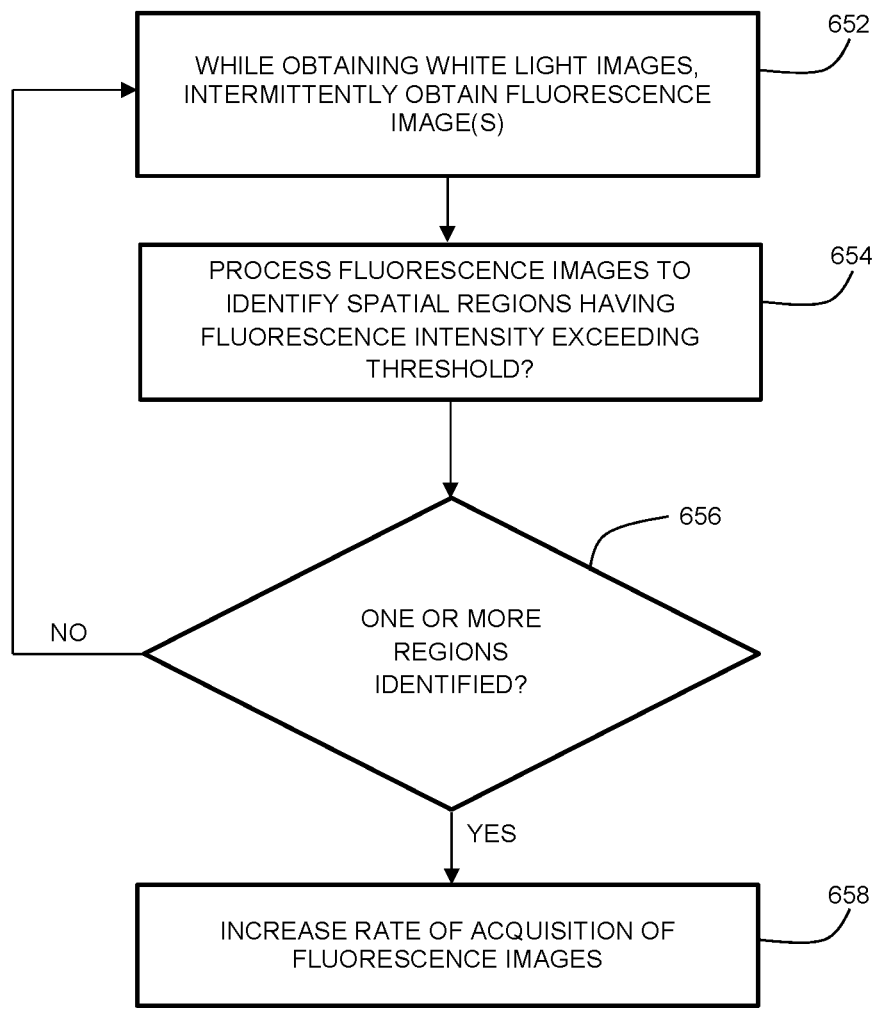
FIG. 15 shows a flow chart illustrating an example method of adaptively controlling the use of fluorescence imaging based on the intermittent sampling of and processing of fluorescence images.

An example implementation of this method is shown in FIG. 15. In step 652, one or more fluorescence images are intermittently obtained while obtaining while light images. Fluorescence image acquisition may be interleaved with white light image acquisition, in order to avoid crosstalk between the two modalities. The fluorescence images are processed to calculate an image measure associated with the intensity of the fluorescence signal. For example, the image measure may be obtained by calculating the net fluorescence intensity for all image pixels.

Alternatively, a spatially resolved measure of fluorescence intensity may be calculated. For example, as shown in step 654, the per-pixel fluorescence intensity data may be processed to identify groups of adjacent pixels having a fluorescence intensity exceeding a pre-selected threshold value, thereby segmenting the image into one or more regions having a fluorescence intensity above the threshold value. In one example, an identified region may be required to have a minimum number of pixels, such only regions greater than a minimum area are considered. If one or more regions are identified in step 656, the rate of acquisition of fluorescence images is increase.

In other example implementations involving fluorescence imaging, other measures associated with the fluorescence image may additionally or alternatively be obtained and compared to pre-selected criteria in order to determine whether or not to increase the fluorescence image acquisition rate. For example, a measure associated with the signal-to-noise ratio of one or more fluorescence images may be obtained, and the fluorescence image acquisition rate may be increased if the measure exceeds a pre-selected threshold. In another example, the fluorescence images may be spectrally resolved (e.g. using hyperspectral fluorescence detection) and the hyperspectral image processing methods pertaining to FIG. 14 may be employed.

The preceding embodiments involving the intermittent and intraoperative sampling of images from an imaging modality, and the processing of the images in order to determine whether or not to increase the acquisition rate of the images. In another example embodiment, images from a first imaging modality may be obtained and processed in order to trigger the use of a second imaging modality.

Figure 16:
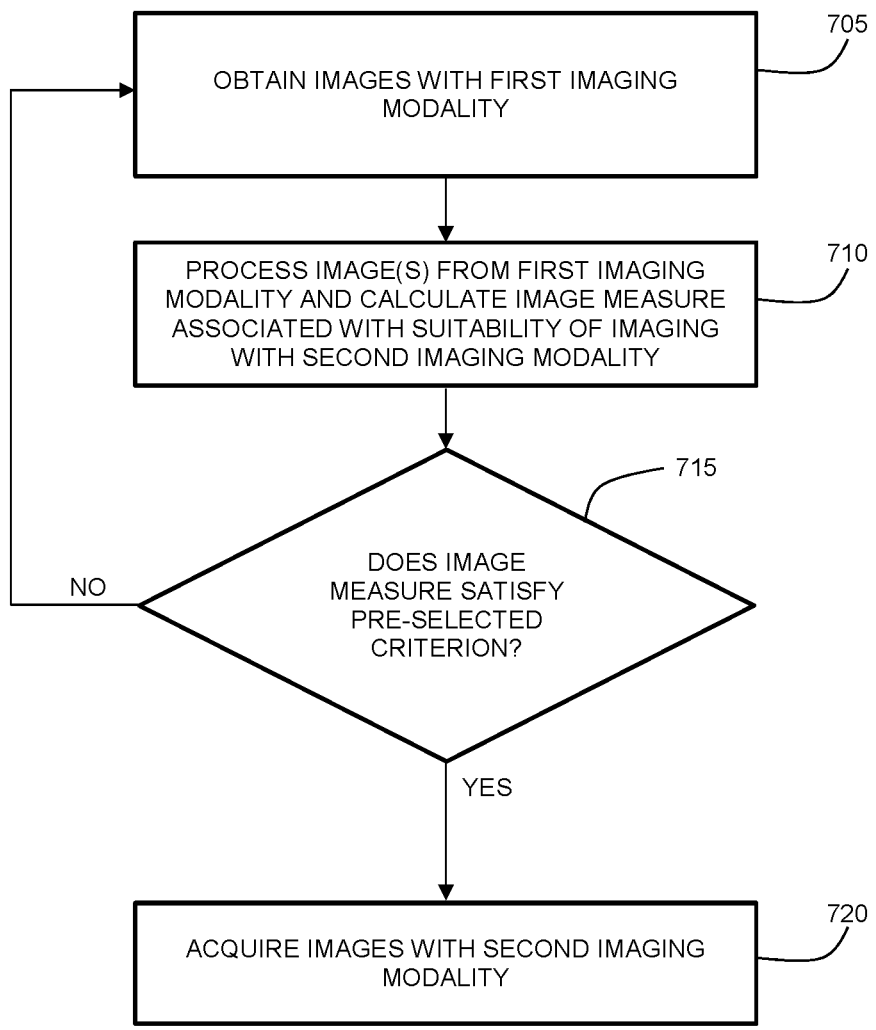
FIG. 16 is a flow chart illustrating an example method in which images from a first imaging modality may be obtained and processed in order to trigger the acquisition of images from a second imaging modality.

FIG. 16 provides a flow chart illustrating an example of such an embodiment. In step 705, a first imaging modality is employed to intraoperatively obtain images. The images are then processed in step 710 in order to obtain an image measure associated with the feasibility or suitability of performing imaging with a second imaging modality. Examples of such image measures are described below. The image measure is then compared to a pre-selected criterion in step 715, and if the criterion is met, images are subsequently acquired with the second imaging modality, as shown at step 720.

As in the preceding embodiment, the first imaging modality and the second imaging modality need not be associated with two separate imaging devices, and in some example implementations, an imaging device that is initially configured to obtain images using a first imaging modality may be adaptively and dynamically configured to obtain images with a second imaging modality by modifying the imaging device. For example, an optical imaging device may be dynamically switched to fluorescence mode via the introduction of one or more filters into the optical beam path. In another example, an intraoperative magnetic resonance imaging system may be dynamically modified to switch between different modes of operation (e.g. T1 vs. T2 weighted images) via changes to the transmit and receive sequence.

As described above, the image measure may be associated with the feasibility or suitability of imaging with the second imaging modality. The image measure can be obtained according to a wide range of methods. For example, in some example implementations, the image measure may be associated with an impairment of the performance of the first imaging modality, such that when the image measure exceeds a pre-selected threshold, it may be beneficial to switch to the second imaging modality. For example, as described below, the first imaging modality may be an optical imaging modality that suffers a performance degradation in the presence of glare, and the second imaging modality may be insensitive or less sensitive to glare. In such a case, when the image measure has a value that is associated with glare, the criterion in step 715 will trigger the acquisition of images using the second imaging modality.

In another example embodiment, an image measure may be associated with the determination of context measure, as described in the preceding embodiments. For example, an image measure that is obtained may provide an indication of the current phase of a surgical procedure, as described above. In such a case, the pre-selected criterion that is evaluated in step 715 may include a list of phases of the medical procedure for which the second imaging modality is desirable or suitable.

In another example embodiment, the image measure may be associated with a performance measure of the second imaging modality. For example, the image measure may involve a determination of a measure of signal-to-noise ratio of imaging with the second imaging modality, such that when the imaging measure associated with the signal-to-noise ratio exceeds the pre-selected criterion in step 715, the acquisition rate of the second imaging modality is increased. Another example of a performance-related image measure is a measure of the intensity of the signal that is obtained with the second imaging modality. Yet another example of a performance-related image measure is the amount of signal within a given frequency range or spectral range. These performance measures may be evaluated on a global basis using one or more statistical measures, or may be evaluated on a local or regional basis. For example, the pre-selected criterion evaluated in step 640 in FIG. 14 may require that a given performance threshold is satisfied by a pre-selected fraction of the pixels forming the image obtained via the second imaging modality. It is further noted that a plurality of images may be obtained from the second imaging modality, and an image measure may be obtained by processing the plurality of images (for example, via averaging the images).

It will be understood that while the preceding paragraphs describe the use of a single image measure, multiple image measures, and associated criterion, may be processed in order to determine whether or not to increase the acquisition rate of the second imaging modality.

In one example implementation as shown in FIG. 16, when the acquisition images with the second imaging modality is initiated in step 720, the acquisition rate of the first imaging modality may be reduced. In another example implementation, when the acquisition images with the second imaging modality is initiated in step 720, the acquisition rate of the first imaging modality may be maintained. In another example implementation, when the acquisition images with the second imaging modality is initiated in step 720, the acquisition of images from the first imaging modality may be terminated or suspended.

In one example embodiment, after having initiated the acquisition of the images from the second imaging modality based on the determined that an image measure has met pre-selected criterion, steps 710 and 715 may be performed to assess whether or not the image measure associated with the second imaging modality continues to meet the pre-selected criterion. In the event that the image measure fails to meet the pre-selected criterion, the acquisition of images with the second imaging modality may be reduced or terminated, and the method may be repeated (starting with step 705).

In one example embodiment, additional actions may be taken after having determined that the image measure associated with the second imaging modality satisfies the pre-selected criterion. For example, in a manner similar to the previously described embodiments, one or more devices that are used during the medical procedure may be reconfigured (e.g. by obtaining new configuration parameters from configuration data associating the configuration of one or more devices with the assessment of the criterion in step 615 as shown in FIG. 13A). In one example implementation, a user interface that displays the images obtained from the first imaging modality may be re-configured to additionally or alternatively display the images from the second imaging modality. The additional images from the second imaging modality may be displayed according to a wide variety of different configurations, such as displaying the images from the first and second imaging modalities in a side-by-side configuration or in an overlaid configuration (optionally after having registered the images from the first imaging modality with those of the second imaging modality).

Figure 17:
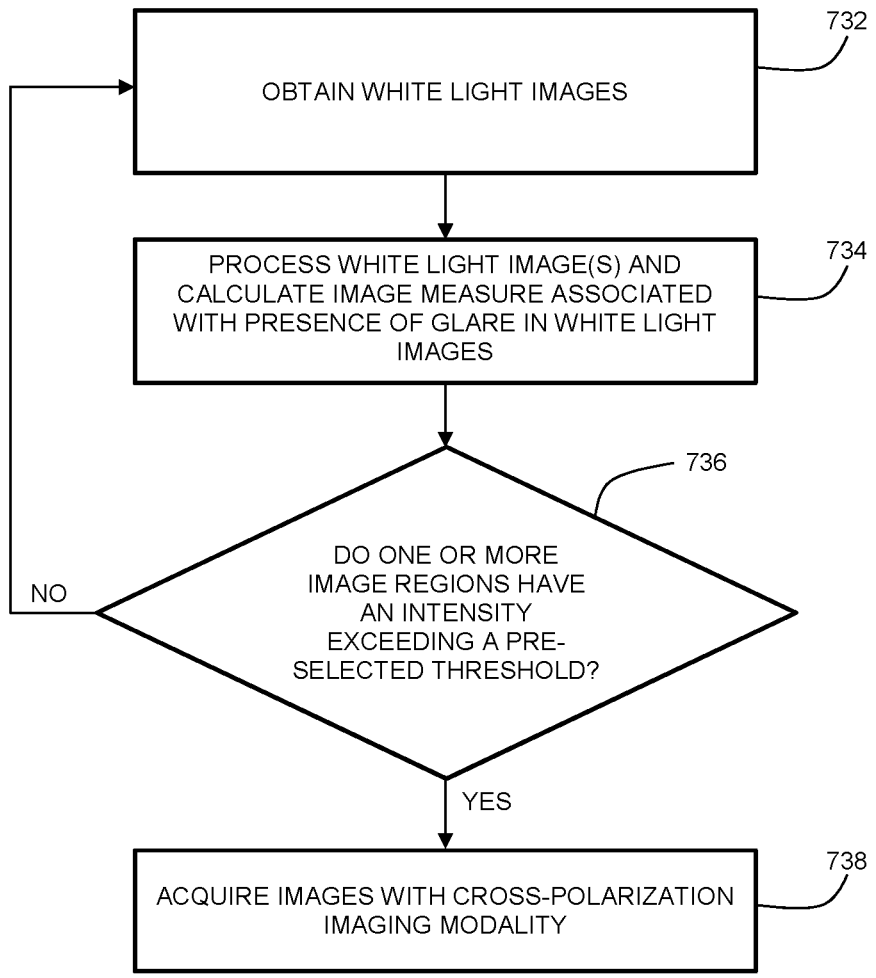
FIG. 17 is a flow chart illustrating an example method in which white light images are obtained and processed in order to trigger the acquisition of images using a hyperspectral imaging modality.

FIG. 17 illustrates an example implementation of the method outlined in FIG. 16, in which the first imaging modality employs white light imaging, and the second imaging modality employs cross-polarized imaging. In this example implementation, the system automatically switches to cross-polarized imaging device when a pre-selected criterion associated with the detection of glare in the images from the white light imaging modality. As noted above, a significant issue with current surgical optical systems and devices is glare caused by fluids that reflect illumination within a surgical cavity. The glare can cause imbalance in the dynamic range of an imaging camera, causing the upper range of the camera's dynamic range to become saturated. In addition, glare can cause the illumination intensity across the frequency spectrum of an imager to be unbalanced, depending on the illumination and conditions of the medical procedure.

Accordingly, in the example method illustrated in FIG. 17, white light images of a region of interest are initially obtained during a medical procedure, as shown at step 732. For example, such images may be obtained using camera 255 of optical system 250 shown in FIG. 5A. In step 734, the white light images are processed to calculate an image measure associated with the presence of glare in the white light images. For example, this may be performed by identifying one or more of regions within the image (groups of adjacent pixels) having an intensity value above a pre-selected intensity, where the pre-selected intensity is indicative of glare conditions. In one or more of such regions are identified, in step 736 (optionally where any given region has an area exceeding a pre-selected minimal area), then images are subsequently acquired using a cross-polarization imaging modality, as shown at step 738. The cross-polarization images may be intermittently obtained while continuing to obtaining the white light images.

Cross-polarized images may be obtained via a separate cross-polarization imaging device, or may be obtained by modifying the optical device that is employed for white light imaging. For example, the device employed for white light imaging may be modified by intraoperatively inserting, into the beam path of an illumination device, a first polarizer, and introducing, into the beam path of the optical imaging device, a second polarizer (an analyzer), where the first and second polarizers are oriented in a crossed configuration for performing polarization-sensitive imaging. In some example implementations, cross-polarization imaging may be performed using a high frequency polarization state actuation and deactivation device, a beam splitter and an alternate camera, or a beam splitter with same camera. In an example implementation in which a second imaging device is obtained for performing cross-polarized imaging, one or more cross-polarized images may be obtained concurrently with the acquisition of white light images.

The additional images from the cross-polarization imaging modality may be displayed according to a wide variety of different configurations, such as displaying the images from the white light and cross-polarization imaging modalities in a side-by-side configuration, in an overlaid configuration, or in a configuration in which the high-glare regions identified in the white light images are replaced with image data obtained from cross-polarization imaging.

Figure 18:
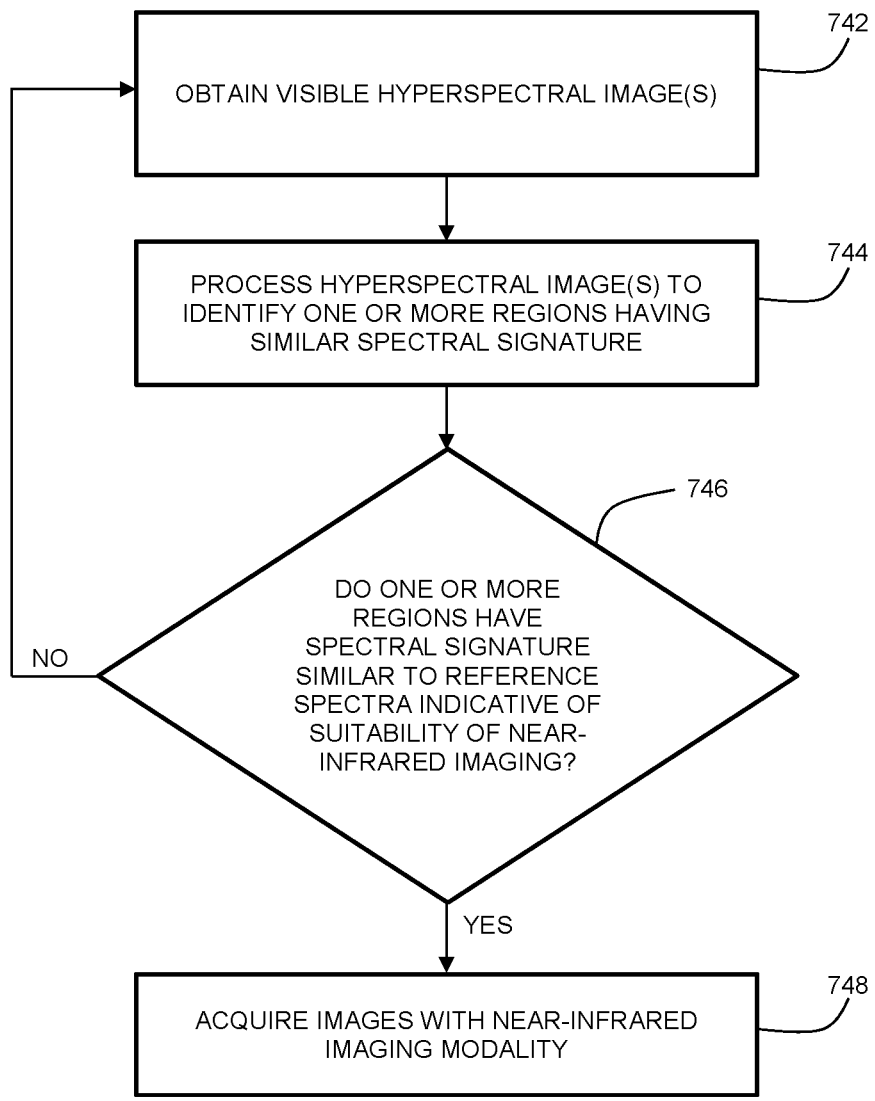
FIG. 18 is a flow chart illustrating an example method in which hyperspectral images are obtained and processed in order to trigger the acquisition of images using a near-infrared imaging modality.

FIG. 18 illustrates another example implementation of the method outlined in FIG. 16, in which the first imaging modality employs hyperspectral imaging, and the second imaging modality employs near-infrared imaging. In this example implementation, the system automatically switches to near-infrared imaging device when a pre-selected criterion associated with the detection of a spectral signature in the hyperspectral images is satisfied.

In step 742, one or more hyperspectral images are intraoperatively obtained. The one or more hyperspectral images are the processed, in step 744, in order to identify one or more spatial regions having a similar spectral signature. Example methods for identifying such regions, and a characteristic spectral signature for a given region, are described in detail above.

In step 746, the spectra signature from each identified region is compared to one or more reference spectra, where the reference spectra pertain to tissue types, fluids, material or biological compositions that are known to be suitable or feasible for near-infrared imaging.

In another example, the spectral signature may be processed to provide an image measure associated with the relative spectral intensity within one or more spectral bands, where the spectral bands are known to be associated with materials that do not absorb near-infrared light. In other words, the spectral signature may be processed to identify, directly or indirectly, the presence of a material that would support deeper image penetration via near-infrared imaging. The image measure may be compared to pre-selected criterion in order to selectively trigger the use of the near-infrared imaging modality.

In one example implementation, multiple image measures may be obtained and employed. For example, image measures associated with the presence of both near-infrared absorbing substances and near-infrared transparent substances may be combined to determine whether or not to trigger the use of the near-infrared imaging modality.

The spectral similarity can be determined, for example, based on the calculation of a spectral similarity measure, as described in detail above. In the event that sufficient spectral similarity is found to occur between a spectral signature from the hyperspectral images and the reference spectra, then the acquisition of near-infrared images is triggered in step 748.

It will be understood that the preceding example involving the analysis of images from one imaging modality to trigger the acquisition of images from another imaging modality are provided as non-limiting heuristic examples, and that the method may be adapted to various combinations of imaging modalities without departing from the scope of the present disclosure.

The additional images from the near-infrared imaging modality may be displayed according to a wide variety of different configurations, such as displaying the images from the hyperspectral and near-infrared imaging modalities in a side-by-side configuration, in an overlaid configuration, or in a configuration in which the regions identified in the hyperspectral images are replaced with image data obtained from near-infrared imaging.

Figure 22:
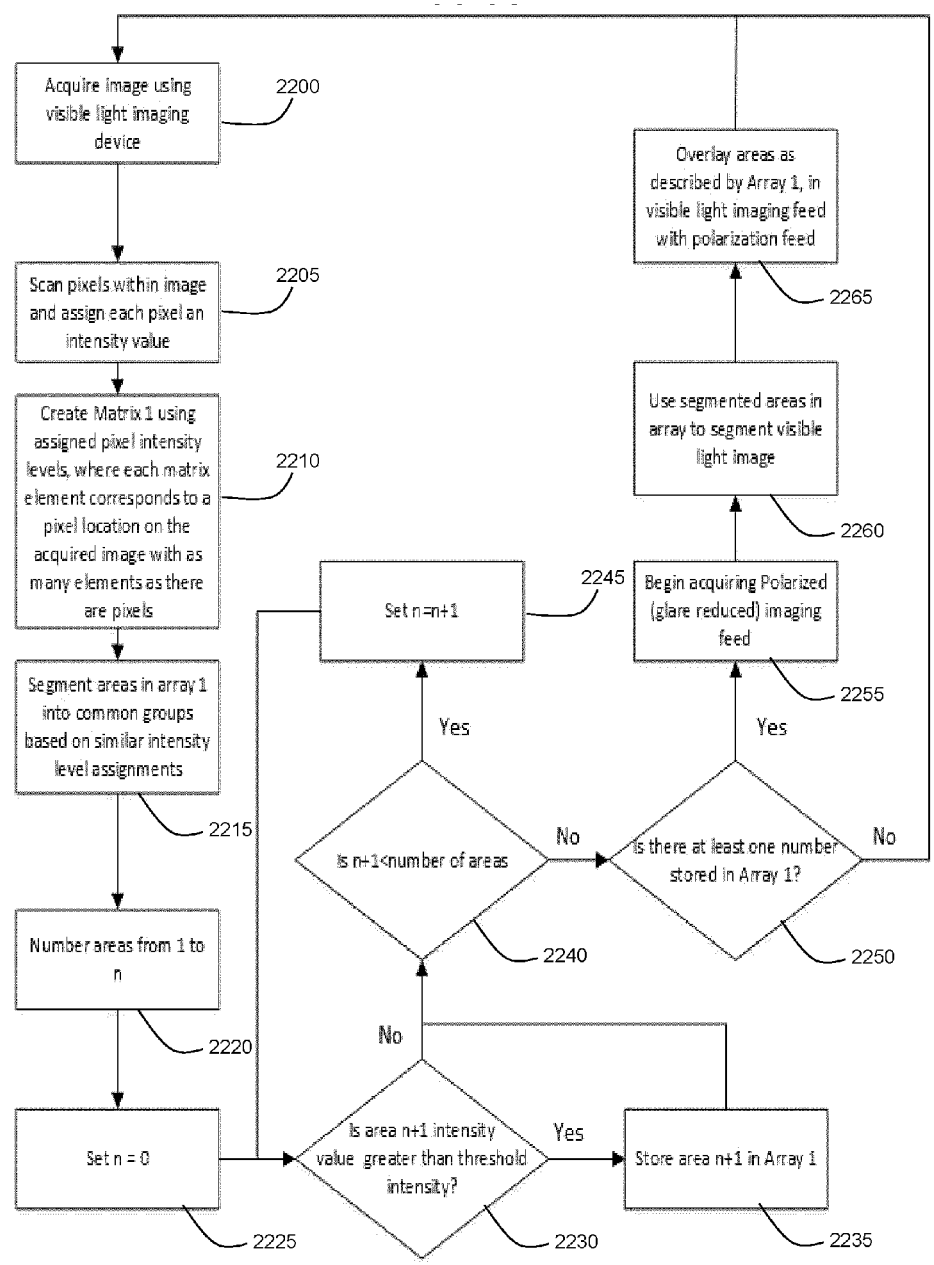
FIG. 22 is a flow chart describing the analysis of images and activation of polarization imaging.

In one embodiment, the adaptive system may be utilized to configure the imaging device (video scope) to reduce glare conditions at the surgical site of interest. The process, as illustrated in FIG. 22. The first step (2200) in this process is to acquire a visible light image from the imaging device (for example an external scope). The following step (2205) in the process is to scan the signal from each pixel within the region of interest on the acquired image, assigning each pixel an intensity value based on the dynamic range of the imaging device (in a port based surgery this would be the distal end of the port, where the surgical site is located and tumor resection is being performed by the surgeon). Using these values, the third stage in the process (2210) is to create a matrix using these pixels, where each element of the matrix corresponds to a pixel location on the image and the corresponding matrix element locations are conserved with respect to their pixel counterparts.

The next step in the process (2215) is to identify areas (defined by >x number of pixels in a row in the X direction and >y number of pixels in a row in the Y direction (X and Y being chosen values for a minimum area)) of groups of pixels with similar intensities. Step (2220) is to assign each area a value from 1 to n, continuing with the flow chart.

In step (2225), n is to zero, so that in the following step (2230), the n=1 case is considered (since step 2230 involves assessing area number n+1). The following steps (2230, 2235, 2240, and 2245) pertain to a loop that determines if each identified area (1 to n) intensity level is indicative of glare conditions. It should be noted that the glare condition can be chosen by a user and input into the adaptive system or predetermined by the adaptive system and is defined by an intensity threshold. The loop stores each area which is indicative glare conditions (i.e. has an intensity above the given threshold) in an array. The next step before continuing (2250) is to check if there are any areas with glare conditions if not the process returns to the first step (2200) and is repeated. If there are glare conditions, the next step (2255) indicates that polarized imaging should begin getting acquired by the imaging device (for example the external scope). In the next step (2260) the imaging stream acquired from the visible light imaging device is segmented according to the areas as defined by the array and located on the matrix. The final step (2265) is to overlay those identified areas using the polarization imaging stream acquired using the imaging device. This overlay effectively reduces the glare conditions for the surgeon as they perform the surgery.

In an embodiment the FIG. 24 illustrates another example method for performing adaptive system may be utilized to configure the imaging device (video scope) to reduce glare conditions. Unlike the intensity-based example method shown in FIG. 22, the present example method employs spectral analysis for the detection of conditions associated with blood occlusion in the surgical site of interest. The process in which this is achieved is depicted in FIG. 24. The first step (2400) in this process is to acquire a visible light image from the imaging device (for example an external scope). The following step (2405) in the process is to scan each pixel within the region of interest on the acquired image assigning each pixel a wavelength (color) spectrum value based on the appropriate range of the visible light spectrum. Using these values the third stage in the process (2410) is to create a matrix using these pixels, where each element of the matrix corresponds to a pixel location on the image and the corresponding Matrix element locations are conserved with respect to their pixel counterparts. The next step in the process (2415) is to identify areas (defined by >x number of pixels in a row in the X direction and >y number of pixels in a row in the Y direction (X and Y being chosen values for a minimum area)) of groups of pixels with similar wavelength spectrums. Step (2420) is to assign each area a value from 1 to n, continuing with the flow chart.

In step (2425), n is set initially to zero, so that in the following step (2230), the n=1 case is considered (since step 2430 involves assessing area number n+1). The following steps (2430, 2435, 2440, and 2445) pertain to a loop that determines if each identified area (1 to n) intensity level is indicative of blood occlusion. It should be noted that the blood occlusion can be identified by comparing the assigned wavelength spectrum values to a known value for blood (corresponding to its color). The loop stores each area which is indicative blood occlusion (i.e. has the same wavelength spectrum as blood) in an array. Before continuing the following step (2250) is to check if there are any areas with blood occlusion if not the process returns to the first step (2400) and is repeated. If there is blood occlusion, the next step (2455) indicates that whether the image acquisition based on near-infrared (NIR) imaging should commence (for example by the imaging device acquiring NIR images with the external scope). In the next step (2460) the imaging stream acquired from the visible light imaging device is segmented according to the areas as defined by the array and located on the matrix. The final step (2465) is to overlay those identified areas using the NIR imaging stream acquired using the imaging device. This overlay effectively increases the ability of the surgeon to see through the blood as they perform the surgery.

FIG. 23 is a flow chart depicting the actuation of an example method of utilizing polarization sensitive imaging to determine surface structures. One particular use of this type of imaging would be its use to decipher surface structures that would be representative of vital regions within a patient's brain such as fiber tracts or within the patient's body such as tendons. The first step in this process (2300) is to acquire the spatial position of the instrument (such as a resection device) in the spatially registered intraoperative reference frame associated with the Navigation system (i.e. using the tracking device within used by the Navigation system). The second step (2310) is to spatially register the position of the preoperative 3D MRI image data in the common coordinate frame from the Navigation system.

The following two steps (2320) and (2330) are used to determine whether the instrument comes close to a fiber tract, if the instrument approaches a fiber tract in close proximity (e.g. within a pre-selected distance). If it is deemed that the instrument is not close to a fiber tract, the process returns to the initial step (2300) and repeats. If it is determined that the instrument comes close to a fiber tract, the system control and processing unit 400 configures the imaging device to begin acquiring polarization sensitive imaging (2350) and displays the imaging to the surgeon (2340). This allows the surgeon to potentially decipher any brain tracts that he may damage while performing resection and allows him to stay clear of those vital areas. The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A computer implemented method of adaptively and intraoperatively configuring an imaging device used during a medical procedure, the method comprising:

during the medical procedure, detecting, with a detection device, one or more signals or images associated with a plurality of medical instruments employed concurrently during the medical procedure;

processing the one or more signals or images to intraoperatively identify the medical instruments during the medical procedure;

performing one or more intraoperative diagnostic measurements, thereby obtaining intraoperative diagnostic data;

processing the intraoperative diagnostic data to determine the current phase of the medical procedure;

accessing configuration data from a data storage device, the configuration data associating customized configuration parameters for the imaging device with the identities of different medical instruments and with phases of a medical procedure, wherein the customized configuration parameters are selected and ranked based on the identities of different medical instruments;

processing the configuration data to determine, based on the medical instrument having the highest ranking and the current phase of the medical procedure, one or more customized configuration parameters for adaptively configuring the imaging device during the medical procedure; and intraoperatively configuring the imaging device according to the customized configuration parameters;

wherein the imaging device is a separate device that is not connected to the medical instrument during the medical procedure.

2. The method according to claim 1 wherein the medical instrument is identified by:

detecting a signal from one or more fiducial markers associated with the medical instrument; and processing the signal to identify the medical instrument.

3. The method according to claim 2 wherein the one or more fiducial markers are selected from the group consisting of passive markers, active markers, glyphs and RFID tags.

4. The method according to claim 2 wherein the medical instrument is identified based on image analysis employing a known shape of the medical instrument.

5. The method according to claim 1 wherein identifying one or more medical devices comprises receiving input from an operator, wherein the input from the operator identifies the medical instrument.

6. The method according to claim 1 wherein identifying the medical instrument comprises identifying the type of the medical instrument.

7. The method according to claim 1 wherein identifying the medical instrument comprises uniquely identifying the medical instrument.

8. The method according to claim 7 wherein uniquely identified medical instrument is associated with one or more operators.

9. The method according to claim 7 wherein uniquely identified medical instrument is associated with one or more regions of use.

10. The method according to claim 1 further comprising:

receiving input identifying one or more operators present during the medical procedure;

wherein the customized configuration parameters are further associated with the identity of the one or more operators.

11. The method according to claim 1 wherein the customized configuration parameters comprise one or more of colour balance, brightness, depth of field, magnification, field of view, working distance, and illumination conditions.

12. The method according to claim 1 wherein the imaging device is a multimodal imaging device, and wherein the customized configuration parameters comprise a selection of an imaging modality.

13. The method according to claim 1 wherein the medical procedure is a surgical procedure.

* * * * *